(12) United States Patent
Nishimura

(10) Patent No.: US 10,874,360 B2
(45) Date of Patent: Dec. 29, 2020

(54) X-RAY TOMOGRAPHY APPARATUS AND X-RAY TOMOGRAPHY METHOD

(71) Applicant: J. MORITA MANUFACTURING CORPORATION, Kyoto-Shi, Kyoto (JP)

(72) Inventor: Yuu Nishimura, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 0 days.

(21) Appl. No.: 16/490,075

(22) PCT Filed: Mar. 2, 2018

(86) PCT No.: PCT/JP2018/008063
§ 371 (c)(1),
(2) Date: Aug. 30, 2019

(87) PCT Pub. No.: WO2018/159820
PCT Pub. Date: Sep. 7, 2018

(65) Prior Publication Data
US 2020/0008760 A1    Jan. 9, 2020

(30) Foreign Application Priority Data
Mar. 2, 2017    (JP) .................................. 2017-039345

(51) Int. Cl.
*A61B 6/14* (2006.01)
*A61B 6/02* (2006.01)
(Continued)

(52) U.S. Cl.
CPC ................ *A61B 6/14* (2013.01); *A61B 6/025* (2013.01); *A61B 6/542* (2013.01); *A61B 6/032* (2013.01)

(58) Field of Classification Search
CPC ........... A61B 6/025; A61B 6/032; A61B 6/14; A61B 6/542
See application file for complete search history.

(56) References Cited

U.S. PATENT DOCUMENTS 6,289,074 B1 *  9/2001  Arai ....................... A61B 6/032
                                                        378/38
6,493,415 B1 * 12/2002  Arai ........................ A61B 6/14
                                                        378/38
(Continued)

FOREIGN PATENT DOCUMENTS

JP    2004-321587 A    11/2004
JP    2006-288726 A    10/2006
(Continued)

OTHER PUBLICATIONS

The Search Report from the corresponding International Patent Application No. PCT/JP2018/008063 dated Jun. 5, 2018.
(Continued)

*Primary Examiner* — Thomas R Artman
(74) *Attorney, Agent, or Firm* — Shinjyu Global IP

(57) ABSTRACT

A dose setting unit generates dose control data in order to change a unit time dose of an X-ray beam with which a subject is irradiated during X-ray tomography. An imaging controller makes X-ray intensity when a center axis X-ray (irradiation axis) of an X-ray beam emitted from an X-ray generator is not orthogonal to a tomographic layer of interest relatively smaller than X-ray intensity when the center axis X-ray is orthogonal to the tomographic layer of interest.

14 Claims, 31 Drawing Sheets

(51) Int. Cl.
*A61B 6/00* (2006.01)
*A61B 6/03* (2006.01)

(56) References Cited

U.S. PATENT DOCUMENTS

| | | | | |
|---|---|---|---|---|
| 7,136,452 | B2* | 11/2006 | Spartiotis | A61B 6/14 378/19 |
| 7,697,661 | B2* | 4/2010 | Souchay | A61B 6/542 378/37 |
| 9,668,705 | B2* | 6/2017 | Yamakawa | A61B 6/583 |
| 2004/0000630 | A1* | 1/2004 | Spartiotis | G01T 1/2964 250/208.1 |
| 2008/0056441 | A1 | 3/2008 | Souchay et al. | |
| 2010/0067650 | A1 | 3/2010 | Arai et al. | |
| 2012/0140878 | A1 | 6/2012 | Souchay | |
| 2013/0294569 | A1 | 11/2013 | Yoshikawa et al. | |
| 2015/0305696 | A1* | 10/2015 | Yamakawa | A61B 6/14 378/19 |
| 2020/0008760 | A1* | 1/2020 | Nishimura | A61B 6/542 |

FOREIGN PATENT DOCUMENTS

| | | |
|---|---|---|
| JP | 2008-062058 A | 3/2008 |
| JP | 2010-075682 A | 4/2010 |
| JP | 2012-115677 A | 6/2012 |

OTHER PUBLICATIONS

The Search Report from the corresponding European Patent Application No. 18761564.6 dated Oct. 12, 2020.

* cited by examiner

F I G. 2 1
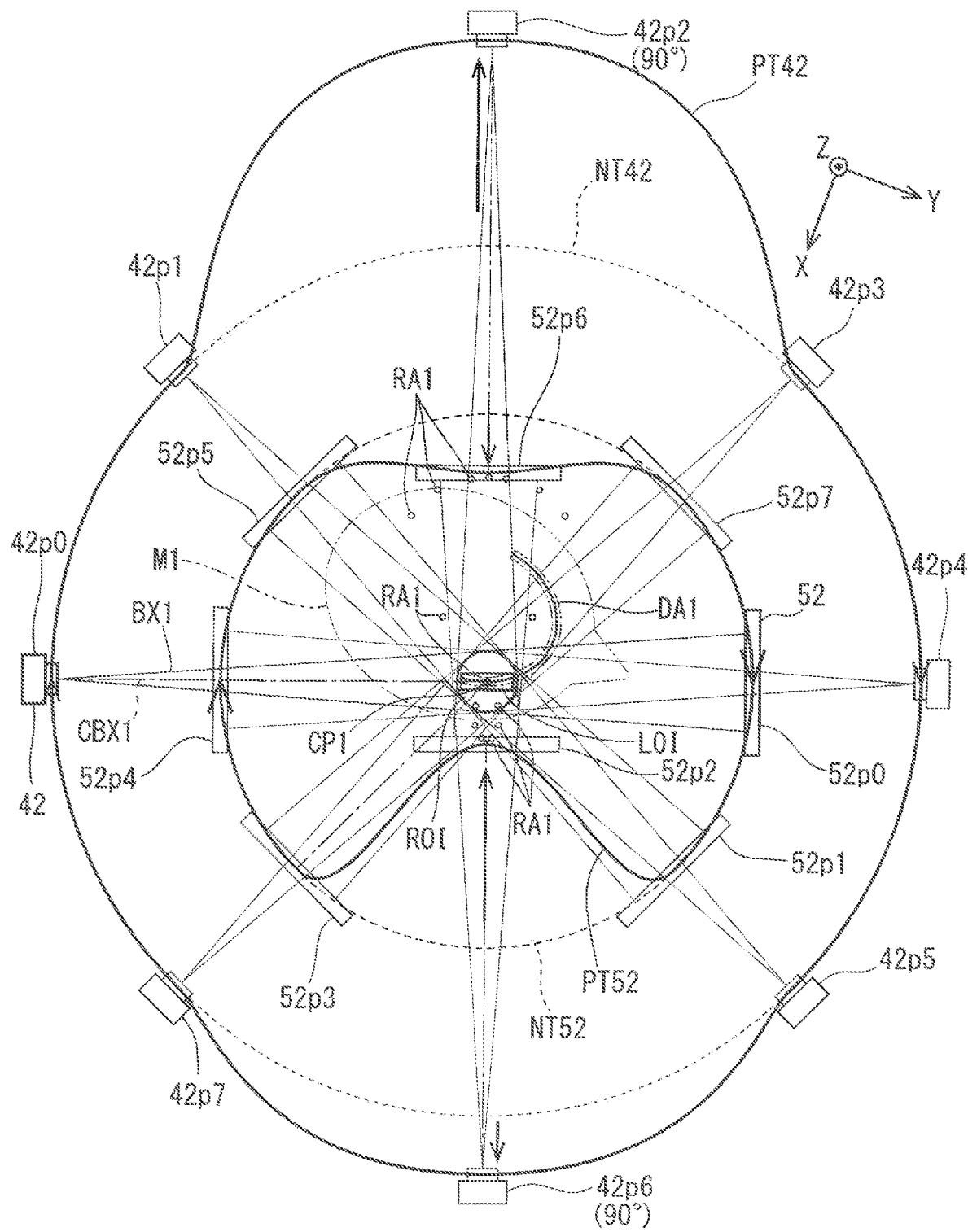

F I G. 3 1
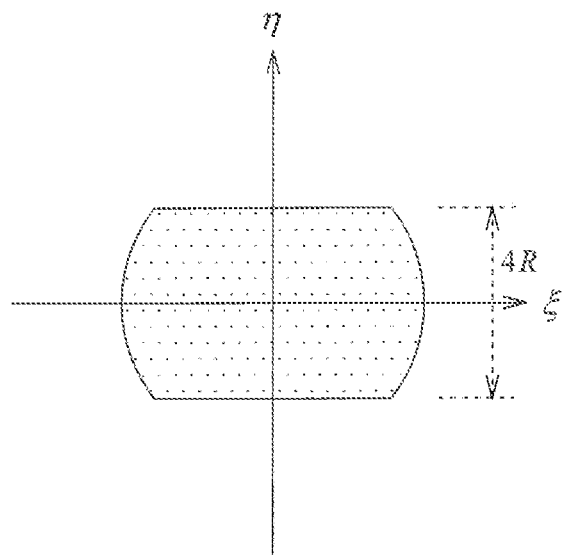
F I G. 3 2
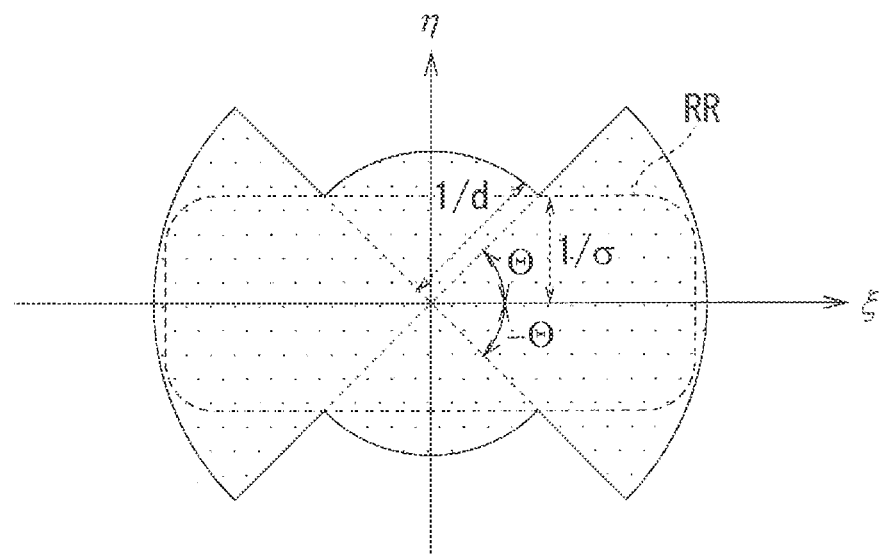

X-RAY TOMOGRAPHY APPARATUS AND X-RAY TOMOGRAPHY METHOD

CROSS-REFERENCE TO RELATED APPLICATIONS

This application is the National Phase in the United States of PCT/JP2018/008063, filed Mar. 2, 2018, which claims priority to Japanese Patent Application No. 2017-039345, filed Mar. 2, 2017. Those applications are incorporated by reference in their entireties.

TECHNICAL FIELD

The present invention relates to a technique of performing X-ray tomography to acquire an X-ray tomographic image.

BACKGROUND ART

An X-ray CT (computed tomography) imaging apparatus that performs tomographic imaging on any site of a human body is widely known in the field of medical X-ray diagnosis. In the X-ray CT imaging apparatus, image information (an X-ray projection image or a transmission image) is acquired by rotating an X-ray generator and an X-ray detector, which are disposed opposite to each other, around a subject. The obtained image information is subjected to image processing to generate the X-ray tomographic image illustrating a tomographic plane obtained by cutting any site such as a head and a body.

Japanese Patent Application Publication No. 2006-288726 discloses a technique of performing CT imaging by reducing an influence of a high X-ray absorption site existing in the subject using a control model based on high X-ray absorption site information existing in the subject. Specifically, at least one of an increase in X-ray output and a decrease in turning speed is performed at timing at which an X-ray cone beam reaches the high X-ray absorption site (for example, a cervical spine). In Japanese Patent Application Publication No. 2006-288726, a clear X-ray tomographic image is acquired by reducing the influence of the high X-ray absorption site.

BRIEF SUMMARY

In the technique of Japanese Patent Application Publication No. 2006-288726, an increased dose is absorbed by the high X-ray absorption site. For this reason, as to an amount of information about the X-ray absorption in the target imaging region, the case where the influence of the high X-ray absorption site is reduced is substantially equal to the case where the high X-ray absorption site does not exist. Resolution of the X-ray tomographic image obtained by reducing the influence of the high X-ray absorption site is almost equal to the case where the high X-ray absorption site does not exist, and an X-ray exposure dose increases by the increased dose.

On the other hand, in order to generate the high-resolution X-ray tomographic image, the dose with which the imaging region is irradiated can be increased more than usual. However, there is a problem in that the X-ray exposure dose of the subject is increased.

An object of the present invention is to provide a technique of acquiring the high-resolution X-ray tomographic image while preventing the increase in the X-ray exposure dose.

In order to solve the above problems, according to a first aspect, an X-ray tomography apparatus includes: an X-ray generator that emits an X-ray beam; an X-ray detector that detects the X-ray beam emitted from the X-ray generator; a support that supports the X-ray generator and the X-ray detector; a tomographic layer-of-interest setting unit that sets a position of a tomographic layer of interest; a turning drive unit that relatively turns the X-ray generator and the X-ray detector around at least a turning center axis with respect to the tomographic layer of interest; an image processor that generates an X-ray tomographic image indicating the tomographic layer of interest by performing image processing on a projection image generated based on an output signal output from the X-ray detector; and a controller that controls the turning drive unit and a change in a unit time dose that is an X-ray dose with which the tomographic layer of interest is irradiated per unit time. The controller controls the turning drive unit and said change in the unit time dose such that the unit time dose in at least a part of a period in which a center axis of the X-ray beam is not orthogonal to the tomographic layer of interest is relatively smaller than the unit time dose in a period in which the center axis of the X-ray beam is orthogonal to the tomographic layer of interest.

A second aspect is the X-ray tomography apparatus of the first aspect, in which the support includes a turning arm that supports the X-ray generator at one end side while supporting the X-ray detector at the other end side, and the turning drive unit turns the turning arm via a shaft, the shaft being connected to a position between the X-ray generator and the X-ray detector in the turning arm.

A third aspect is the X-ray tomography apparatus of the first aspect or the second aspect, which further includes an imaging region setting unit that sets an imaging region irradiated by the X-ray beam from a plurality of directions whereby a plurality of projection images are acquired, the imaging region setting unit sets the imaging region based on an input operation of designation through an operation unit.

A fourth aspect is the X-ray tomography apparatus of the third aspect, in which the tomographic layer-of-interest setting unit sets said position of the tomographic layer of interest according to the imaging region set by the imaging region setting unit.

A fifth aspect is the X-ray tomography apparatus of the fourth aspect, in which the operation unit receives designation of the imaging region so as to include a part of a dental arch, and the tomographic layer-of-interest setting unit sets the tomographic layer of interest along the part of the dental arch included in the imaging region to the tomographic layer of interest.

A sixth aspect is the X-ray tomography apparatus of any one of the first aspect to the fifth aspect, in which the controller increases or decreases the unit time dose by increasing or decreasing intensity of the X-ray beam emitted from the X-ray generator, and the image processor generates the X-ray tomographic image after performing smoothing processing on the projection image obtained by irradiation of the X-ray beam having intensity lower than a predetermined threshold.

A seventh aspect is the X-ray tomography apparatus of any one of the first aspect to the sixth aspect, further including a tomographic thickness designation receiving unit that receives designation of a tomographic thickness of the tomographic layer of interest. The controller determines an incident angle of the X-ray beam when the unit time dose is increased and decreased according to the designated tomographic thickness.

An eighth aspect is the X-ray tomography apparatus of the third aspect, in which based on position information indicating a position of a high X-ray absorption site where X-ray absorptance is higher than that of other sites, the controller makes the unit time dose when the high X-ray absorption site is present on a path of the X-ray beam lager than the unit time dose when the high X-ray absorption site is absent.

A ninth aspect is the X-ray tomography apparatus of any one of the first aspect to the eighth aspect, further including a movement drive unit that moves the X-ray detector relative to the tomographic layer of interest in a direction perpendicular to the turning center axis. When the center axis of the X-ray beam is orthogonal to the tomographic layer of interest, the controller controls said movement drive unit to causes the X-ray detector to approach the tomographic layer of interest or move the X-ray generator away from the tomographic layer of interest as compared with at least a part of the period in which the center axis of the X-ray beam is not orthogonal to the tomographic layer of interest.

According to a tenth aspect, an X-ray tomography method includes: (a) a step of setting a position of a tomographic layer of interest; (b) a step of relatively turning an X-ray generator and an X-ray detector around a turning center axis with respect to the tomographic layer of interest while the tomographic layer of interest is disposed between the X-ray generator and the X-ray detector; (c) a step of detecting an X-ray beam emitted from the X-ray generator in the step (b) using the X-ray detector; (d) a step of changing a unit time dose that is an X-ray dose with which the tomographic layer of interest is irradiated per unit time in the step (b); and (e) a step of generating an X-ray tomographic image indicating the tomographic layer of interest by performing image processing on a plurality of projection images generated based on an output signal output from the X-ray detector in the step (c). The step (d) is a step of changing the unit time dose such that the unit time dose in at least a part of a period in which a center axis of the X-ray beam is not orthogonal to the tomographic layer of interest is relatively smaller than the unit time dose in a period in which the center axis of the X-ray beam is orthogonal to the tomographic layer of interest.

According to an eleventh aspect, an X-ray tomography apparatus includes: an X-ray generator that emits an X-ray beam; an X-ray detector that detects the X-ray beam emitted from the X-ray generator; a support that supports the X-ray generator and the X-ray detector; a tomographic layer-of-interest setting unit that sets a position of a tomographic layer of interest; a turning drive unit that relatively turns the X-ray generator and the X-ray detector around at least a turning center axis with respect to the tomographic layer of interest; an image processor that generates an X-ray tomographic image indicating the tomographic layer of interest by performing image processing on a projection image generated based on an output signal output from the X-ray detector; and a controller that controls the turning drive unit and an increase or decrease in a unit time dose that is an X-ray dose with which the tomographic layer of interest is irradiated per unit time. The controller controls the turning drive unit and a change in the unit time dose such that the unit time dose in a period in which the X-ray beam is incident on the tomographic layer of interest in a confronting manner is relatively larger than the unit time dose in at least a part of a period in which the X-ray beam is not incident on the tomographic layer of interest in the confronting manner.

According to a twelfth aspect, an X-ray tomography apparatus includes: an X-ray generator that emits an X-ray beam; an X-ray detector that detects the X-ray beam emitted from the X-ray generator; a support that supports the X-ray generator and the X-ray detector; a tomographic layer-of-interest setting unit that sets a position of a tomographic layer of interest; a turning drive unit that relatively turns the X-ray generator and the X-ray detector around at least a turning center axis with respect to the tomographic layer of interest; an image processor that generates an X-ray tomographic image indicating the tomographic layer of interest by performing image processing on a projection image generated based on an output signal output from the X-ray detector; and a controller that controls the turning drive unit and a change in a unit time dose that is an X-ray dose with which the tomographic layer of interest is irradiated per unit time. Assuming that an incident angle of a center axis of the X-ray beam ranging from 85° to 95° with respect to the tomographic layer of interest is a state in which the X-ray generator confronts the tomographic layer of interest, the controller controls the turning drive unit and said change in the unit time dose such that the unit time dose in at least a part of a period in which the X-ray generator does not confront the tomographic layer of interest is relatively smaller than the unit time dose in a period in which the X-ray generator confronts the tomographic layer of interest.

In the X-ray tomography apparatus of the first aspect, when the center axis of the X-ray beam is orthogonal to the tomographic layer of interest, the high-resolution X-ray projection images can be obtained by the irradiation of the X-rays of the relatively high unit time dose. In addition, the X-ray exposure dose of the subject can be decreased by decreasing the unit time dose in the period in which the center axis of the X-ray beam is not orthogonal to the tomographic layer of interest. Thus, the high-resolution X-ray tomographic image of the tomographic layer of interest can be generated while the X-ray exposure dose of the subject is suppressed.

According to the X-ray tomography apparatus of the second aspect, the turning arm is turned via the shaft, which allows the X-ray generator and the X-ray detector to be integrally turned.

In the X-ray tomography apparatus of the third aspect, an operator can designate the imaging region irradiated with the X-rays in the subject.

In the X-ray tomography apparatus of the fourth aspect, the tomographic layer of interest is automatically set according to the set imaging region, so that the operator can omit the operation to set the tomographic layer of interest.

In the X-ray tomography apparatus of the fifth aspect, when the imaging region is set so as to include a dental arch, the tomographic layer of interest is set along the dental arch. Consequently, the X-ray tomographic image of the tomographic layer of interest suitable for a dental diagnosis can be acquired.

In the X-ray tomography apparatus of the sixth aspect, noise that is easily generated by a low dose can be reduced by performing smoothing processing on the projection image obtained with the low dose. Consequently, a suitable X-ray tomographic image can be generated.

In the X-ray tomography apparatus of the seventh aspect, a suitable incident angle is determined when the unit time dose is changed according to the designated tomographic thickness. Consequently, the X-ray tomographic image indicating the tomographic layer of interest having the designated tomographic thickness can suitably be acquired.

In the X-ray tomography apparatus of the eighth aspect, the X-ray dose absorbed by the high X-ray absorption site can be complemented by increasing the unit time dose when the high X-ray absorption site exists on the path of the X-ray beam. Thus, the degradation of the resolution of the X-ray projection image due to the high X-ray absorption site can be prevented.

In the X-ray tomography apparatus of the ninth aspect, when the center axis of the X-ray beam is orthogonal to the tomographic layer of interest, a magnification factor of the X-ray projection image projected onto the X-ray detector can be decreased by causing the X-ray detector to approach the tomographic layer of interest or move the X-ray generator away from the tomographic layer of interest. Consequently, blurring caused by an influence of the focal spot size of the X-ray can be decreased on the X-ray projection image obtained when the center axis of the X-ray beam is orthogonal to the tomographic layer of interest. This enables the improvement of the resolution of the projected image. Additionally, since the X-ray detector is brought closer to the tomographic layer of interest while limiting to a part of the projection angle when the X-ray generator and the X-ray detector are relatively rotated, the X-ray detector can be prevented from touching the subject or the X-ray generator can be prevented from colliding with another member.

In the X-ray tomography method of the tenth aspect, when the center axis of the X-ray beam is orthogonal to the tomographic layer of interest, the high-resolution X-ray projection image can be acquired by the irradiation of the X-ray having the relatively high unit time dose. In addition, the X-ray exposure dose of the subject can be decreased by decreasing the unit time dose in the period in which the center axis of the X-ray beam is not orthogonal to the tomographic layer of interest. Thus, the high-resolution X-ray tomographic image of the tomographic layer of interest can be generated while the X-ray exposure dose of the subject is suppressed.

In the X-ray tomography apparatus of the eleventh aspect, when the X-ray beam is incident on the tomographic layer of interest in a confronting manner, the high-resolution X-ray projection image can be acquired by the irradiation of the X-ray having relatively high unit time dose as compared to the case where the X-ray beam is not incident on the tomographic layer of interest in the confronting manner. In addition, the X-ray exposure dose of the subject can be decreased by decreasing the unit time dose in the period in which the center axis of the X-ray beam is not orthogonal to the tomographic layer of interest. Thus, the high-resolution X-ray tomographic image of the tomographic layer of interest can be generated while the X-ray exposure dose of the subject is suppressed.

In the X-ray tomography apparatus of the twelfth aspect, when the X-ray beam is incident on the tomographic layer of interest at substantially right angles, the X-ray projection image having high image quality and high resolution can be acquired under good imaging conditions by irradiation of the X-rays having relatively high unit time dose as compared to the case where the X-ray beam is not incident on the tomographic layer of interest at substantially right angles. Additionally, the X-ray exposure dose of the subject can be decreased by decreasing the unit time dose in the period in which the center axis of the X-ray beam is not incident on the tomographic layer of interest at substantially right angles. Thus, the X-ray tomographic image of the tomographic layer of interest can be generated with higher image quality and higher resolution while the X-ray exposure dose of the subject is suppressed.

BRIEF DESCRIPTION OF THE DRAWINGS

FIG. 21 is a view illustrating an example of the X-ray tomography.

FIG. 31 is a view illustrating multiplication of the spatial frequency distribution of the projection data in FIG. 30 and a Gaussian filter H.

FIG. 32 is a view conceptually illustrating the spatial frequency distribution of all pieces of X-ray projection data when smoothing processing is performed on the low-dose X-ray projection image.

DETAILED DESCRIPTION

Figure 1:
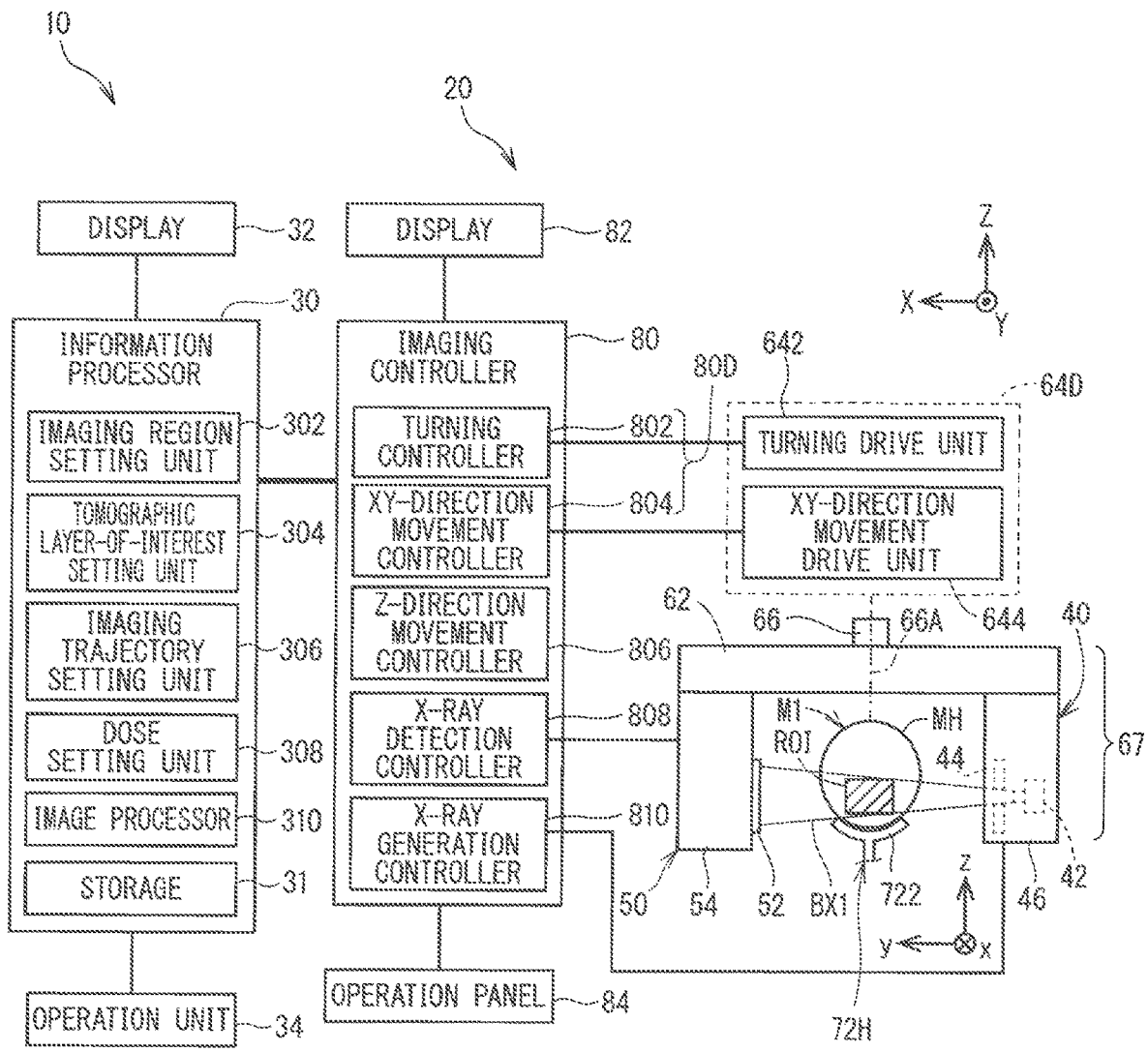
FIG. 1 is a view illustrating a configuration of an X-ray tomography apparatus 10 according to an embodiment.

Hereinafter, an embodiment of the present invention will be described with reference to the accompanying drawings. Constituent elements described in the embodiment are merely examples, and the scope of the present invention is not limited to the constituent elements of the embodiment. In the drawings, for ease of understanding, sometimes dimensions and the number of each portion can be exaggerated or simplified as necessary.

1. Embodiment

Figure 2:
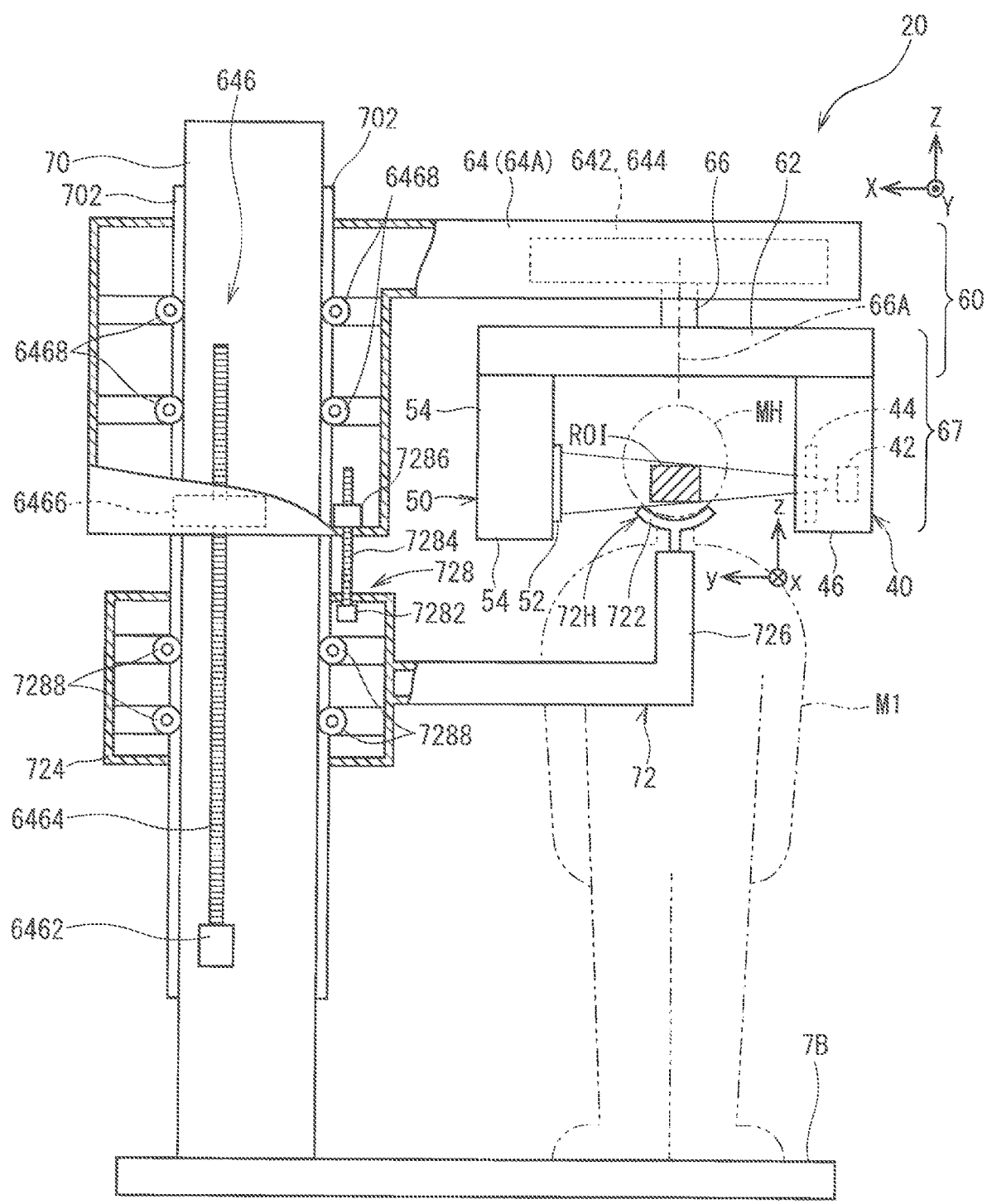
FIG. 2 is a side view schematically illustrating an imaging unit 20 of the embodiment.
Figure 3:
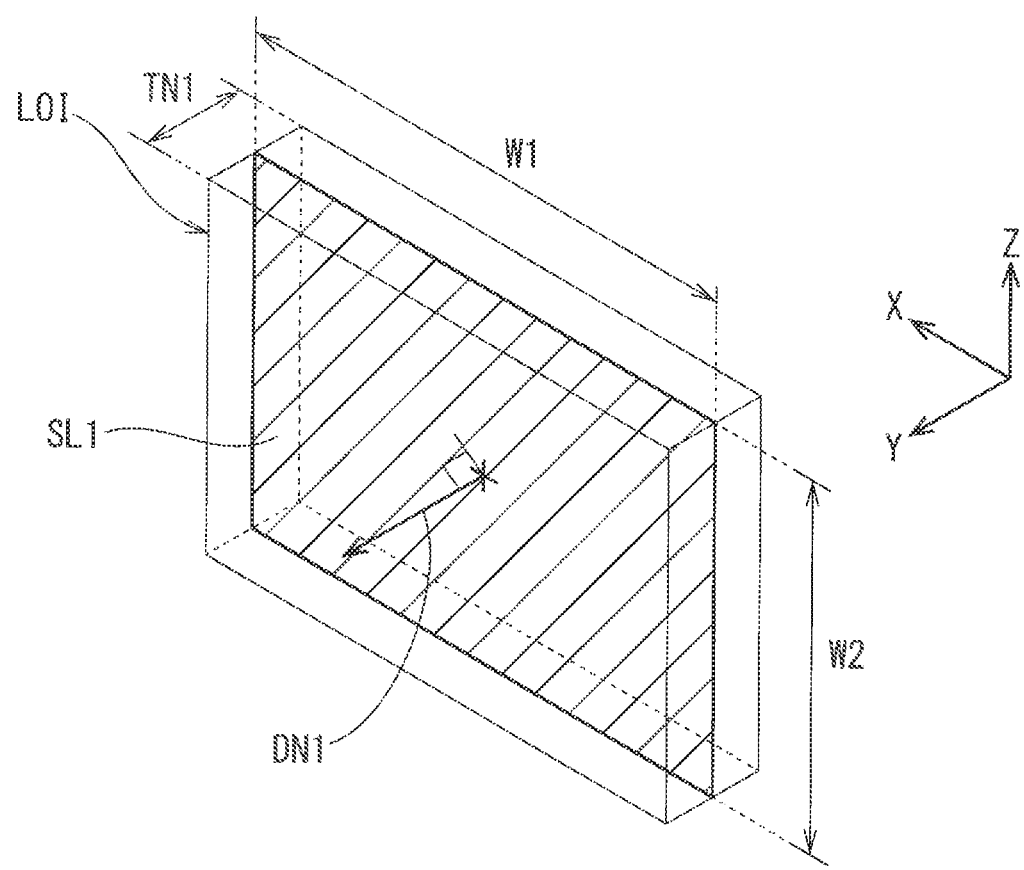
FIG. 3 is a view conceptually illustrating a tomographic layer of interest LOI.

FIG. 1 is a view illustrating a configuration of an X-ray tomography apparatus 10 according to an embodiment. FIG. 2 is a side view schematically illustrating an imaging unit 20 of the embodiment. FIG. 3 is a view conceptually illustrating a tomographic layer of interest LOI.

A right-handed XYZ (X-axis, Y-axis, Z-axis) orthogonal coordinate system and a right-handed xyz (x-axis, y-axis, z-axis) orthogonal coordinate system are defined in FIG. 1. Because a supporting relationship of a post 70 and a support 60 will be described in detail later, the detailed description is not made here, but the supporting relationship will be described in the minimum necessary range for explanation of each axial direction of a coordinate.

The post 70 is erected on a base 7B placed on a ground on which the imaging unit 20 is installed, and an upper frame 64 includes a base end at a portion contacting with the post 70, and extends in one direction crossing a longitudinal direction of the post 70 from the base end. The upper frame 64 pivotally supports a turning unit 67 via a shaft 66. A turning axis 66A about which a turning arm 62 turns mechanically passes through the shaft 66. The axial direction of the turning axis 66A is a Z-axis direction.

The X-ray tomography apparatus 10 in FIG. 1 is a standing type imaging apparatus. The Z-axis direction is a vertical direction, and is made to coincide with a body axis direction of a subject M1 positioned in the imaging unit 20. An arm 726 of a subject holder 72 has a base end in a portion contacting with the post 70, and extends in the same direction as the upper frame 64 from the base end. A head MH of the subject M1 is supported by a head support 72H such as a chin rest 722 provided on a leading end side of the arm 726. The post 70 extends in the Z-axis direction with respect to the base 7B. The base 7B spreads on the ground, and extends to at least a foot of the subject M1.

In the present application, each direction is defined on the assumption that the head MH is positioned and supported at a defined regular location by the head support 72H while facing in a regular direction. A front-rear direction of the head MH is a Y-axis direction, and a left-right direction of the head MH is an X-axis direction. Sometimes the Z-axis direction is referred to as a Z-direction, a Y-axis direction is referred to as a Y-direction, and an X-axis direction is referred to as an X-direction. A front of the head MH, namely, the surface of the imaging unit 20 viewed from the direction in which the face is viewed from the front is set to the front of the imaging unit 20.

FIG. 2 is a front view of the imaging unit 20. In the front view, the upper frame 64 and the arm 726 extend in the X-direction (the −X-direction described below) from the post 70. The upper frame 64 and the arm 726 do not necessarily extend only in the X-direction. Alternatively, for example, the upper frame 64 and the arm 726 can once extend in the Y-direction (the −Y-direction to be described below) and extend in the X-direction on the way.

A + side and a − side in each axial direction will be described below. The direction from the head MH toward the base 7B, namely, a lower side is set to a −Z-side, and the direction away from the base 7B, namely, an upper side is set to a +Z-side. In the shaft 66, the side supported by the upper frame 64 is the +Z-side, and the side supporting the turning arm 62 is the −Z-side. The direction in front of the head MH is set to a +Y-side, and the direction at the back of the head MH is set to a −Y-side. A right direction of the head MH is set to a +X-side, and a left direction is set to a −X-side. Each axial direction, each +, and each − are illustrated in a head perspective view MHPI that is a perspective view of the head MH in FIG. 1.

In the present application, a visual line direction is defined as follows. In each axial direction, the direction viewed in ascending order of a numerical value is viewed as a + direction view, and the direction viewed in descending order of the numerical value is set to a − direction view. Specifically, +ZV illustrated in the head perspective view MHPI is a +Z-direction view, −ZV is a −Z-direction view, +YV is a +Y-direction view and −YV is a −Y-direction view, +XV is a +X-direction view, and −XV is a −X-direction view.

An xyz-orthogonal coordinate system is an orthogonal coordinate system defined in the turning arm 62 that rotates with respect to a portion (for example, the post 70) fixed in the imaging unit 20. At this point, the axial direction of the shaft 66 is set to a z-axis direction, and the z-axis direction is matched with the Z-axis direction of an XYZ-orthogonal coordinate system. A direction in which the X-ray generator 42 and the X-ray detector 52 are opposed to each other is set to a y-axis direction, and a direction orthogonal to the y-axis direction and the z-axis direction is set to an x-axis direction. The turning arm 62 rotates with the shaft 66 as a rotation axis, which allows the xyz-orthogonal coordinate system to rotate about the Z-axis (=z-axis) with respect to the XYZ-orthogonal coordinate system. In the present application, sometimes the z-axis direction is referred to as a z-direction, the y-axis direction is referred to as a y-direction, and the x-axis direction is referred to as an x-direction.

In the y-axis direction, the side of the X-ray detector 52 as viewed from the X-ray generator 42 is set to a +y-side. In the x-axis direction, the right side toward the +y-side is set to a +x-side. The upper side in the vertical direction in the z-axis direction is set to a +z-side. Similar to the XYZ-orthogonal coordinate system, in each axial direction, the direction viewed in ascending order of the numerical value is referred to as the + direction view, and the direction viewed in descending order of the numerical value is referred to as the − direction view.

The X-ray tomography apparatus 10 includes the imaging unit 20 and an information processor 30.

Imaging Unit 20

The imaging unit 20 is an apparatus that collects X-ray projection data by performing X-ray tomography of the subject M1. The imaging unit 20 includes an X-ray generation unit 40, an X-ray detection unit 50, the support 60, the post 70, and an imaging controller 80.

X-ray Generator 40

The X-ray generation unit 40 includes the X-ray generator 42 and an X-ray regulating unit 44.

The X-ray generator 42 includes an X-ray tube that is an X-ray source that emits an X-ray. Intensity (output intensity) of an X-ray beam emitted from the X-ray generator 42 can be controlled by changing voltage and/or current supplied to the X-ray tube. Operation of the X-ray generator 42 is controlled by an X-ray generation controller 810 of the imaging controller 80.

The X-ray regulating unit 44 regulates spread of the X-ray beam emitted from the X-ray generator 42, and forms the X-ray beam having a shape according to an imaging purpose. That is, the X-ray regulating unit 44 controls an X-ray irradiation range with respect to the subject M1 (examinee). The operation of the X-ray regulating unit 44 is controlled by the X-ray generation controller 810.

For example, the X-ray regulating unit 44 includes an X-ray shielding member disposed at a position close to the X-ray generator 42 and a moving mechanism (not illustrated) that moves the X-ray shielding member. For example, the X-ray shielding member is constructed with a single plate member in which a plurality of openings having different opening shapes are provided or at least two plate members in which an opening having a required size or shape is formed by moving the plate members in an approaching or separating direction. For example, the moving mechanism is constructed with a ball screw mechanism or a linear motor mechanism.

The X-ray generator 42 and the X-ray regulating unit 44 are accommodated in a casing 46. The casing 46 is supported by the support 60 (in this case, the turning arm 62).

X-ray Detection Unit 50

The X-ray detection unit 50 includes the X-ray detector 52.

The X-ray detector 52 detects an X-ray beam BX1 emitted from the X-ray generator 42. The X-ray detector 52 includes a flat panel detector (FPD) including a detection surface spreading in a flat shape or an X-ray image intensifier (I.I.). In this case, although the detection surface of the X-ray detector 52 is formed in a flat shape, the detection surface can be formed in a curved shape.

The plurality of detecting elements arranged on the detection surface of the X-ray detector 52 convert the intensity of the incident X-ray into an electric signal. The electric signal is input to the imaging controller 80 or the information processor 30 as an output signal, and an X-ray projection image is generated based on the output signal.

The X-ray detector 52 is attached to a side portion of a casing 54 facing the X-ray generator 42, and the X-ray beam is emitted from the X-ray generator 42 to a detection surface of the X-ray detector 52. The casing 54 supporting the X-ray detector 52 is supported by the support 60 (in this case, the turning arm 62).

Support 60

The support 60 includes the turning arm 62 and the upper frame 64. The turning arm 62 is suspended from the upper frame 64 via the shaft 66. The casing 46 is attached to one end of the turning arm 62, and the casing 54 is attached to the other end of the turning arm 62. That is, the turning arm 62 supports the X-ray generator 42 at one end side with the casing 46 interposed therebetween, and supports the X-ray detector 52 at the other end side with the casing 54 interposed therebetween.

The insides of the casings 46, 54 and the turning arm 62 form a series of cavities. Wirings (such as a signal wiring, a power supply wiring, and a control wiring) that operate each elements of the X-ray generation unit 40 and the X-ray detection unit 50 are disposed in the cavities. A working opening used to attach the wiring and a control board or an opening used to radiate heat can be provided at appropriate positions of the casings 46, 54 and the turning arm 62.

As illustrated in FIG. 2, the upper frame 64 is attached to the post 70. The shaft 66 extending in the Z-axis direction is attached to the upper frame 64, and the end of the shaft 66 is connected to an intermediate position between portions supporting the X-ray generation unit 40 and the X-ray detection unit 50 in the turning arm 62. Consequently, the turning arm 62 is suspended from the upper frame 64 via the shaft 66.

A turning drive unit 642 is provided in the upper frame 64. The turning drive unit 642 rotates the shaft 66 to turn the turning arm 62 about the shaft 66. Although not illustrated, for example, the turning drive unit 642 includes an endless belt entrained about the shaft 66 and a motor that rotates the endless belt. The turning drive unit 642 can be provided in the turning arm 62. In this case, the turning arm 62 rotates relative to the non-rotating shaft 66. The operation of the turning drive unit 642 is controlled by a turning controller.

A turning axis 66A, which is an axis on which the turning arm 62 turns mechanically, is set in the shaft 66 in design. The turning arm 62, the casing 46, and the casing 54 constitute a turning unit 67. The upper frame 64 is a turning support 64A that supports the turning unit 67 via the shaft 66. The turning arm 62 turns about the axis of the shaft 66, whereby the turning unit 67 turns about the turning axis 66A.

The turning arm 62 supports the casing 46 at one end side, and supports the casing 54 at the other end side. Consequently, a part of the turning arm 62 supports the X-ray generator 42 while another part supports the X-ray detector 52, the turning axis 66A being sandwiched between the parts. That is, the support 60 supports the X-ray generator 42 and the X-ray detector 52.

An XY-direction movement drive unit 644 that moves the shaft 66 in the X-axis direction and the Y-axis direction is provided in the upper frame 64. For example, the XY-direction movement drive unit 644 is constructed with an XY-stage.

The XY-direction movement drive unit 644 moves the turning drive unit 642 in the X-axis direction and the Y-axis direction together with the shaft 66. For this reason, the shaft 66 is movable in the XY-plane, and is rotatable about the axis in the Z-axis direction at a specific position after the movement in the XY-plane.

The XY-direction movement drive unit 644 can be provided in the turning arm 62. In this case, the turning arm 62 moves in the X-axis direction and the Y-axis direction relative to the shaft 66 fixed at a constant position in the XY-plane.

Both of the turning drive unit 642 and the XY-direction movement drive unit 644 can be provided in the turning arm 62. In this case, the turning arm 62 moves relatively in the X-axis direction and the Y-axis direction and rotates relatively with respect to the shaft 66, which is fixed at the constant position in the XY-plane and does not rotate.

A Z-direction drive unit 646 that elevates and lowers the upper frame 64 in the Z-axis direction is provided in the upper frame 64 and the post 70. As illustrated in FIG. 2, the Z-direction drive unit 646 includes a motor 6462, a ball screw 6464, a nut 6466, and a plurality (in this case, four) of rollers 6468.

The motor 6462 rotates the ball screw 6464. The ball screw 6464 extends in the Z-axis direction. The nut 6466 is screwed in the ball screw 6464.

Each of the rollers 6468 is engaged with a pair of rails 702 provided on the post 70, and the movement direction of the roller 6468 is restricted such that the roller 6468 moves only in the extending direction (Z-axis direction) of the pair of rails 702.

In the example of FIG. 2, the motor 6462 is attached to the post 70, and the nut 6466 is fixed to the upper frame 64. Each roller 6468 is attached to the upper frame 64.

The motor 6462 rotates the ball screw 6464 clockwise or counterclockwise, whereby the nut 6466 moves upward or downward along the ball screw 6464. At this point, the rollers 6468 move on the pair of rails 702. Consequently, the upper frame 64 is elevated and lowered in the Z-axis direction. The X-ray generation unit 40 and the X-ray detection unit 50, which are supported by the turning arm 62, move in the Z-axis direction in association with the elevating and lowering movement of the upper frame 64.

Post 70

The post 70 is a member extending in the Z-axis direction, and supports the upper frame 64 and the subject holder 72.

Subject Holder 72

The subject holder 72 is a member that holds the subject M1. In this example, the subject holder 72 includes the chin rest 722, a lower frame 724, the arm 726, and an elevation drive unit 728.

The chin rest 722 supports a jaw of the subject M1 to support the head of the subject M1. The subject holder 72 is connected to the lower frame 724 via the arm 726. The subject holder 72 can include a member (an ear rod or an arm sandwiching the left and right of the head of the subject M1) such as an ear rod that fixes the head of the subject M1 from both sides. A mechanical element, which is constructed with the chin rest 722 and the ear rod to fix the head MH of the subject M1, constitutes the subject holder 72 or a part of the subject holder 72 as a head support 72H.

The lower frame 724 is attached to the post 70, and moves in the Z-axis direction. The lower frame 724 moves in the Z-axis direction, whereby the chin rest 722 fixed to the arm 726 moves in the Z-axis direction.

The arm 726 is a member that connects the lower frame 724 and the chin rest 722. In the example of FIG. 2, the arm 726 is constructed with a portion extending in parallel to the XY-plane from the lower frame 724 and a portion, which extends to the Z-axis and is connected to the chin rest 722.

The elevation drive unit 728 includes a motor 7282, a ball screw 7284, a nut 7286, and a plurality of (four in this case) rollers 7288.

The motor 7282 rotates the ball screw 7284. The ball screw 7284 extends in the Z-axis direction. The nut 7286 is screwed in the ball screw 7284.

Each of the rollers 7288 is engaged with the pair of rails 702, and the moving direction of the roller 7288 is restricted so as to move only in the extending direction (Z-axis direction) of the pair of rails 702. In the example of FIG. 2, the motor 7282 and the ball screw 7284 are fixed to the lower frame 724. The nut 7286 is fixed to the upper frame 64. In the illustrated example, the ball screw 7284 extends in the +Z direction from a top of the lower frame 724, and is screwed in the nut 7286 fixed in the vicinity of the bottom of the upper frame 64. Each of the rollers 7288 is attached to the lower frame 724.

When the motor 7282 rotates the ball screw 7284 clockwise or counterclockwise, the lower frame 724 moves upward or downward with respect to the nut 7286 fixed to the upper frame 64. At this point, each of the rollers 7288 moves along the pair of rails 702, whereby the lower frame 724 moves in the Z-axis direction.

The lower frame 724 moves in the Z-axis direction, whereby the chin rest 722 moves along the Z-axis. The support 60 is elevated and lowered with respect to the head MH by the relative movement while the height of the head MH is kept constant, which allows the X-ray irradiation location to be changed in the Z-axis direction. Specifically, the support 60 is elevated and lowered together with the subject holder 72 according to the position of the head MH of the subject M1 using the Z-direction drive unit 646 to fix the head MH to the head support 72H. At the same time as the Z-direction drive unit 646 elevates the support 60, the subject holder 72 can be lowered using the elevation drive unit 728 by the same drive amount relative to the support 60. Alternatively, the subject holder 72 can be raised using the elevation drive unit 728 by the same drive amount relative to the support 60 while the support 60 is lowered using the Z-direction drive unit 646.

The position where the head of the subject M1 is supported can be changed by changing the position in the Z-axis direction of the chin rest 722. For example, the position of the chin rest 722 is set according to the position of the head of the subject M1 in an upright posture.

Imaging Controller 80

The imaging controller 80 controls the operation of each element of the imaging unit 20 to cause the imaging unit 20 to perform the X-ray tomography. A hardware configuration of the imaging controller 80 is similar to that of a general computer or a work station. That is, the imaging controller 80 includes a CPU that performs various arithmetic processing, a ROM that is a read-only memory in which a basic program is stored, a RAM that is a readable and writable memory in which various pieces of information are stored, and a storage in which a control application or data is stored.

The imaging controller 80 includes a turning controller 802, an XY-direction movement controller 804, a Z-direction movement controller 806, an X-ray detection controller 808, and an X-ray generation controller 810. Each controller is a function implemented by the operation of the CPU (general-purpose circuit) according to the controlling application. A part or all of the functions can be implemented in a hardware manner by construction of a dedicated circuit. Among the circuits of the CPU, portions used for various kinds of control by various control applications can be grasped as the controllers 802, 804, 806, 808, and integration thereof can be grasped as the imaging controller 80.

The turning controller 802 controls the turning of the turning arm 62 by controlling the operation of the turning drive unit 642. Specifically, the turning controller 802 changes an irradiation angle of an X-ray beam BX1 with respect to the subject M1 by rotating the X-ray generator 42 supported by the turning arm 62 around the shaft 66.

By controlling the operation of the XY-direction movement drive unit 644, the XY-direction movement controller 804 controls the movement of the turning arm 62 in the X- and Y-axis directions as a result of the movement of the shaft 66 in the X-axis direction and the Y-axis direction. Specifically, the XY-direction movement controller 804 moves the X-ray generator 42 and the X-ray detector 52 in the X-axis direction and the Y-axis direction.

The turning drive unit 642 and the XY-direction movement drive unit 644 constitute a turning movement drive unit 64D, and the turning controller 802 and the XY-direction movement controller 804 constitute a turning movement drive controller 80D.

The Z-direction movement controller 806 controls the movement of the turning arm 62 in the Z-direction by controlling the operation of the Z-direction drive unit 646. Specifically, the Z-direction movement controller 806 moves the X-ray generator 42 and the X-ray detector 52 in the Z-direction.

The X-ray detection controller 808 controls the operation of the X-ray detection unit 50. The X-ray detection controller 808 controls the operation of the X-ray detector 52.

The X-ray generation controller 810 controls the operation of the X-ray generation unit 40. For example, the X-ray generation controller 810 controls the operation of the X-ray generator 42. Specifically, on and off of the X-ray beam emitted from the X-ray generator 42 and the intensity of the X-ray beam are controlled by controlling the voltage or current supplied to the X-ray tube. The X-ray generation controller 810 controls shielding of the X-ray beam by controlling the operation of the X-ray regulating unit 44. The X-ray beam (such as an X-ray narrow beam and an X-ray cone beam) having the shape according to the imaging purpose is formed by the shielding control of the X-ray beam. The X-ray generation controller 810 controls the operation of the X-ray regulating unit 44 to prevent the region other than an imaging region ROI in the subject M1 from being irradiated with the X-ray beam.

A display 82 and an operation panel 84 are connected to the imaging controller 80. The display 82 is constructed with a liquid crystal display or the like, and provided to display various pieces of information. The operation panel 84 is configured of a touch panel display, and is provided for an operator to input various pieces of information (including an imaging condition) to the imaging controller 80.

Information Processor 30

The information processor 30 is connected to the imaging controller 80 so as to be capable of communicating information. A hardware configuration of the information processor 30 is similar to that of a general computer or a work station. That is, the information processor 30 includes a CPU that performs various pieces of arithmetic processing, a ROM that is a read-only memory in which a basic program is stored, a RAM that is a readable and writable memory in which various pieces of information are stored, and a storage 31 in which an application or data is stored.

The information processor 30 includes an imaging region setting unit 302, a tomographic layer-of-interest setting unit 304, an imaging trajectory setting unit 306, a dose setting unit 308, and an image processor 310. Each processor is a function implemented by the operation of the CPU according to the application. However, some or all of these functions can be realized in hardware by a dedicated circuit. Among the circuits of the CPU, portions used for various kinds of control by various control applications can be grasped as the setting units 302, 304, 306, 308, 310, and integration thereof can be grasped as the information processor 30.

Imaging Region Setting Unit 302

The imaging region setting unit 302 has a function of setting the imaging region ROI. The imaging region ROI is a region that, when the imaging unit 20 performs the X-ray tomography, is irradiated with the X-ray beam from a plurality of directions to acquire a plurality of X-ray projection images. The imaging region setting unit 302 sets the imaging region ROI based on an input operation input by the operator through the operation unit 34. A virtual space on arithmetic operation corresponding to a real space of the imaging unit 20 is defined in the information processor 30. The setting of the imaging region ROI means the setting of a position, a size, a shape, and the like of the imaging region ROI in the virtual space defined in the information processor 30. A specific method for setting the imaging region ROI will be described later.

Tomographic Layer-of-Interest Setting Unit 304

The tomographic layer-of-interest setting unit 304 has a function of setting a tomographic layer of interest LOI. The tomographic layer of interest LOI is usually a tomographic layer on which the operator wants to perform the imaging. The tomographic layer-of-interest setting unit 304 sets the tomographic layer of interest LOI based on the information input to the information processor 30 by the operator through the operation unit 34. "The setting of the tomographic layer of interest LOI" means the setting of the tomographic layer of interest LOI in the virtual space defined by the information processor 30.

For example, the tomographic layer of interest LOI is set by the following procedure. That is, as illustrated in FIG. 3, the tomographic layer-of-interest setting unit 304 determines the position, the size, and an orientation (normal direction DN1) of a tomographic plane of interest SL1 based on the operation input of the operator. The tomographic layer-of-interest setting unit 304 sets the tomographic layer of interest LOI having a required thickness in the normal direction DN1 based on the tomographic plane of interest SL1. In the example of FIG. 3, the tomographic layer of interest LOI having a thickness TN1 in the normal direction DN1 is set around the tomographic plane of interest SL1. The thickness TN1 of the tomographic layer of interest LOI can be set based on designated input from the operator, or can be a predetermined specified value. When the thickness TN1 is the specified value, for example, the position of the tomographic layer of interest LOI, characteristics (such as a height, a weight, age, and gender) of the subject, or the specified value according to an imaging site can previously made into a database, stored in the storage 31, and called according to the imaging. A more specific method for setting the tomographic layer of interest LOI will be described later.

Imaging Trajectory Setting Unit 306

The imaging trajectory setting unit 306 has a function of setting trajectories (imaging trajectories) of the X-ray generator 42 and the X-ray detector 52 during the X-ray tomography when the imaging unit 20 performs the X-ray tomography. Specifically, in the imaging trajectory setting unit 306, a turning center axis RA1 parallel to the Z-axis passing through the center of the imaging region ROI is set to the rotation center, and a circular trajectory when the X-ray generator 42 and the X-ray detector 52 are rotated about the turning center axis RA1 at a predetermined rotation radius is set to a normal imaging trajectory. As described later, in the embodiment, sometimes the imaging trajectory setting unit 306 changes the normal imaging trajectory according to the position of the tomographic layer of interest LOI set by the tomographic layer-of-interest setting unit 304. Specifically, the imaging trajectory setting unit 306 changes the normal imaging trajectory to determine the final imaging trajectory such that the X-ray generator 42 is moved away from the tomographic layer of interest LOI and the X-ray detector 52 approaches the tomographic layer of interest LOI when the X-ray generator 42 confronts the tomographic layer of interest LOI. The setting of the imaging trajectory will be described later.

Dose Setting Unit 308

The dose setting unit 308 sets a dose per unit time (a unit time dose) with which the imaging region ROI of the subject M1 including the tomographic layer of interest LOI is irradiated during the X-ray tomography performed in the imaging unit 20. Specifically, the dose setting unit 308 generates dose control data for operating the imaging controller 80 such that at least a part of the unit time dose in the period in which the X-ray generator 42 does not confront the tomographic layer of interest LOI is smaller than the unit time dose in the period in which the X-ray generator 42 confronts the tomographic layer of interest LOI. That is, when considering relatively, the dose setting unit 308 generates the dose control data for operating the imaging controller 80 such that the unit time dose in the period in which the X-ray generator 42 confronts the tomographic layer of interest LOI is larger than at least a part of the unit time dose of the period in which the X-ray generator 42 does not confront the tomographic layer of interest LOI. The setting of the unit time dose will be described later.

When the tomographic layer of interest LOI is set to a front teeth region, as illustrated in FIG. 3, the thickness direction of the thickness TN1 can be matched with the Y-direction, and a width direction of the width W1 can be matched with the X-direction. When the tomographic layer of interest LOI is set to other regions, the vectors in the X- and Y-directions can be adapted for each region.

Image Processor 310

The image processor 310 processes the X-ray projection image, which is generated based on the signal output by the X-ray detector 52 when the imaging unit 20 performs the X-ray tomography, and generates an X-ray tomographic image of the tomographic layer of interest LOI. The X-ray tomographic image generated by the image processor 310 is not limited to the X-ray tomographic image of the tomographic layer of interest LOI. For example, after the X-ray tomography, the operator can receive designation of another tomographic layer at a position different from the tomographic layer of interest LOI in the imaging region ROI, and the image processor 310 can generate the X-ray tomographic image corresponding to the tomographic layer.

As described above, based on the dose control data generated by the dose setting unit 308, while the imaging controller 80 makes the unit time dose in the period in which the X-ray generator 42 does not confront the tomographic layer of interest LOI relatively smaller than the unit time dose in the period in which the X-ray generator 42 confronts the tomographic layer of interest LOI during the X-ray tomography. When the unit time dose decreases, noise is easily generated in the X-ray projection image due to an influence of Poisson noise (shot noise). For this reason, the image processor 310 can perform smoothing processing (blurring processing) on the X-ray projection image obtained by the irradiation of the unit time dose smaller than a predetermined threshold. When the smoothing processing is performed, a smoothing filter (such as a moving average filter and a Gaussian filter) having a required radius can be used.

The smoothing processing can be performed in both the case where the X-ray generator 42 confronts the tomographic layer of interest LOI and the case where the X-ray generator 42 does not confront the tomographic layer of interest LOI. In this case, the size of the radius of the smoothing filter in the smoothing processing can be changed according to a projection angle, the thickness of the tomographic layer, or the magnitude of the unit time dose. The change in the size of the smoothing will be described later.

The display 32 and the operation unit 34 are connected to the information processor 30.

The display 32 is constructed with a liquid crystal display or the like, and provided to display various pieces of information. Specifically, the display 32 displays a display image with which the operator designates a condition of the X-ray tomography, a display image with which the operator designates the imaging region ROI or the tomographic layer of interest LOI, and the X-ray tomographic image generated by the image processor 310.

The operation unit 34 is constructed with various input devices such as a keyboard and a mouse. As an example, the operation unit 34 is operated when the operator designates the imaging region ROI. That is, the operation unit 34 is an example of an imaging region designation unit. The display 32 can have a part or all of the functions of the operation unit 34 by constructing the display 32 with a touch panel. The imaging region ROI and the tomographic layer of interest LOI can be designated through the operation panel 84 connected to the imaging controller 80.

Method for Setting Tomographic Layer of Interest LOI or Imaging Region ROI

A method for setting the tomographic layer of interest LOI or the imaging region ROI will be described below with reference to FIGS. 4 to 8. In the following description, it is assumed that the tomographic layer of interest LOI or the imaging region ROI is set to the jaw in the head of the subject M1. However, the tomographic layer of interest LOI or the imaging region ROI is not limited to the case where the tomographic layer of interest LOI or the imaging region ROI is set to the jaw, and can be set to another site.

Figure 4:
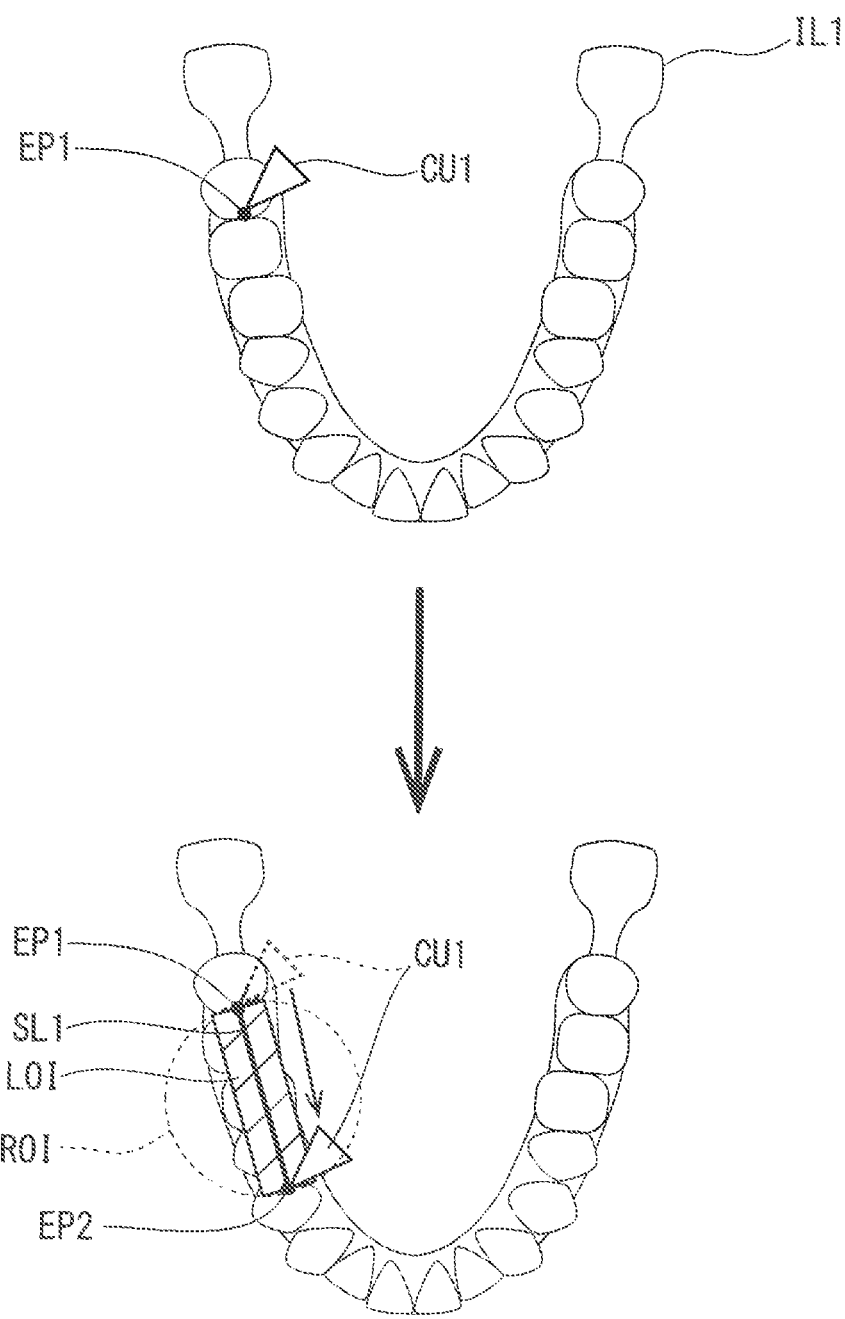
FIG. 4 is a view illustrating a method for setting the tomographic layer of interest LOI.

FIG. 4 is a view illustrating the method for setting the tomographic layer of interest LOI. In the setting method of FIG. 4, the display 32 displays a schematic diagram IL1 that simulates a lower jaw as a designation image for designating the tomographic layer of interest LOI. A plurality of teeth are also drawn in the schematic diagram IL1. The operator designates two end points EP1, EP2 with respect to the schematic diagram IL1 displayed on the display 32 using a cursor CU1. Specifically, when the operation unit 34 includes a mouse, the end points EP1, EP2 can be designated by moving the cursor CU1 through a drag operation. The positions of the end points EP1, EP2 correspond to the positions of two points in the XY-plane in the real space.

The linear tomographic plane of interest SL1 having end points EP1, EP2 at both ends is set when the two end points EP1, EP2 are designated (see FIG. 3). In this case, the end points EP1, EP2 have a width W1 of the tomographic plane of interest SL1. However, the end points EP1, EP2 are not necessarily set to both ends. For example, the tomographic plane of interest SL1 having any width can be set on a straight line passing through the end points EP1, EP2.

When the tomographic plane of interest SL1 is set, the linear tomographic layer of interest LOI having the required thickness TN1 in the normal direction DN1 is set based on the tomographic plane of interest SL1. In FIG. 4, although the tomographic layer of interest LOI is illustrated in planar view, a length (vertical width W2) in a depth direction (corresponding to the Z-axis direction of the real space) of the tomographic layer of interest LOI) is also set appropriately. The vertical width W2 of the tomographic layer of interest LOI can be designated by the operator, or automatically determined according to the physical characteristics (such as the gender, the age, the height, and the weight) or the imaging site of the subject M1 by the tomographic layer-of-interest setting unit 304.

Figure 5:
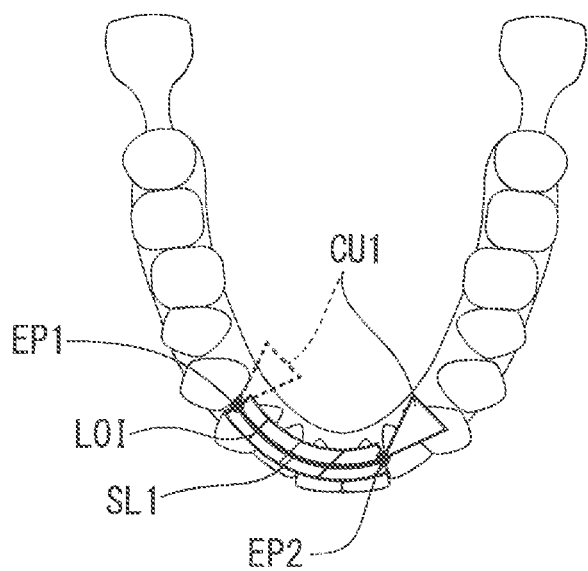
FIG. 5 is a view illustrating the method for setting the tomographic layer of interest LOI.

FIG. 5 is a view illustrating the method for setting the tomographic layer of interest LOI. In the setting method of FIG. 4, the tomographic layer of interest LOI is set to the shape extending linearly in the XY-plane. Alternatively, as illustrated in FIG. 5, the tomographic layer of interest LOI can be set to a curved shape. In this case, for example, when the operator performs a drag operation to move the cursor CU1 in a curved manner, the tomographic layer-of-interest setting unit 304 can set the tomographic plane of interest SL1 to the curved shape according to the movement trajectory of the cursor CU1. The tomographic layer-of-interest setting unit 304 can set the tomographic layer of interest LOI extending in the curved manner based on the tomographic plane of interest SL1.

Figure 6:
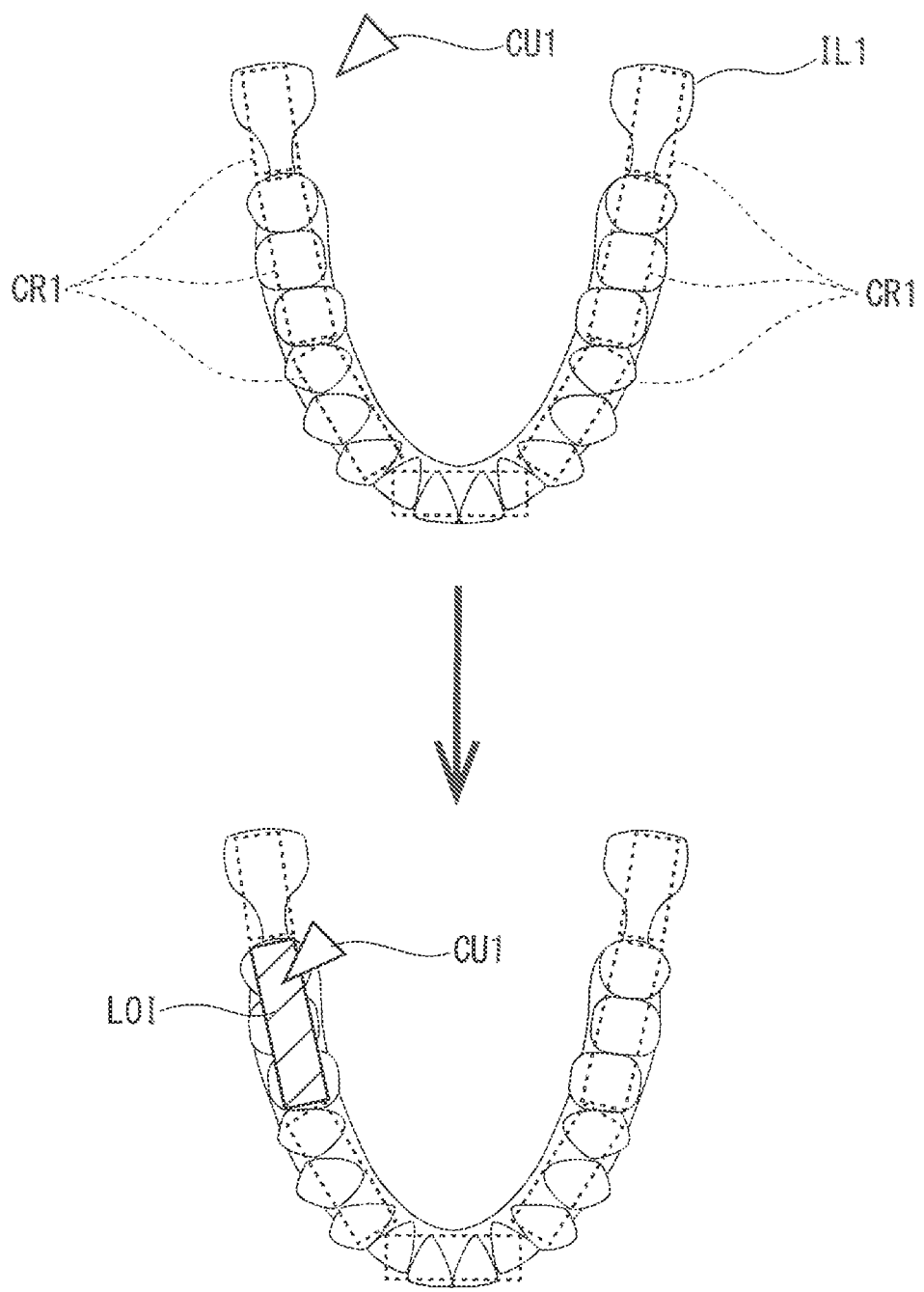
FIG. 6 is a view illustrating the method for setting the tomographic layer of interest LOI.

FIG. 6 is a view illustrating the method for setting the tomographic layer of interest LOI. In the setting methods of FIGS. 4 and 5, the operator sets the tomographic layer of interest LOI to any position. On the other hand, in the setting method of FIG. 6, a plurality of candidate regions that are candidates of the tomographic layer of interest LOI are previously specified, and the operator selects the tomographic layer of interest LOI from among these candidate regions. In the example of FIG. 6, seven candidate regions CR1 are previously determined in the schematic diagram IL1 of the jaw displayed on the display 32, and each candidate region CR1 is displayed by a broken line. When the operator moves the cursor CU1, and performs an operation to select the specific candidate region CR1 from among the plurality of candidate regions CR1, the tomographic layer-of-interest setting unit 304 sets the selected candidate region CR1 to the tomographic layer of interest LOI. In this case, although a degree of freedom in setting the tomographic layer of interest LOI is decreased, the designation operation of the tomographic layer of interest LOI can easily be performed.

Figure 7:
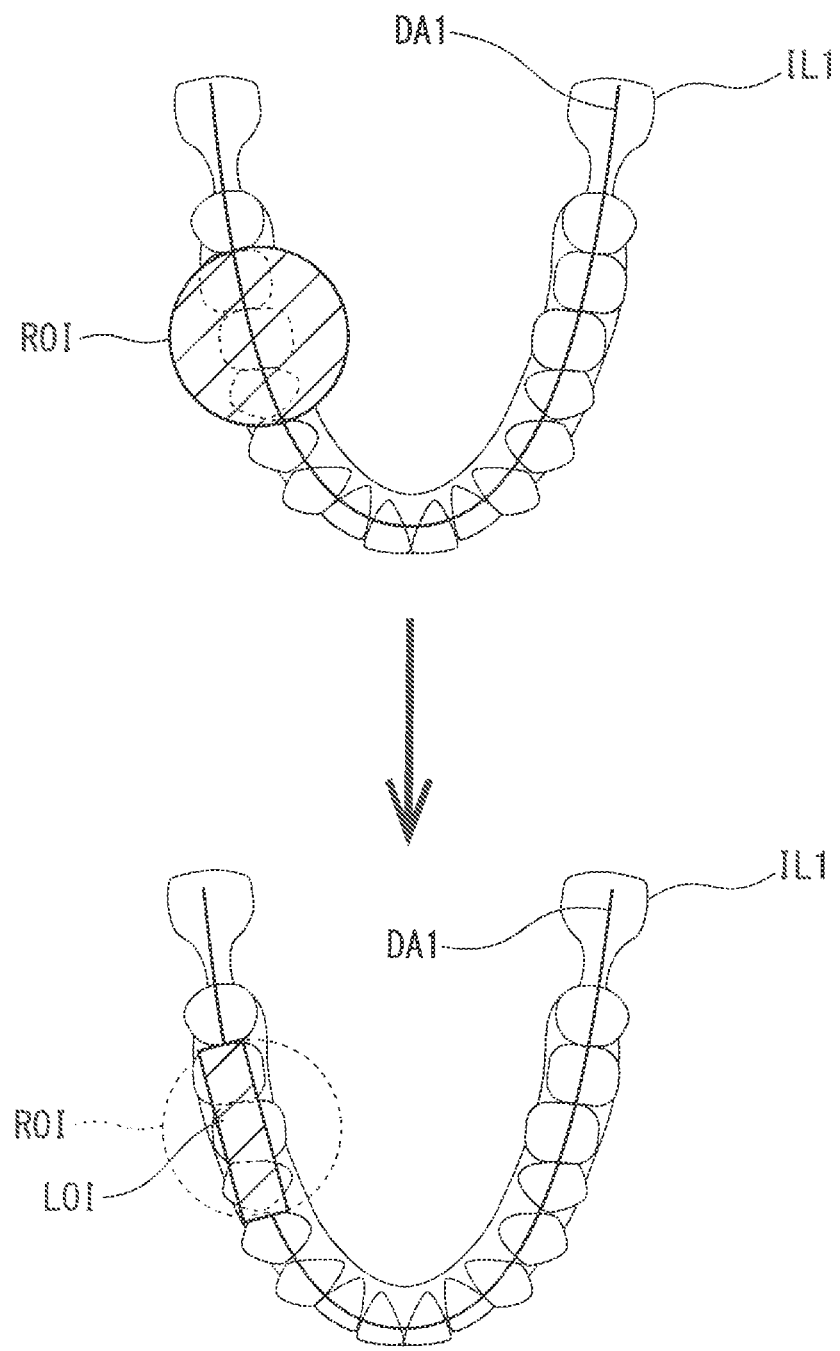
FIG. 7 is a view illustrating a method for setting an imaging region ROI and the tomographic layer of interest LOI.

FIG. 7 is a view illustrating the method for setting the imaging region ROI and the tomographic layer of interest LOI. In the setting method of FIGS. 4 to 6, the operator directly designates the tomographic layer of interest LOI on the designation image. On the other hand, in the setting method of FIG. 7, after the imaging region setting unit 302 sets the imaging region ROI, the tomographic layer-of-interest setting unit 304 automatically sets the tomographic layer of interest LOI according to the imaging region ROI.

For example, the imaging region ROI can be set as follows. That is, the operator designates the position of the imaging region ROI (for example, the center position of the imaging region ROI) and the radius of the imaging region ROI using the cursor CU1 or the like. In response to the designation, the imaging region setting unit 302 sets the imaging region ROI having the designated radius at the designated position. The radius of the imaging region ROI can be designated by numerical input through the keyboard or the like, or designated by the drag operation using the mouse. Circular frames having various radii indicating the size of the imaging region ROI can previously be prepared, and the operator can select the frame having the specific radius from among the circular frames. In this case, the imaging region setting unit 302 can set the imaging region ROI at the position where the selected frame is disposed according to the disposition of the selected frame at the required position on the schematic diagram IL1.

Subsequently, the tomographic layer-of-interest setting unit 304 automatically sets the tomographic layer of interest LOI according to a predetermined rule for the set imaging region ROI. For example, when the imaging target is the jaw, the tomographic layer-of-interest setting unit 304 can set the tomographic layer of interest LOI based on a dental arch DA1 defined along the jaw. For example, as illustrated in FIG. 7, it is assumed that the dental arch DA1 curved into a U-shape is defined in the schematic diagram IL1 of the jaw, and that the imaging region ROI is set so as to include the dental arch DA1. In this case, the tomographic layer-of-interest setting unit 304 can automatically set the tomographic layer of interest LOI along a part of the dental arch DA1 included in the imaging region ROI.

When the linear tomographic layer of interest LOI is set from the curved dental arch DA1, for example, a point on the portion of the dental arch DA1 of the imaging region ROI is taken as a representative point, and the tomographic layer of interest LOI can be set on a tangential line on the representative point of the dental arch DA1. Two points on a portion of the dental arch DA1 in the imaging region ROI can be selected, and the tomographic layer of interest LOI can be set on a straight line connecting the two points.

The curved tomographic layer of interest LOI of the tomographic layer-of-interest setting unit 304 can be set based on the curved dental arch DA1. For example, a curved portion of the dental arch DA1 in the imaging region ROI can be set to the tomographic plane of interest SL1, and a region having a predetermined thickness based on the curved portion can be set to the tomographic layer of interest LOI.

Figure 8:
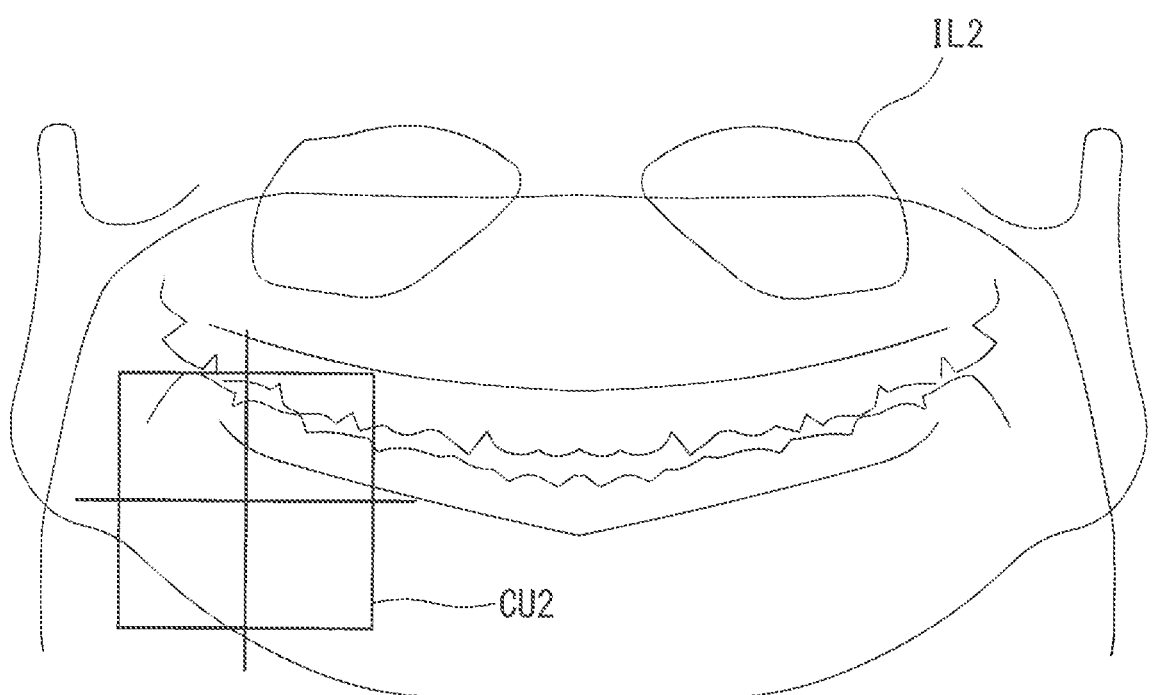
FIG. 8 is a view illustrating the method for setting the tomographic layer of interest LOI.

FIG. 8 is a view illustrating the method for setting the tomographic layer of interest LOI. In the setting method of FIG. 8, a panoramic X-ray image IL2 obtained by previously performing panoramic imaging of the jaw of the subject M1 is used as the designation image. The panoramic X-ray image IL2 is displayed on the display 32, and the tomographic layer of interest LOI or the imaging region ROI is set on the panoramic X-ray image IL2. Each pixel constituting the panoramic X-ray image IL2 has information about a coordinate position on the real space. For this reason, the coordinate position corresponding to the specific portion in the real space is specified when a specific portion on the panoramic X-ray image IL2 is selected using a cursor CU2. At this point, the cursor CU2 includes two straight lines orthogonal to each other. The operator aligns the intersection of the two straight lines with the site to be observed, namely, the tomographic layer of interest LOI, and performs the operation (such as a mouse click operation) to specify the position. When the position of the tomographic layer of interest LOI is designated, as illustrated in FIGS. 4 to 7, the tomographic layer-of-interest setting unit 304 appropriately sets the linear or curved tomographic layer of interest LOI.

The methods for setting the tomographic layer of interest LOI in FIGS. 4 to 8 is merely illustrative. The present invention is not limited to the methods in FIGS. 4 to 8, and the tomographic layer of interest LOI can be set by another method.

For example, a plurality of X-ray projection images (fluoroscopic images) obtained by irradiating the subject M1 with the X-ray beam BX1 from a plurality of directions can be used as the designation image for designating the imaging region ROI or the tomographic layer of interest LOI. For example, the coordinate position on the real space corresponding to the designated position can be specified by receiving the designation of the position of the imaging region ROI or the tomographic layer of interest LOI on two fluoroscopic images obtained by imaging the subject M1 from two directions. The technique described in Japanese Patent Application Laid-Open No. 2004-329293 can be used when the coordinate position in the real space is specified from the fluoroscopic images in the two directions.

After the tomographic layer-of-interest setting unit 304 sets the tomographic layer of interest LOI, the imaging region setting unit 302 can set the imaging region ROI according to the tomographic layer of interest LOI. At this point, the imaging region ROI can be set such that the imaging region setting unit 302 includes the previously-set tomographic layer of interest LOI.

Setting of Unit Time Dose

The setting of the unit time dose during the X-ray tomography will be described below with reference to FIGS. 9 to 17.

Figure 9:
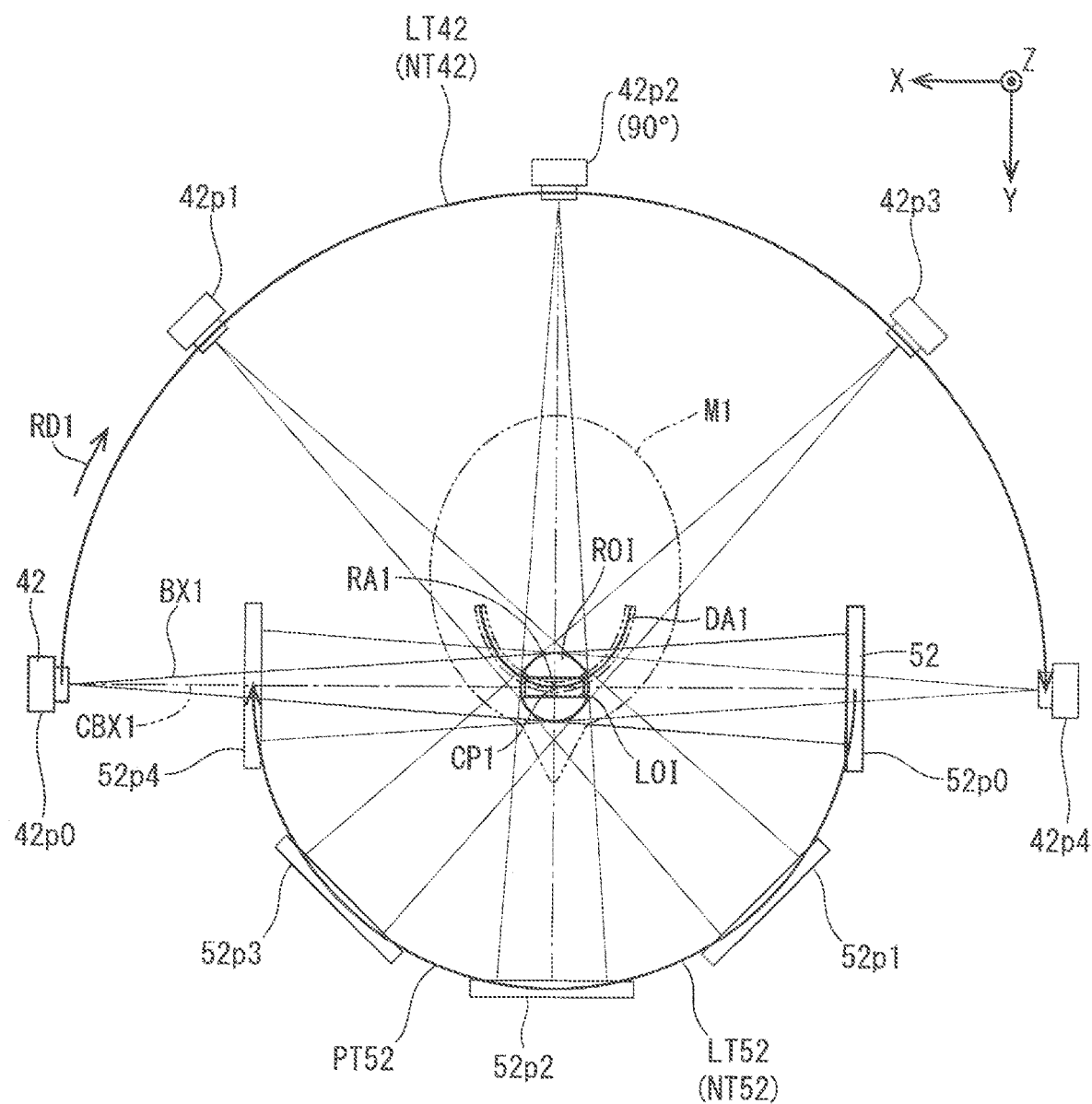
FIG. 9 is a view illustrating an example of X-ray tomography.

FIG. 9 is a view illustrating an example of the X-ray tomography. FIG. 9 is a view illustrating a positional relationship among the X-ray generator 42, the X-ray detector 52, and the subject M1 during the X-ray tomography as viewed from the +Z-side (in Z-direction view). The same applies to FIGS. 13 and 16.

The X-ray tomography in FIG. 9 is CT imaging in which the X-ray generator 42 and the X-ray detector 52 are turned by 180° around the subject M1. A portion including the front teeth is set to the imaging region ROI, and a region extending linearly along the tangential line of a part of the dental arch DA1 included in the imaging region ROI is set to the tomographic layer of interest LOI.

In the CT imaging, the X-ray generator 42 is turned from a position 42p0 on the right side of the head to a position 42p4 on the left side of the head through a position 42p1 to a position 42p3 on a rear side of the head. The X-ray detector 52 is turned from a position 52p0 on the left side of the head to a position 52p4 on the right side of the head through a position 52p1 to a position 52p3 on a front side of the head. An imaging trajectory LT42 (NT42) of the X-ray generator 42 and an imaging trajectory LT52 (NT52) of the X-ray detector 52 are matched with an arc of a semicircle having a predetermined radius centered on a center point CP1 of the imaging region ROI.

The imaging trajectory LT42 of the X-ray generator 42 and the imaging trajectory LT52 of the X-ray detector 52 will be described. The imaging trajectory LT42 of the X-ray generator 42 is a higher-level concept including both a normal imaging trajectory NT42 of the X-ray generator 42 (to be described later) and a magnification factor adjustment imaging trajectory PT42. That is, the imaging trajectory LT42 can be the normal imaging trajectory NT42 or the magnification factor adjustment imaging trajectory PT42. Similarly, the imaging trajectory LT52 of the X-ray detector 52 is a higher-level concept including both a normal imaging trajectory NT52 of the X-ray detector 52 (to be described later) and a magnification factor adjustment imaging trajectory PT52. That is, the imaging trajectory LT52 can be the normal imaging trajectory NT52 or the magnification factor adjustment imaging trajectory PT52.

The turning of the X-ray generator 42 rotates the X-ray beam BX1 advancing from the X-ray generator 42 to the X-ray detector 52. As a result, the angle projected onto the detection surface of the X-ray detector 52 changes with respect to the imaging region ROI. As the irradiation axis of the X-ray beam BX1, attention is paid to the center axis X-ray CBX1 that is the center axis of the X-ray beam BX1, and the rotation angle of the center axis X-ray CBX1 from the time of the start of the X-ray tomography is referred to as the "projection angle". The time of start of the X-ray tomography means the time when the X-ray detector 52 detects the X-ray beam BX1 transmitted through the subject M1 to start the acquisition of the X-ray projection image.

For example, for the CT imaging in FIG. 9, the X-ray generator 42 is disposed at the position 42p0 at the beginning of the X-ray tomography. For this reason, the projection angle when the X-ray generator 42 is located at the position 42p0 is 0°. The projection angle when the X-ray generator 42 is located at the position 42p2 is 90°, and the projection angle when the X-ray generator 42 is located at the position 42p4 is 180°.

Figure 10:
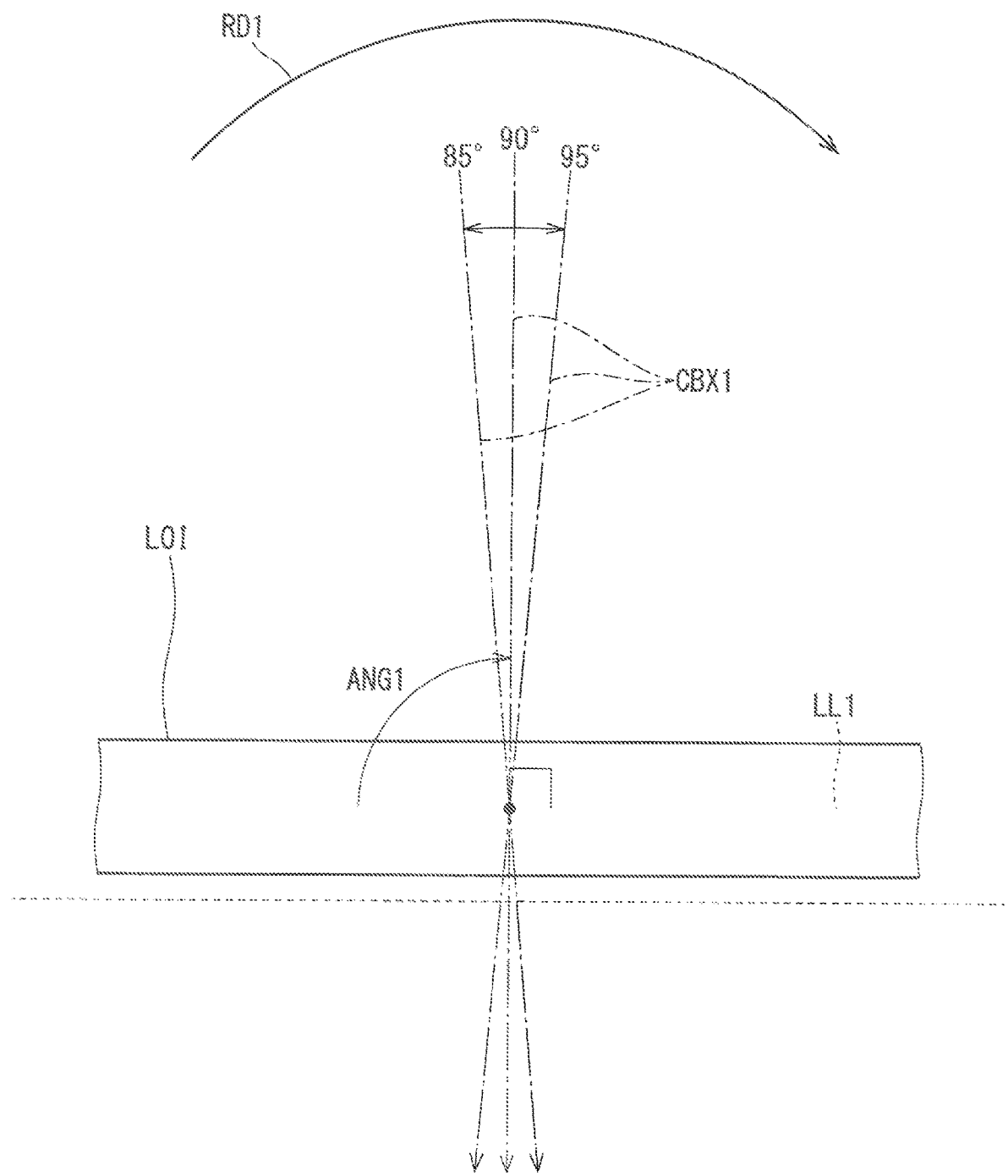
FIG. 10 is a view illustrating a center axis X-ray CBX1 incident on the tomographic layer of interest LOI.

The angle (incident angle) at which the center axis X-ray CBX1 is incident on the tomographic layer of interest LOI also changes by the rotation of the X-ray beam BX1. FIG. 10 is a view illustrating the center axis X-ray CBX1 incident on the tomographic layer of interest LOI. A state in which the center axis X-ray CBX1 is incident on the tomographic layer of interest LOI at substantially right angles means a state in which the X-ray generator 42 confronts the tomographic layer of interest LOI (in other words, the irradiation axis of the X-ray beam BX1 is incident on the tomographic layer of interest LOI in a confronting manner). The term "incident at substantially right angles" means the state in which an incident angle ANG1 of the center axis X-ray CBX1 with respect to the tomographic layer of interest LOI is in a range of 85° to 95°, namely, a range of 90°−5° to 90°+5°, and in particular, in the state in which the center axis X-ray CBX1 is incident at right angles means the state in which the incident angle ANG1 becomes 90°. Needless to say, incident at right angles such as 90° is orthogonal. Incident at substantially right angles can also be referred to as "substantially orthogonal".

An extent to which the range of the substantially right angle is set can be appropriately adjusted from experience of image processing, and can be slightly wider or narrower than 85° to 95°. For example, the range of 82° to 98° and the range of 88° to 92° can also be considered.

As illustrated in FIG. 10, the incident angle ANG1 means an angle around a turning direction RD1 of the X-ray generator 42 from a center line LL1 to the center axis X-ray CBX1 when the center line LL1 passing through the center of the tomographic layer of interest LOI is defined as viewed from the upper side in the Z-axis direction, namely, in Z-direction view. In the CT imaging of FIG. 10, the X-ray generator 42 rotates clockwise with respect to the subject M1 as viewed from the +Z-side, that is, in −Z-direction view. For this reason, the incident angle ANG1 is a clockwise angle from the center line LL1 to the center axis X-ray CBX1. When the tomographic layer of interest LOI is formed into a shape extending in a curved line, the tangential line on the tomographic layer of interest LOI and at any point (for example, a barycentric point of the curve) on the curve along the tomographic layer of interest LOI is set to the center line LL1, and the angle between the center axis X-ray CBX1 and the center line LL1 is set to the incident angle ANG1.

In the CT imaging of FIG. 9, when the X-ray generator 42 is located at the position 42p0 at the beginning of the imaging (when the projection angle is 0°), the incident angle ANG1 is 0°. When the X-ray generator 42 is located at the position 42p2 (when the projection angle is 90°), the incident angle ANG1 is 90°. When the X-ray generator 42 is located at the position 42p4 (when the projection angle is 180°), the incident angle ANG1 is 180°. That is, in this example, the X-ray generator 42 confronts the tomographic layer of interest LOI when passing through the position 42p2.

In performing the CT imaging of FIG. 9, the imaging trajectory setting unit 306 sets the normal imaging trajectories NT42, NT52 of the X-ray generator 42 and the X-ray detector 52. Specifically, the imaging trajectory setting unit 306 sets the normal imaging trajectories NT42, NT52 such that each of the X-ray generator 42 and the X-ray detector 52 moves on a circumference of a semicircle having a predetermined radius centered on the center point CP1 of the imaging region ROI.

The dose setting unit 308 sets the unit time dose corresponding to the projection angle of the X-ray with which the subject M1 is irradiated during the CT imaging in FIG. 9. Specifically, the dose setting unit 308 generates the dose control data for operating the imaging controller 80 such that the unit time dose in the period in which the X-ray generator 42 does not confront the tomographic layer of interest LOI is smaller than the unit time dose in the period in which the X-ray generator 42 confronts the tomographic layer of interest LOI. In other words, the dose setting unit 308 generates the dose control data for operating the imaging controller 80 such that the unit time dose in the period in which the X-ray generator 42 confronts the tomographic layer of interest LOI is larger than the unit time dose in the period in which the X-ray generator 42 does not confront the tomographic layer of interest LOI.

A method for changing the unit time dose includes a method in which the X-ray generation controller 810 changes the X-ray intensity of the X-ray beam BX1 output from the X-ray generator 42 and a method in which turning movement drive controller 80D (in particular, the turning controller 802 for the turning of the turning arm 62) changes the turning velocity of the X-ray generator 42 (the angular velocity of the turning arm 62). In the former method, the dose setting unit 308 can generate the dose control data for operating the X-ray generation controller 810. In the latter method, the dose setting unit 308 can generate the dose control data for operating the turning movement drive controller 80D. The unit time dose can be changed by changing both the X-ray intensity and the turning velocity.

Figure 11:
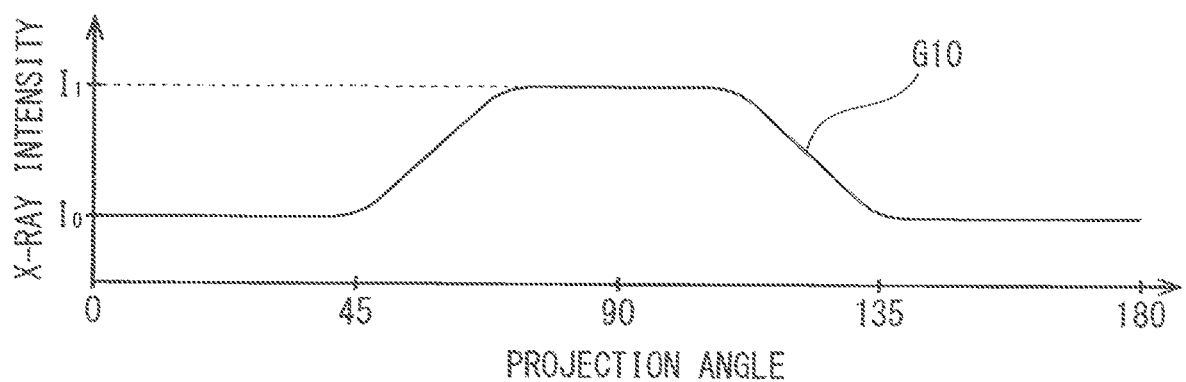
FIG. 11 is a view illustrating a graph G10 of X-ray intensity corresponding to a projection angle in CT imaging of FIG. 9.

FIG. 11 is a view illustrating a graph G10 of the X-ray intensity corresponding to the projection angle in the CT imaging of FIG. 9. In FIG. 11, a horizontal axis indicates the projection angle, and a vertical axis indicates the X-ray intensity. When the unit time dose is changed by changing the X-ray intensity, as illustrated in FIG. 11, the X-ray intensity in the period in which the X-ray generator 42 does not confront the tomographic layer of interest LOI (the state in which the irradiation axis of the X-ray beam BX1 is incident on the tomographic layer of interest LOI in the confronting manner, for example, the projection angles of 0°, 45°, 135° and 180°) is smaller than the X-ray intensity in the period in which the X-ray generator 42 confronts the tomographic layer of interest LOI (when the projection angle is 90°). In the example of FIG. 11, the X-ray intensity is set to I0 at the projection angles between 0° and 45°, and the X-ray intensity is increased from I0 to I1 until the projection angle reaches 90° after passing through about 45°. That is, the X-ray intensity is increased from I0 to I1 until the incident angle ANG1 reaches 90°. The X-ray intensity is decreased from I1 to I0 until the projection angle reaches 135° after exceeding 90°, and the X-ray intensity is maintained at I0 until the projection angle becomes 180°. That is, the X-ray intensity is decreased from I1 to I0 after the incident angle ANG1 exceeds 90°. The dose setting unit 308 generates the dose control data that causes the X-ray generation controller 810 to change the X-ray intensity according to the projection angle in FIG. 11.

The change curve (graph G10) of the X-ray intensity from the increase in the X-ray intensity from I0 to I1 to the decrease in the X-ray intensity again from I1 to I0 has a line symmetrical shape with the axis passing through the projection angle of 90° in the confronting state as a symmetrical axis.

Figure 12:
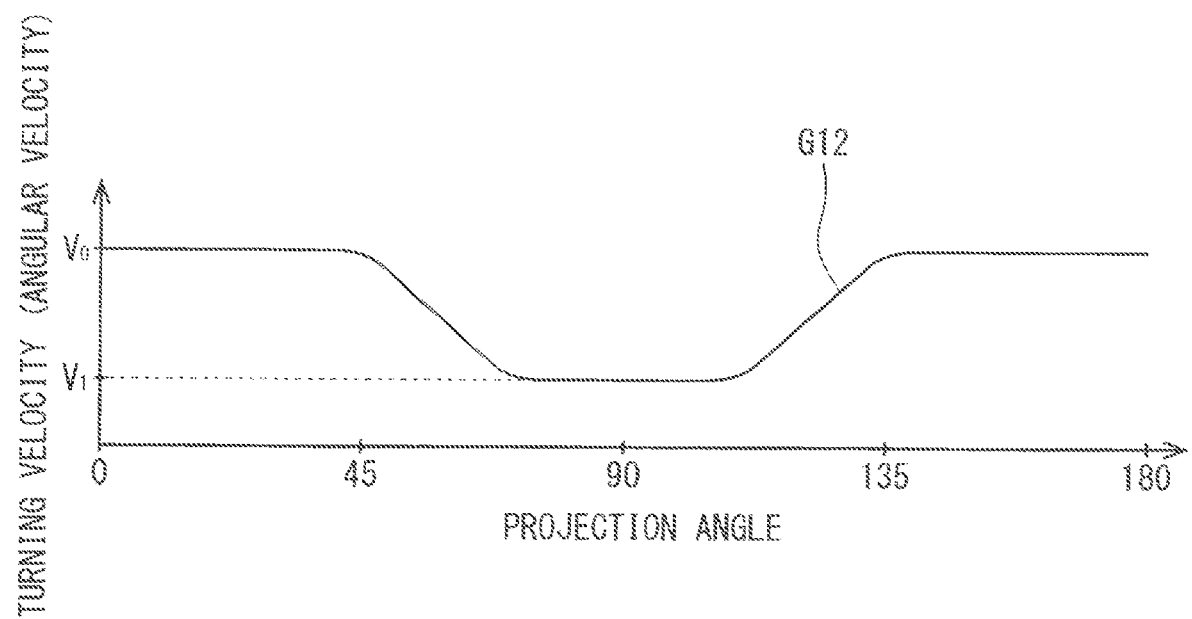
FIG. 12 is a view illustrating a graph G12 of a turning velocity of an X-ray generator 42 corresponding to the projection angle in the CT imaging of FIG. 9.

FIG. 12 is a view illustrating a graph G12 of the turning velocity of the X-ray generator 42 corresponding to the projection angle in the CT imaging of FIG. 9. In FIG. 12, the horizontal axis indicates the projection angle, and the vertical axis indicates the turning velocity (angular velocity). When the unit time dose is changed by changing the turning velocity, as illustrated in FIG. 12, the turning velocity in the period in which the X-ray generator 42 does not confront the tomographic layer of interest LOI (for example, the projection angles of 0°, 45°, 135° and 180°) is smaller than the turning velocity in the period in which the X-ray generator 42 confronts the tomographic layer of interest LOI (when the projection angle is 90°). In the example of FIG. 12, the turning velocity is set to V0 at the projection angles between 0° and 45°, and the turning velocity is decreased from V0 to V1 until the projection angle reaches 90° after passing through about 45°. That is, the turning velocity is decreased from V0 to V1 until the incident angle ANG1 reaches 90°. Then, the turning velocity is increased from V1 to V0 until the projection angle reaches 135° after exceeding 90°, and the X-ray intensity is maintained at V0 until the projection angle becomes 180°. That is, the turning velocity is increased from V1 to V0 after the incident angle ANG1 exceeds 90°. The dose setting unit 308 generates the dose control data for causing the turning movement drive controller 80D, in this case, the turning controller 802, to change the turning velocity according to the projection angle in FIG. 12.

As illustrated in FIG. 12, when the turning velocity is set to V0 at the projection angle of 0°, the X-ray generator 42 starts the turning from the position in front of the position 42p0, and the turning velocity can be increased to V0 until the X-ray generator 42 passes through the position 42p0. The X-ray generator 42 can start the turning from the position 42p0. In this case, the turning velocity can be increased from 0 to V0 until the projection angle becomes from 0° to a predetermined angle.

As illustrated in FIG. 11 or 12, by changing the X-ray intensity or the turning velocity according to the projection angle, the unit time dose in the period in which the X-ray generator 42 does not confront the tomographic layer of interest LOI can be set smaller than the unit time dose in the period in which the X-ray generator 42 confronts the tomographic layer of interest LOI. Consequently, the X-ray projection image can be acquired with high resolution when the tomographic layer of interest LOI is projected from the front surface. Thus, the X-ray tomographic image of the tomographic layer of interest LOI suitable for an image diagnosis can be generated. The X-ray exposure dose of the subject M1 can be decreased by suppressing the unit time dose in the period in which the X-ray generator 42 does not confront the tomographic layer of interest LOI to a low level.

In the embodiment, in order to suppress the X-ray exposure dose of the subject M1, during the X-ray imaging, the unit time dose is lower than that in the conventional CT imaging except for when the X-ray generator 42 confronts the tomographic layer of interest LOI. In order to avoid the noise caused by a decrease in short-time occupation, circuit binning or image processing binning is performed in the X-ray detector 52. When the binning is performed, the resolution can be degraded. For this reason, when the X-ray generator 42 confronts the tomographic layer of interest LOI, the unit time dose is increased but the binning is not performed. By such X-ray imaging, a high-resolution X-ray image of the tomographic layer of interest LOI can be acquired while the X-ray exposure dose of the subject M1 is suppressed.

The unit time dose in the period in which the X-ray generator 42 confronts the tomographic layer of interest LOI can be the same as that in the conventional CT imaging. As a result, the total exposure dose of the subject M1 in the CT imaging can be suppressed to a lower level as compared to the conventional technique.

The unit time dose in the period in which the X-ray generator 42 confronts the tomographic layer of interest LOI can be increased larger than that in the past in order to improve the image quality (resolution) of the tomographic image of the tomographic layer of interest LOI. In this case, preferably the unit time dose in the period in which the X-ray generator 42 does not confront the tomographic layer of interest LOI is decreased such that the total exposure dose of the subject M1 becomes smaller than that in the past.

Hereinafter, setting the unit time dose in the period in which the X-ray generator 42 confronts the tomographic layer of interest LOI larger than the unit time dose in the period in which the X-ray generator 42 does not confront the tomographic layer of interest LOI is the same as setting the unit time dose in the period in which the X-ray generator 42 does not confront the tomographic layer of interest LOI smaller than the unit time dose in the period in which the X-ray generator 42 confronts the tomographic layer of interest LOI.

In the CT imaging of FIG. 9, the turning is started from the position where the incident angle ANG1 becomes 0°. However, the turning is not necessarily started from the position where the incident angle ANG1 becomes 0°. For example, the turning of the X-ray generator 42 can be started from the position where the incident angle ANG1 becomes an angle larger than 0° or the position where the incident angle ANG1 becomes an angle smaller than 0° (the position where the center axis X-ray CBX1 is emitted on the opposite side to the confronting side with respect to the tomographic layer of interest LOI). For example, turning is started from the positions where the X-ray generator 42 is located at the position 42p1 and the X-ray detector 52 is located at the position 52p1, and the positions where the X-ray generator 42 and the X-ray detector 52 turn by 180° can be set to the end position of the turning. Even in this case, the unit time dose in the period in which the X-ray generator 42 confronts the tomographic layer of interest LOI, namely, in the period in which the X-ray generator 42 is located at the position 42p2 is similarly increased larger than the unit time dose in the period in which the X-ray generator 42 does not confront the tomographic layer of interest LOI. Alternatively, the rotation of the X-ray generator 42 can be started from the near side in the rotational direction with respect to the position 42p0, and the emission of the X-ray beam BX1 can be started after the X-ray generator 42 reaches the position 42p0.

At this point, a range that is not so close to the right angle as the substantially right angle, but is close to the right angle is referred to as a "near right angle". Incidence in which the incident angles are the near right angle can be referred to as "near orthogonal incidence".

At the substantially right angles, a range of a difference on the small side or the large side with respect to the orthogonal state is set to an angle Iao. For example, the angle Iao is 5° when the substantially right angle ranges from 90°−5° to 90°+5°.

The range of the near right angle can be defined in various ways, for example, 90°−30° to 90°−angle Iao, 90°+angle Iao to 90°+30°, 90°−15° to 90°−angle Iao, and 90°+angle Iao to 90°+15°.

The period during which the X-ray intensity is maintained at intensity I1 in FIG. 11 and the period during which the turning velocity is maintained at velocity V1 in FIG. 12 can have a width. Alternatively, the pattern can be changed. For example, the following control can be considered. At least setting the X-ray intensity to the intensity I1 at the orthogonal timing, and/or setting the turning velocity to velocity V1, and setting the X-ray strength to the strength lower than the strength I1 at at least a part of the period that is out of the orthogonal timing, and/or setting the turning velocity to the velocity higher than the velocity V1 are common. These variations can also be applied to tomosynthesis imaging (to be described later).

In the following description, the X-ray intensity between the X-ray intensities I0 and I1 is set to intensity IM, and the turning velocity between the turning velocities V0 and V1 is set to velocity VM. The control that changes the X-ray intensity or the turning velocity in the following manner can be assumed.

(a) Control in which the X-ray intensity in the period of the near right angle period is set to the intensity IM and the X-ray intensity is maintained at the intensity I1 in the substantially right angle period, and/or control in which the turning velocity in the near right angle period is set to the velocity VM and the turning velocity is maintained at the velocity V1 in the substantially right angle period.

(b) Further, in the control (a), control in which the X-ray intensity is maintained at the intensity I1 in the range close to the substantially right angle in the near right angle, and/or control in which the turning velocity is maintained at the velocity V1 in the range close to the substantially right angle in the near right angle.

(c) In the control (a), control in which the X-ray intensity is set to the peak intensity I1 only at the right angle timing in the substantially right angle period and the X-ray intensity is set to the intensity higher than the intensity IM and lower than the intensity I1 in the period before and after the right angle in the substantially right angle period, and/or control in which the turning velocity is set to the peak velocity V1 only at the right angle timing in the substantially right angle period and the turning velocity is set to the velocity lower than the velocity VM and higher than the velocity V1 in the period before and after the right angle in the substantially right angle period.

(d) Further, in the control (c), control in which the X-ray intensity is set to the intensity higher than the intensity IM and lower than the intensity I1 in the range near the substantially right angle in the near right angle period, and/or control in which the turning velocity is set to the velocity lower than the velocity VM and higher than the velocity V1 in the range near the substantially right angle in the near right angle period.

(e) Control in which the X-ray intensity is maintained at the intensity I1 only in the substantially right angle period and the X-ray intensity is uniformly maintained at the intensity I0 in other periods, and/or control in which the turning velocity is maintained at the velocity V1 only in the substantially right angle period and the turning velocity is maintained at the velocity V0 in other periods.

(f) In the control (e), control in which an inclination of the change in the turning velocity is made steep or gentle between the substantially right angle period and other periods.

(g) Control in which the X-ray intensity is set to the peak intensity I1 only at the right angle timing and uniformly maintained at the intensity I0 in other periods, and/or control in which the turning velocity is set to the peak velocity V1 only at the right angle timing and uniformly maintained at the velocity V0 in other periods.

(h) In the control (g), control in which the inclination of the change in the X-ray intensity and/or the inclination of the change in the turning velocity is made steep or gentle between the right angle timing and other periods.

Figure 13:
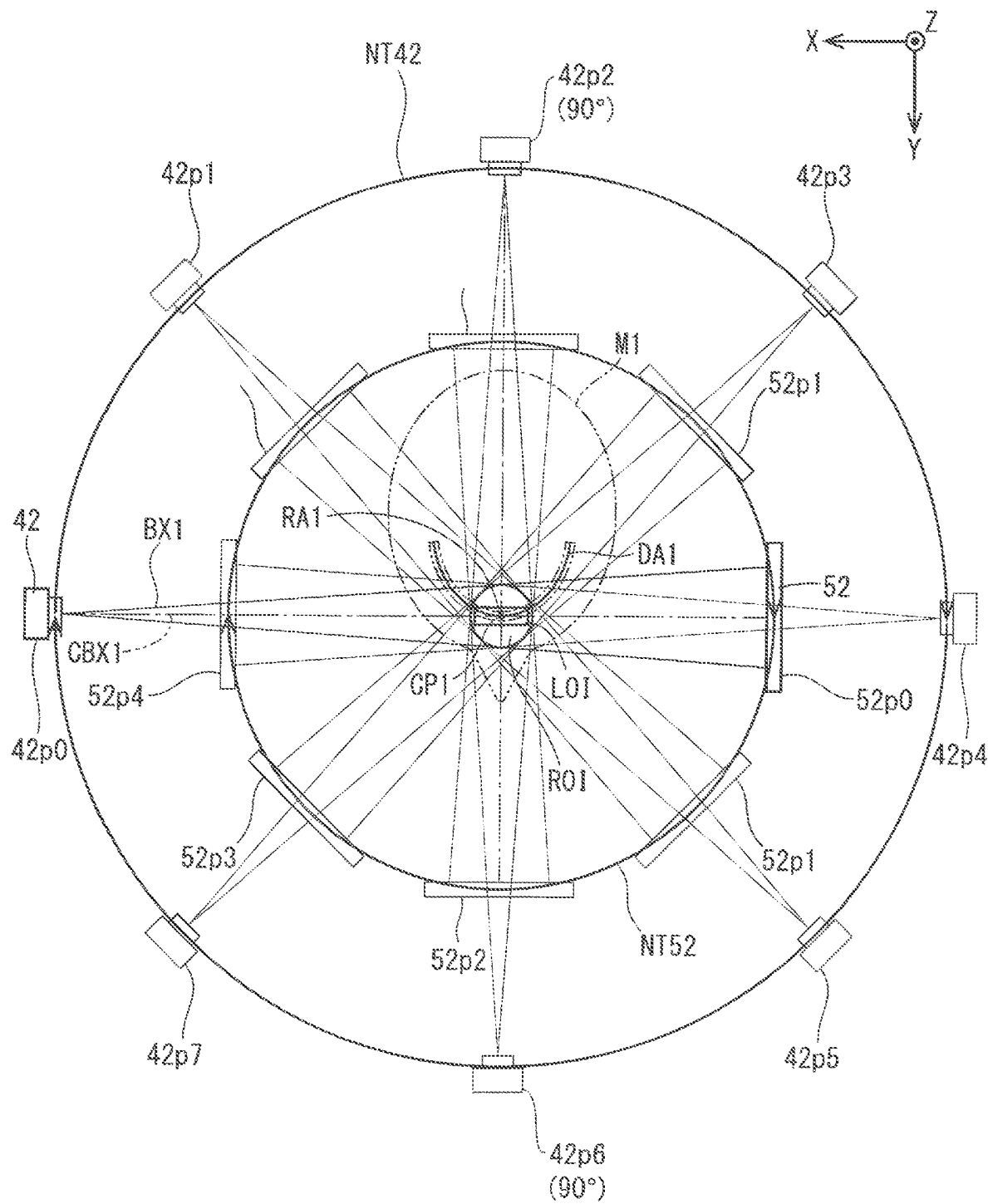
FIG. 13 is a view illustrating an example of the X-ray tomography.

FIG. 13 is a view illustrating an example of the X-ray tomography. The X-ray tomography in FIG. 13 is the CT imaging in which the X-ray generator 42 and the X-ray detector 52 are turned by 360° around the subject M1. The imaging region ROI and the tomographic layer of interest LOI in the CT imaging are the same as the CT imaging illustrated in FIG. 9.

In the CT imaging, the X-ray generator 42 is turned from a position 42p0 on the right side of the head to a position 42p4 on the left side of the head through a position 42p1 to a position 42p3 on a rear side of the head. The X-ray generator 42 passes from the position 42p4 while turning from the position 42p5 to the position 42p7 on the front side of the head, and returns again to the position 42p0. The X-ray detector 52 is turned from the position 52p0 on the left side of the head to the position 52p4 on the right side of the head through the position 52p1 to the position 52p3 on the front side of the head. The X-ray detector 52 passes from the position 52p4 while turning from the position 52p5 to the position 52p7 on the front side of the head, and returns again to the position 52p0. The normal imaging trajectory NT42 of the X-ray generator 42 and the normal imaging trajectory NT52 of the X-ray detector 52 are matched with a circumference having a predetermined radius centered on the center point CP1 of the imaging region ROI.

For the CT imaging, the X-ray generator 42 confronts the tomographic layer of interest LOI twice. The first time is when the X-ray generator 42 is located at the position 42p2 (when the projection angle is 90°), and the second time is when the X-ray generator 42 is located at the position 42p6 (when the projection angle is 270°). The dose setting unit 308 generates the dose control data for operating the X-ray generation controller 810 or the turning controller 802 such that the unit time dose increases when the X-ray generator 42 passes through the positions 42p2, 42p6.

Figure 14:
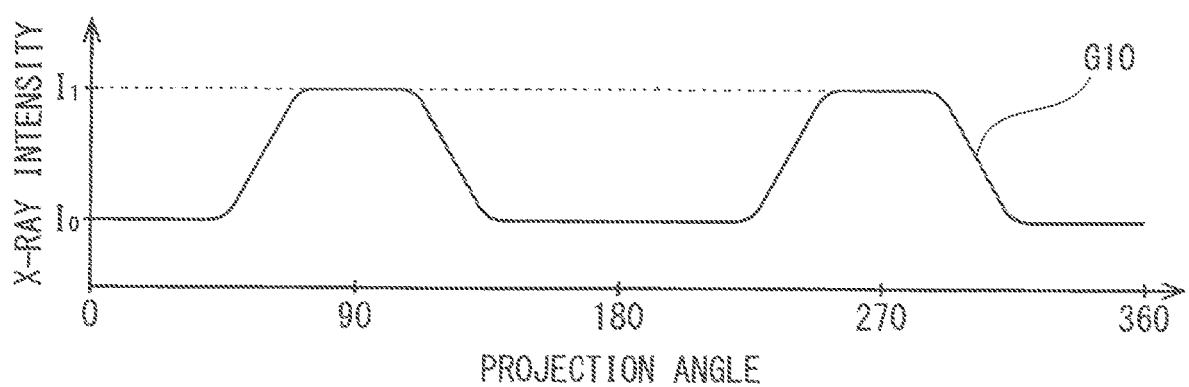
FIG. 14 is a view illustrating the graph G10 of the X-ray intensity corresponding to the projection angle in the CT imaging of FIG. 13.

FIG. 14 is a view illustrating the graph G10 of the X-ray intensity corresponding to the projection angle in the CT imaging of FIG. 13. In FIG. 14, a horizontal axis indicates the projection angle, and a vertical axis indicates the X-ray intensity. When the unit time dose is changed by changing the X-ray intensity, as illustrated in FIG. 14, preferably the X-ray intensity is set to I0 when the X-ray generator 42 does not confront the tomographic layer of interest LOI, and the X-ray intensity is set to I1 larger than I0 when the X-ray generator 42 confronts the tomographic layer of interest LOI. In the CT imaging of FIG. 13, the X-ray intensity is set to I1 at the projection angles of 90° and 270°.

Specifically, in the graph G10 of FIG. 14, the X-ray intensity is increased from I0 to I1 until the projection angle reaches 90° after passing through about 45°, and the X-ray intensity is decreased from I1 to I0 until the projection angle reaches 180° after passing through 90°. The X-ray intensity is increased from I0 to I1 until the projection angle reaches 270° after passing through 180°, and the X-ray intensity is decreased from I1 to I0 until the projection angle reaches 360° after passing through 270°.

Figure 15:
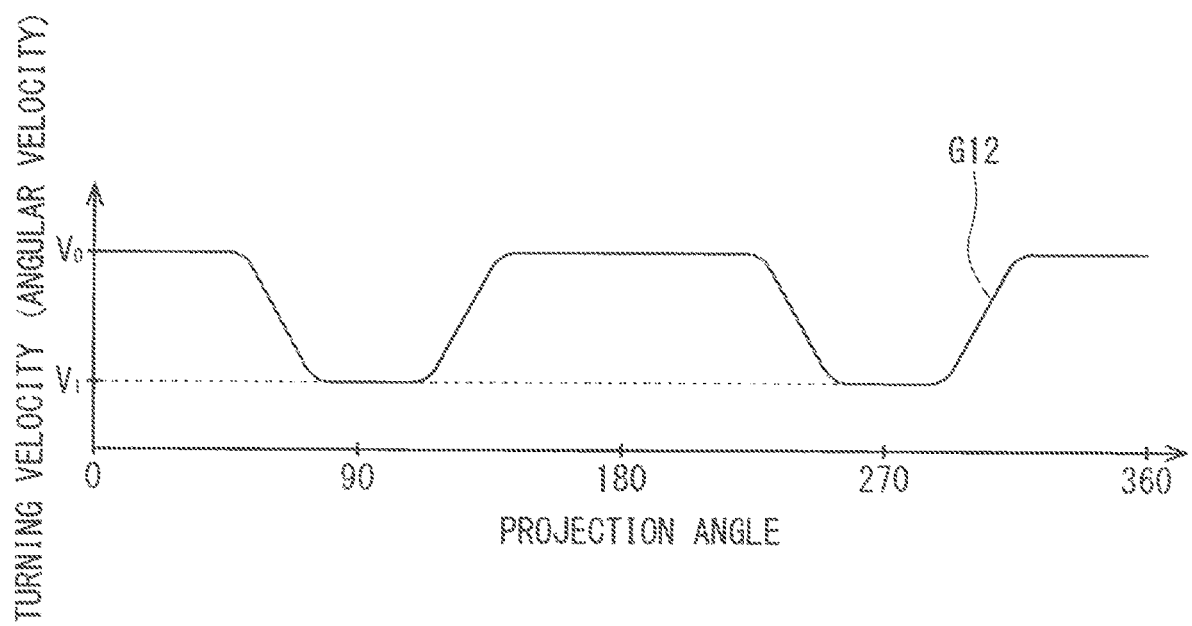
FIG. 15 is a view illustrating the graph G12 of the turning velocity corresponding to the projection angle in the CT imaging of FIG. 13.

FIG. 15 is a view illustrating the graph G12 of the turning velocity corresponding to the projection angle in the CT imaging of FIG. 13. In FIG. 15, the horizontal axis indicates the projection angle, and the vertical axis indicates the turning velocity (angular velocity). When the unit time dose is changed by changing the turning velocity, as illustrated in FIG. 15, preferably the turning velocity is set to V0 in the period in which the X-ray generator 42 does not confront the tomographic layer of interest LOI, and the turning velocity is set to V1 larger than I0 in the period in which the X-ray generator 42 confronts the tomographic layer of interest LOI.

Specifically, in the graph G12 of FIG. 15, the turning velocity is increased from V0 to V1 until the projection angle reaches 90° after passing through about 45°, and the turning velocity is decreased from V1 to V0 until the projection angle reaches 180° after passing through 90°. The turning velocity is increased from V0 to V1 until the projection angle reaches 270° after passing through 180°, and the turning velocity is decreased from V1 to V0 until the projection angle reaches 360° after passing through 270°.

As illustrated in FIG. 14 or 15, by changing the X-ray intensity or the turning velocity according to the projection angle, the unit time dose in the period in which the X-ray generator 42 confronts the tomographic layer of interest LOI can be set larger than the unit time dose in the period in which the X-ray generator 42 does not confront the tomographic layer of interest LOI. Consequently, the resolution of the X-ray projection image obtained in the confronting state can be improved. Thus, the tomographic layer of interest LOI suitable for the image diagnosis can be acquired. The unit time dose is increased while limiting to a part of the projection angle, so that the X-ray exposure dose of the subject M1 can be suppressed.

Figure 16:
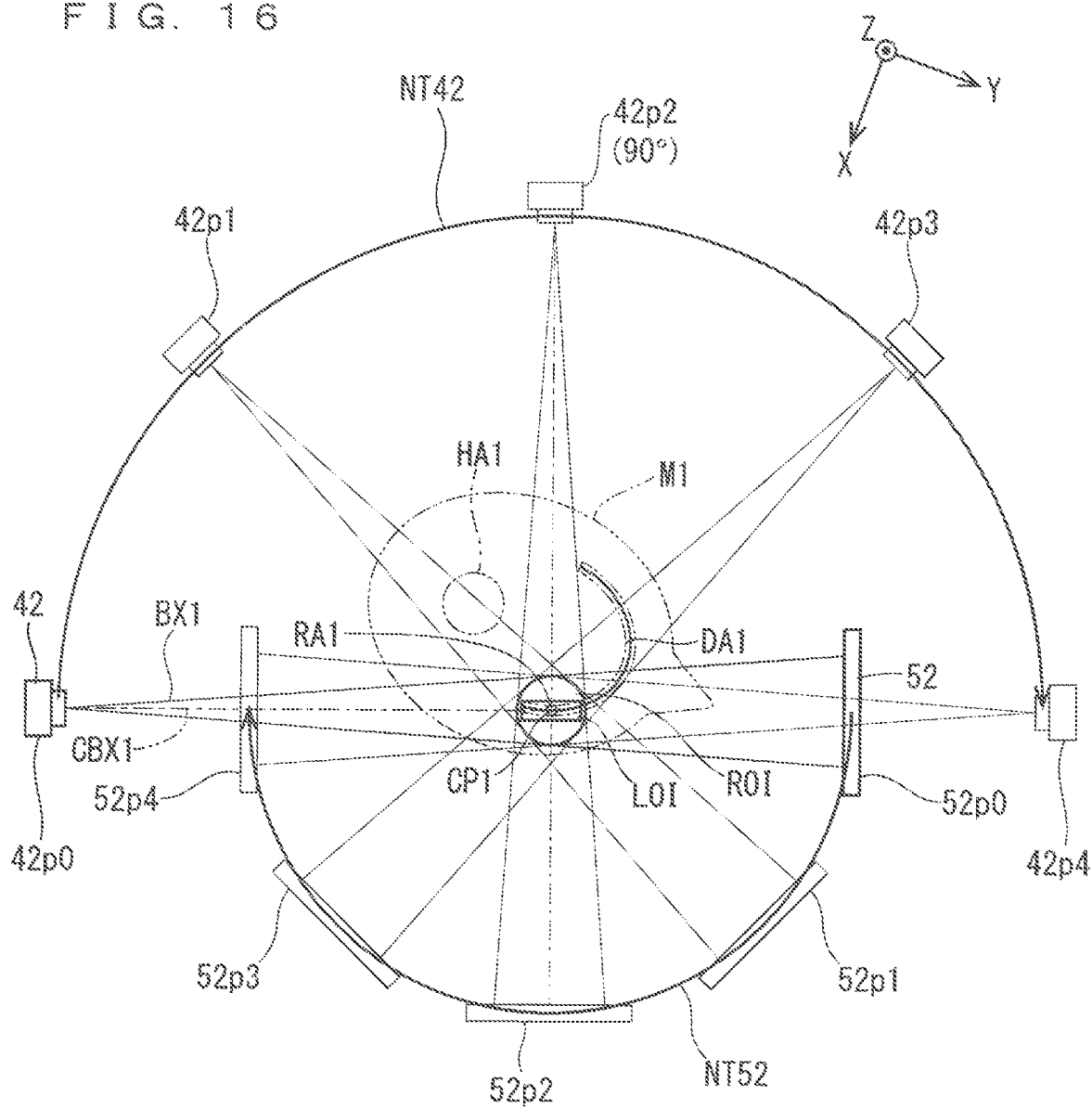
FIG. 16 is a view illustrating an example of the X-ray tomography.

FIG. 16 is a view illustrating an example of the X-ray tomography. The X-ray tomography in FIG. 16 is the CT imaging in which the X-ray generator 42 and the X-ray detector 52 are turned by 180° around the subject M1. A portion including a right molar in the jaw of the subject M1 is set to the imaging region ROI, and a region extending linearly along a direction parallel to the tangential line of a part of the dental arch DA1 included in the imaging region ROI is set to the tomographic layer of interest LOI.

In the CT imaging, the X-ray generator 42 is turned from the position 42p0 on the right rear side of the head of the subject M1 to the position 42p4 on the left rear side of the head through the positions 42p1 to 42p3 on the left side of the head. The X-ray detector 52 turns from the position 52p0 on the front left side of the head of the subject M1 to the position 52p4 on the rear right side of the head through the positions 52p1 to 52p3 on the right side of the head.

As illustrated in FIG. 16, in the CT imaging, the state occurs in which a part or a whole of the X-ray beam BX1 passes through a cervical spine that is a high X-ray absorption site HA1 while the X-ray generator 42 turns. Specifically, when the X-ray generator 42 passes through the position 42p1, the X-ray beam BX1 passes through the high X-ray absorption site HA1. When the X-ray beam BX1 passes through the high X-ray absorption site HA1 as described above, it may be difficult to obtain accurate information about the imaging region ROI because the X-ray is significantly attenuated.

For this reason, the dose setting unit 308 can generate the dose control data for making the unit time dose when the high X-ray absorption site HA1 exists on a path of the X-ray beam BX1 larger than the unit time dose when the high X-ray absorption site HA1 does not exist.

Figure 17:
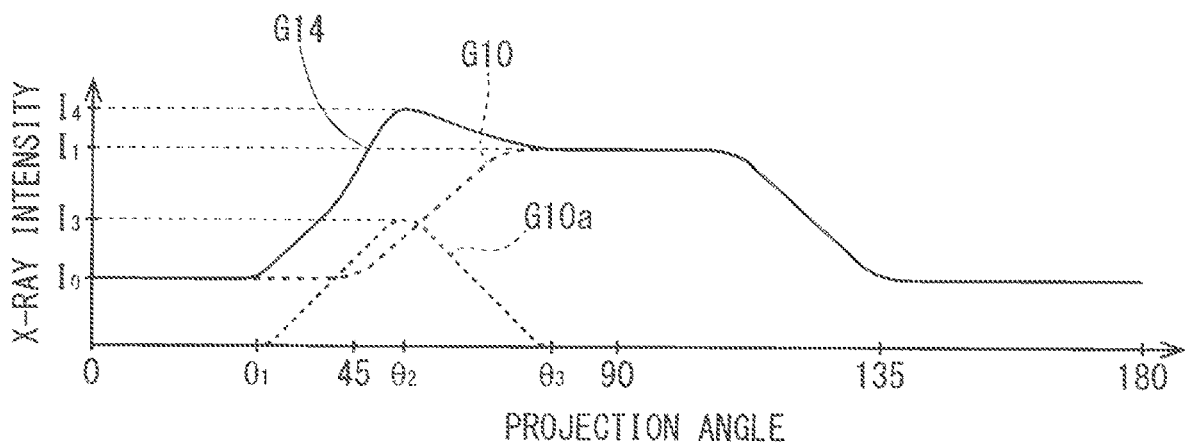
FIG. 17 is a view illustrating a graph G14 of the X-ray intensity in the CT imaging of FIG. 16.

FIG. 17 is a view illustrating a graph G14 of the X-ray intensity in the CT imaging of FIG. 16. When the unit time dose is changed by changing the X-ray intensity, the dose setting unit 308 can create the dose control data for changing the X-ray intensity according to the projection angle as illustrated by the graph G14.

The graph G14 is obtained by adding a graph G10a to the graph G10. The graph G10 is a curve indicating the X-ray intensity when the unit time dose is increased in the period in which the X-ray generator 42 confronts the tomographic layer of interest LOI. In the graph G10, the X-ray intensity is set to I0 at the projection angle at which the X-ray generator 42 does not confront the tomographic layer of interest LOI, and the X-ray intensity is set to I1 (>I0) at the projection angle (90°) at which the X-ray generator 42 confronts the tomographic layer of interest LOI.

The graph G10a is a curve indicating the amount of X-ray intensity increasing the unit time dose in order to reduce the influence of the high X-ray absorption site HA1. As illustrated in the graph G10a, in order to reduce the influence of the high X-ray absorption site HA1, the increase in the X-ray intensity is started from a projection angle θ1 (in this case, 0°<θ1<45°) at which the X-ray beam BX1 starts to overlap the high X-ray absorption site HA1. The X-ray intensity is increased by I3 at a projection angle θ2 (in this case, 45°<θ2<90°) at which the overlap between the X-ray beam BX1 and the high X-ray absorption site HA1 becomes the maximum. Subsequently, the X-ray intensity is gradually decreased to a projection angle θ3 (θ2<θ3<90°) at which the overlap between the X-ray beam BX1 and the high X-ray absorption site HA1 disappears.

The X-ray intensity increases in both of the graph G10 and the graph 10a until the projection angle becomes θ2 after passing through 45°. For this reason, in the graph G14, the X-ray intensity starts to increase from I0 when the projection angle is θ1, and the X-ray intensity becomes I4 at the projection angle θ2. The X-ray intensity I4 is larger than the X-ray intensity I1 in the period in which the X-ray generator 42 confronts the tomographic layer of interest LOI.

The dose setting unit 308 generates the dose control data for changing the X-ray intensity as indicated by the graph G14, whereby the resolution of the X-ray projection image can be improved when the X-ray generator 42 confronts the tomographic layer of interest LOI, and the influence of the high X-ray absorption site HA1 can be reduced.

For example, position information about the high X-ray absorption site HA1 can previously be stored in the storage 31. In this case, the dose setting unit 308 can preferably read the position information about the high X-ray absorption site HA1 corresponding to a physical feature of the subject M1. That is, by previously preparing the positional information about the high X-ray absorption site HA1 in each physical feature of the subject M1, the X-ray tomography can be performed so as to reduce the influence of the high X-ray absorption site HA1 according to the subject M1. The operator can designate the position of the high X-ray absorption site HA1. For example, the X-ray projection image (transmission image) obtained by previously performing the X-ray tomography of the subject M1 is displayed on the display 32 or the like, and the operator can select the high X-ray absorption site HA1 on the X-ray projection image. In this case, the highly accurate position information about the high X-ray absorption site HA1 can be acquired according to the individual subject M1. Thus, the influence of the high X-ray absorption site HA1 can accurately be reduced.

In the X-ray tomography of FIGS. 11, 12, 14, and 15, the unit time dose is set to the maximum when the X-ray generator 42 confronts the tomographic layer of interest LOI. However, for example, as illustrated in FIG. 17, the unit time dose can be larger than that in the period in which the X-ray generator 42 confronts the tomographic layer of interest LOI in a part of the period in which the X-ray generator does not confront the tomographic layer of interest LOI. That is, the unit time dose in the period in which the X-ray generator 42 confronts the tomographic layer of interest LOI can be larger than the unit time dose in at least a part of the period in which the X-ray generator 42 does not confront the tomographic layer of interest LOI.

The examples of FIGS. 9 and 13 does not mention the high X-ray absorption site HA1 for the sake of easy understanding. However, also in the examples of FIGS. 9 and 13, the influence of the high X-ray absorption site HA1 can be reduced.

Specifically, in the example of FIG. 9, the high X-ray absorption site HA1 (cervical spine) can overlap the path of the X-ray beam BX1 at the timing when the X-ray generator 42 is located at the position 42p2. For this reason, the unit time X-ray dose is preferably increased at the timing when the X-ray generator 42 is located at the position 42p2. When the unit time X-ray dose is increased by changing the X-ray intensity, the X-ray intensity at the projection angle of 90° can be further increased larger than I1 in the graph G10 of FIG. 11. When the unit time X-ray dose is increased by changing the turning angle, the turning velocity at the projection angle of 90° can further be decreased lower than V1 in the graph G12 of FIG. 12.

In the example of FIG. 13, the high X-ray absorption site HA1 (cervical spine) can overlap the path of the X-ray beam BX1 at the timing when the X-ray generator 42 is located at the position 42p2 and the timing when the X-ray generator 42 is located at the position 42p6. For this reason, the unit time X dose is preferably increased at these timings.

Imaging Trajectory That Decreases Projection Magnification Factor

Figure 18:
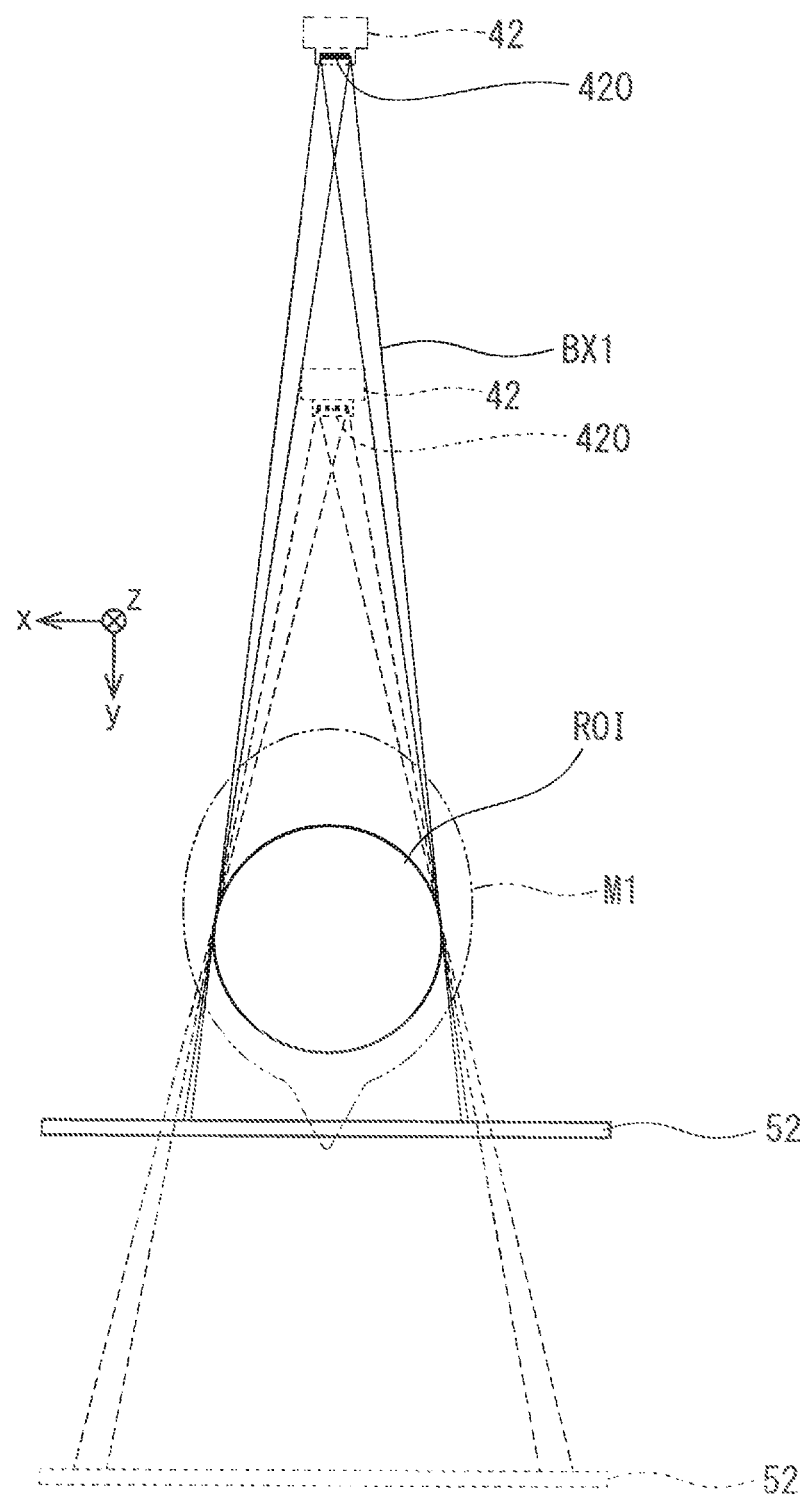
FIG. 18 is a view illustrating a relationship between a magnification factor and resolution in an X-ray projection image.

FIG. 18 is a view illustrating a relationship between a magnification factor and the resolution in the X-ray projection image. FIG. 18 schematically illustrates the X-ray generator 42 and the X-ray detector 52 when viewed from the +Z-side (in −Z-direction view). As illustrated in FIG. 18, the X-ray beam BX1 spreading in a fan shape is emitted from the X-ray tube of the X-ray generator 42. For this reason, the imaging region ROI is enlarged and projected onto the X-ray detector 52. Because the imaging region ROI is transmitted through the X-ray beam BX1, the magnification factor of the X-ray projection image (hereinafter, referred to as a "projection magnification factor") projected onto the X-ray detector 52 is determined by a distance from the X-ray generator 42 to the imaging region ROI and a distance from the imaging region ROI to the X-ray detector 52. In FIG. 18, when the X-ray generator 42 and the X-ray detector 52 move from the position indicated by the broken line to the position indicated by the solid line, the X-ray generator 42 moves away from the imaging region ROI, and the X-ray detector 52 approaches the imaging region ROI. This decreases the projection magnification factor. The X-ray detector 52 indicated by the solid line is drawn so as to overlap the nose of the subject M1. This is because the X-ray detector 52 is emphasized for the purpose of explanation of an approach and moving away principle.

In the X-ray detector 52, many detection elements are arrayed in the detection surface. Thus, the resolving power of the X-ray detector 52 is fixed, so that the resolution of the X-ray projection image can be improved by increasing the projection magnification factor. However, a focal point of the X-ray beam BX1 emitted from the X-ray generator 42 is not a point strictly, but a focal plane 420 having a certain size. An anode (focal plane 420) of the actual X-ray tube is inclined with respect to an X-ray irradiation axis. However, for convenience of illustration, in order to indicate that the focal plane 420 is not a point in principle, the anode is illustrated so as to be perpendicular to the X-ray irradiation axis. When attention is paid to a specific point of the imaging region ROI, an X-ray flux passing through the specific point in the X-ray beam BX1 emitted from the focal plane 420 is projected onto the detection surface of the X-ray detector 52 with constant spread. That is, the X-ray beam BX1 emitted from the focal plane 420 causes blurring on the X-ray projection image. When the projection magnification factor increases, a degree of blurring also increases, and resultantly the resolution (sharpness) of the X-ray projection image decreases.

Thus, in order to improve the resolution of the X-ray projection image, the projection magnification factor is desirably decreased as much as possible. For this reason, during the X-ray tomography, desirably, the X-ray detector 52 is caused to approach the imaging region ROI as much as possible, or the X-ray generator 42 is moved away from the imaging region ROI as much as possible.

However, when the X-ray detector 52 is caused to approach the imaging region ROI, the X-ray detector 52 can come into contact with the subject M1. When the X-ray generator 42 is moved away from the imaging region ROI, there is a possibility that the X-ray generation unit 40 accommodating the X-ray generator 42 collides with another member (for example, the post 70) of the imaging unit 20 or another member other than the imaging unit 20 disposed in the periphery.

The imaging trajectory setting unit 306 prevents the X-ray detector 52 from contacting with the subject M1 during the X-ray tomography, and sets the imaging trajectory so as to decrease the projection magnification factor as much as possible while preventing the X-ray generation unit 40 of the X-ray generator 42 from colliding with another member. A specific method for setting the imaging trajectory will be described below.

Figure 19:
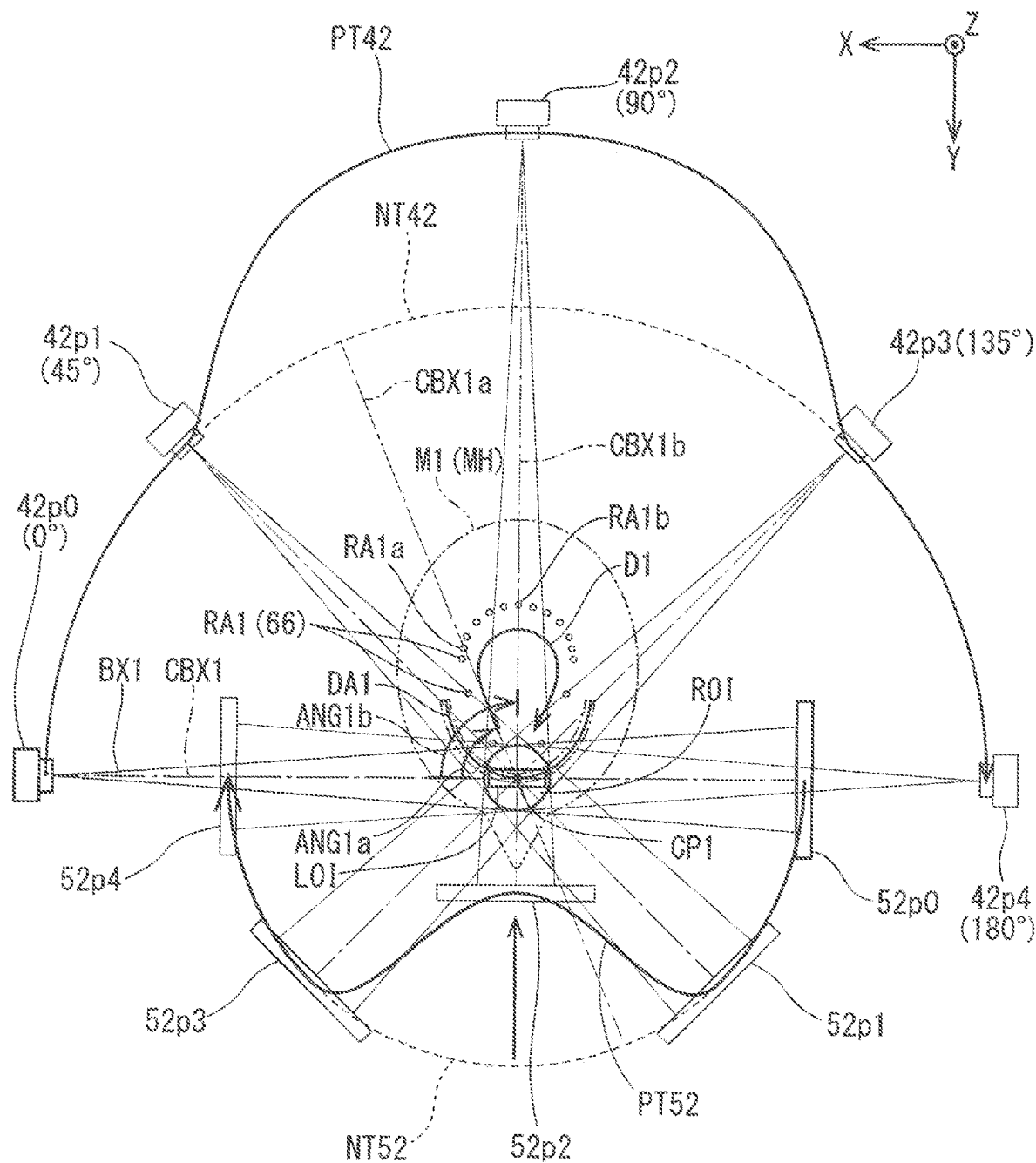
FIG. 19 is a view illustrating an example of the X-ray tomography.

FIG. 19 is a view illustrating an example of the X-ray tomography. The X-ray tomography in FIG. 19 is the CT imaging in which the X-ray generator 42 and the X-ray detector 52 are turned by 180° around the jaw of the subject M1. At this point, the vicinity of the front teeth of the subject M1 is set to the imaging region ROI, and the tomographic layer of interest LOI is set to a linear region along the dental arch DA1.

In the CT imaging, the X-ray generator 42 is turned by 180° from a position 42p0 on the right side of the head of the subject M1 to a position 42p4 on the left side of the head after passing through a rear side of the head. The X-ray detector 52 passes through a front side of the head from a position 52p0 on the left side of the head of the subject M1, and is turned by 180° to a position 52p4 on the right side of the head. In the CT imaging, the imaging conditions and the like are matched with the CT imaging of FIG. 9 except that this CT imaging differs from the CT imaging of FIG. 9 in the imaging trajectories of the X-ray generator 42 and the X-ray detector 52.

In the normal CT imaging in which the projection magnification factor is not changed, each of the X-ray generator 42 and the X-ray detector 52 is rotated at a constant rotation radius around a center point CP1 of the imaging region ROI. That is, in the normal CT imaging, the X-ray generator 42 and the X-ray detector 52 are moved on the normal imaging trajectories NT42, NT52. The X-ray generator 42 follows the normal imaging trajectory NT42, and the X-ray detector 52 follows the normal imaging trajectory NT52.

On the other hand, in the CT imaging of the embodiment, the imaging trajectory setting unit 306 sets imaging trajectories PT42, PT52 in which the projection magnification factor in the period in which the imaging trajectory setting unit 306 confronts the tomographic layer of interest LOI in the imaging region ROI is smaller than that in the period in which the imaging trajectory setting unit 306 does not confront the tomographic layer of interest LOI. More specifically, when the X-ray generator 42 confronts the tomographic layer of interest LOI, as compared with the non-confrontation, the X-ray generator 42 is moved farther away from the tomographic layer of interest LOI, and the X-ray detector 52 is caused to approach the tomographic layer of interest LOI. The imaging trajectories PT42, PT52 are referred to as a magnification factor adjustment imaging trajectory, the X-ray generator 42 follows the magnification factor adjustment imaging trajectory PT42, and the X-ray detector 52 follows the magnification factor adjustment imaging trajectory PT52. The CT imaging with the magnification factor adjustment imaging trajectories PT42, PT52 is referred to as magnification factor adjustment CT imaging.

In the CT imaging of FIG. 19, on the magnification factor adjustment imaging trajectory PT42, each of the positions 42p0 to 42p4 of the X-ray generator 42 is the position of the X-ray generator 42 where the incident angle ANG1 becomes 0°, 45°, 90°, 135°, and 180°. That is, the position where the X-ray generator 42 confronts the tomographic layer of interest LOI (the position where the irradiation axis of the X-ray beam BX1 is incident on the tomographic layer of interest LOI in the confronting manner) becomes the position 42p2. The position where the X-ray generator 42 does not confront the tomographic layer of interest LOI (the position where the irradiation axis of the X-ray beam BX1 is not incident on the tomographic layer of interest LOI in the confronting manner) becomes positions 42p0, 42p1, 42p3, 42p4. At this point, when the position 42p2 in the confronting state is compared to the positions 42p0, 42p1, 42p3, 42p4 in the non-confronting state, the position 42p2 is a position farther from the tomographic layer of interest LOI than the other positions 42p0, 42p1, 42p3, 42p4. That is, the position 42p2 is set outside the normal imaging trajectory NT42 of the X-ray generator 42. The position 52p2 of the X-ray detector 52 in the confronting state is closer to the tomographic layer of interest LOI than the positions 52p0, 52p1, 52p3, 52p4 in the non-confronting state. The position 52p2 is set outside the normal imaging trajectory NT52 of the X-ray detector 52.

In the CT imaging, until the X-ray generator 42 reaches the position 42p2 of the confronting state after passing through the position 42p1 where the incident angle ANG1 becomes 45°, the X-ray generator 42 is gradually moved away from the tomographic layer of interest LOI, and the X-ray detector 52 is gradually caused to approach the tomographic layer of interest LOI. Until the X-ray generator 42 reaches the position 42p3 where the incident angle ANG1 becomes 135° from the position 42p2 of the confronting state, the X-ray generator 42 is gradually caused to approach the tomographic layer of interest LOI, and the line X-ray detector 52 is gradually moved away from the tomographic layer of interest LOI. That is, in the imaging trajectory PT42 of the X-ray generator 42, the position 42p1 to the position 42p3 are different from those of the normal imaging trajectory NT42, and other positions are matched. Similarly, in the imaging trajectory PT52 of the X-ray detector 52, the position 52p1 to the position 52p3 are different from those of the normal imaging trajectory NT52, and other positions are matched.

Figure 20:
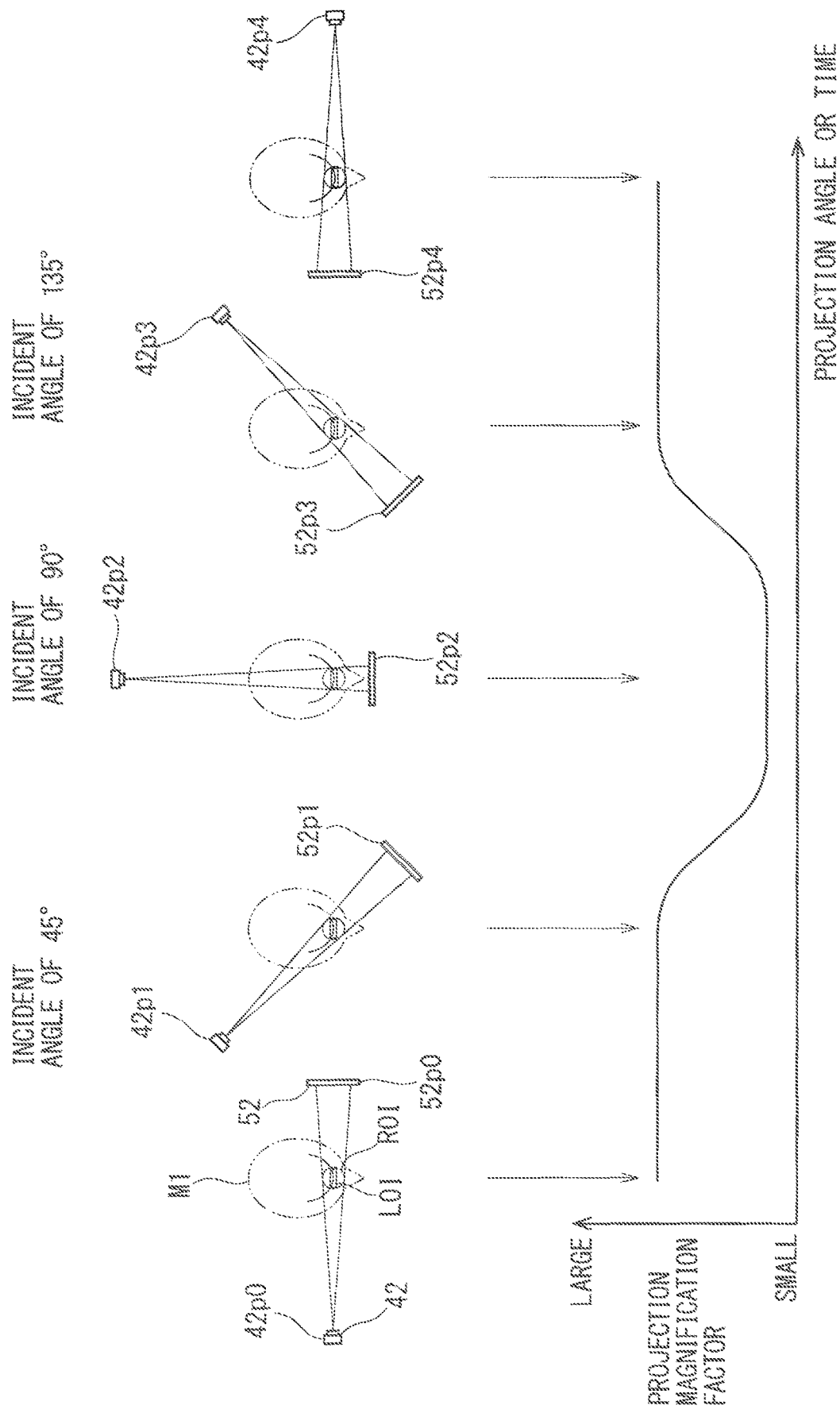
FIG. 20 is a view illustrating a fluctuation in a projection magnification factor corresponding to the projection angle.

FIG. 20 is a view illustrating a fluctuation in the projection magnification factor corresponding to the projection angle. By setting the imaging trajectories PT42, PT52 as described above, as illustrated in FIG. 20, the projection magnification factor is kept constant until the incident angle ANG1 reaches 45°, and the projection magnification factor decreases gradually until the incident angle ANG1 becomes 90° after exceeding 45°. The projection magnification factor is minimized when the incident angle ANG1 is 90°. The projection magnification factor increases gradually until the incident angle ANG1 reaches 135° after the incident angle ANG1 exceeds 90°, and the projection magnification factor is kept constant after the incident angle ANG1 exceeds 135°. That is, the magnification factor decreased in the confronting state when the state in which the X-ray generator 42 confronts the tomographic layer of interest LOI (when the X-ray generator 42 is located at the position 42p2) and the state in which the X-ray generator 42 does not confront the tomographic layer of interest LOI (for example, when the X-ray generator 42 is located at the positions 42p0, 42p1, 42p3, 42p4) are compared to each other.

The magnification factor can be minimized only when the incident angle ANG1 is 90°. Alternatively, the minimized magnification factor can have a width. That is, the magnification factor can be maintained at the same minimum magnitude for a certain period from the timing at which the incident angle ANG1 is slightly less than 90°, through the timing at which the incident angle ANG1 is exactly 90°, and to the timing at which the incident angle ANG1 slightly exceeds 90°.

As described above, the imaging trajectory setting unit 306 sets the imaging trajectories PT42, PT52 of the X-ray generator 42 and the X-ray detector 52. The imaging controller 80 moves the X-ray generator 42 and the X-ray detector 52 along the imaging trajectories PT42, PT52 by controlling the operations of the turning drive unit 642 and the XY-direction movement drive unit 644. That is, the imaging controller 80 controls the XY-direction movement drive unit 644 according to the incident angle ANG1 while changing the incident angle ANG1 by controlling the operation of the turning drive unit 642. Consequently, the imaging controller 80 relatively decreases the projection magnification factor in the confronting state when the confronting state and the non-confronting state are compared to each other.

At this point, attention is paid to the turning center axis RA1 that is the turning center of the X-ray generator 42 and the X-ray detector 52. While the X-ray generator 42 moves from the position 42p0 to the position 42p1, and while the X-ray generator 42 moves from the position 42p3 to the position 42p4, the turning center axis RA1 is set to the center point CP1. On the other hand, while the X-ray generator 42 moves from the position 42p1 to the position 42p3, as indicated by an arrow D1 in FIG. 10, the X-ray generator 42 moves on a circular trajectory in which the X-ray generator 42 moves away from the center point CP1 and returns to the center point CP1.

When the shaft 66 that rotates the turning arm 62 is matched with the turning center axis RA1, the X-ray generator 42 and the X-ray detector 52 can be moved on the imaging trajectories PT42, PT52 by moving the shaft 66 on the trajectory of the turning center axis RA1 in FIG. 10. The shaft 66 is not necessarily matched with the turning center axis RA1. For example, the technique described in Japanese Patent Application Laid-Open No. 2007-29168 can also be applied to the present application. That is, while the shaft 66 is rotated, the shaft 66 is moved along a circumference of a predetermined radius centered on the center point CP1 of the imaging region ROI in the XY-plane. Consequently, the X-ray generator 42 and the X-ray detector 52 can be turned around the turning center axis RA1 matched with the center point CP1. In this case, the turning center axis RA1 is set at a position different from the shaft 66 that is the mechanical turning axis.

In the embodiment, the rotational movement and the movement in the XY-plane of the X-ray generator 42 and the X-ray detector 52 are performed by the rotation about the Z-axis of the shaft 66 of the turning arm 62 and the movement in the XY-plane. Thus, the setting of the imaging trajectories PT42, PT52 of the X-ray generator 42 and the X-ray detector 52 is equivalent to the setting of the position in the XY-plane of the shaft 66 according to the rotation amount of the shaft 66.

The description of the movement of the turning center axis RA1 will be further supplemented. The turning center axis RA1 moves as the rotation center at any time while the X-ray generator 42 and the X-ray detector 52 move along the magnification factor adjustment imaging trajectories PT42, PT52. In the normal CT imaging, an incident angle at which the incident angle ANG1 is an intermediate angle between 45° and 90° is set to an incident angle ANG1*a*, and an incident angle at which the incident angle ANG1 is 90° is set to an incident angle ANG1*b*. The center axis X-ray CBX1 at the incident angle ANG1*a* is set to a center axis X-ray CBX1A (not illustrated), and the center axis X-ray CBX1 at the incident angle ANG1*b* is set to a center axis X-ray CBX1B (not illustrated).

In the magnification factor adjustment CT imaging, as described above, because the turning center axis RA1 moves as the rotation center at any time, the position of the turning center axis RA1 at the incident angle ANG1*a* takes the position of, for example, RA1*a* in FIG. 10, and the position of the turning center axis RA1 at the incident angle ANG1*b* takes the position of, for example, RA1*b* in FIG. 10.

The center axis X-ray CBX1 at the incident angle ANG1*a* is a center axis X-ray CBX1*a* matched with the center axis X-ray CBX1A in an incident angle manner, and the center axis X-ray CBX1 at the incident angle ANG1*b* is a center axis X-ray CBX1*b* matched with the center axis X-ray CBX1B in the incident angle manner.

As described above, the incident angle is caused to correspond to the incident angle in the normal CT imaging in which the turning center is fixed to one point, and the approach and movement away of the X-ray generator 42 and the X-ray detector 52 are changed with respect to the imaging region during the imaging, which allows the magnification factor adjustment CT imaging to be performed.

In the illustrated example, the position RA1*b* of the turning center axis RA1 at the incident angle of 90° is located at a peak separated from the center point CP1. Assuming that the position of the turning center axis RA1 when located on the center point CP1 is a position RA10, the degree of separation of the position RA1*a* from the center point CP1 is equal to the degree between the position RA10 and the position RA1*b*. That is, although the position RA1*a* is separated farther from the center point CP1 than the position RA10, the degree of the position RA1*a* is not as large as that of the position RA1*b*.

In the illustrated magnification factor adjustment CT imaging, it can be seen that the position of the turning center axis RA1 moves on the axial line of the center axis X-ray CBX1 at each timing at which the incident angle changes. At this point, the position of the turning center axis RA1 gradually changes such that a degree of separation of the turning center axis RA1 from the center point CP1 peaks while the center axis X-ray CBX1 is incident on the tomographic layer of interest LOI in the confronting manner.

The degree of separation is maintained so as to be maximized not only in the state in which the center axis X-ray CBX1 is incident on the tomographic layer of interest LOI in the confronting manner, but also in the period of good incident angles close to the confronting state.

As described above, in the imaging unit 20 of the embodiment, the projection magnification factor is decreased when the X-ray generator 42 confronts the tomographic layer of interest LOI, so that the blurring caused by the size of the focal plane 420 can be reduced on the X-ray projection image when the tomographic layer of interest LOI is projected from the front surface. That is, the X-ray projection image can be acquired with high resolution when the tomographic layer of interest LOI is projected from the front surface. Thus, the image quality of the X-ray tomographic image generated with respect to the tomographic layer of interest LOI by the image processor 310 can be improved.

In the X-ray tomography, the X-ray detector 52 is caused to approach the tomographic layer of interest LOI by limiting to a part of the entire turning range in which the X-ray generator 42 and the X-ray detector 52 are turned, which prevents the X-ray detector 52 from contacting with the subject M1. The X-ray generator 42 is moved away from the tomographic layer of interest LOI by limiting to a part of the entire turning range, so that the X-ray generator 42 or the X-ray generation unit 40 accommodating the X-ray generator 42 and one end of the turning arm 62 supporting the X-ray generation unit 40 can be prevented from colliding with another member (such as the post 70).

The X-ray generation controller 810 controls the operation of the X-ray regulating unit 44 according to the movement of the X-ray generator 42 away from the tomographic layer of interest LOI during the turning, so that the emission range of the X-ray beam BX1 (a spread angle (fan angle) about the Z-axis of the X-ray beam BX1) can be decreased. Consequently, the range wider than the imaging region ROI can be prevented from being irradiated with the X-ray beam BX1, so that an X-ray exposure dose of the subject M1 can be reduced.

In the CT imaging of FIG. 19, as described above with reference to FIG. 7, the setting of the imaging region ROI is received such that the imaging region ROI includes at least a part of the dental arch DA1, and the tomographic layer of interest LOI can be set along a part of the dental arch DA1 set in the imaging region ROI. Consequently, because the X-ray tomographic image along the dental arch DA1 can be acquired, the X-ray tomographic image suitable for the dental diagnosis can be acquired. The dental arch DA1 is unevenly distributed in front of the head of the subject M1, and extends along a front edge of the head. For this reason, the setting of the tomographic layer of interest LOI along the dental arch can cause the X-ray detector 52 to approach the head when the X-ray generator confronts the tomographic layer of interest LOI. Thus, the high-resolution X-ray tomographic image can easily be acquired.

The imaging trajectory setting unit 306 determines the imaging trajectories PT42, PT52, and the dose setting unit 308 sets the unit time dose of the X-ray with which the subject M1 is irradiated during the X-ray tomography. That is, the dose setting unit 308 generates the dose control data for operating the imaging controller 80 such that the unit time dose in the period in which the X-ray generator 42 confronts the tomographic layer of interest LOI is larger than the unit time dose in the period in which the X-ray generator 42 does not confront the tomographic layer of interest LOI. When the unit time dose is changed by changing the X-ray intensity, the dose setting unit 308 can generate the dose control data that causes the X-ray generation controller 810 to change the X-ray intensity in FIG. 11. When the unit time dose is changed by changing the turning velocity, the dose setting unit 308 can generate the dose control data that causes the turning controller 802 to change the turning velocity in FIG. 12.

FIG. 21 is a view illustrating an example of the X-ray tomography. The X-ray tomography in FIG. 21 is the CT imaging, in which the vicinity of the right molar in the jaw is set to the imaging region ROI and a part of the dental arch DA1 is included in the imaging region ROI. The tomographic layer of interest LOI is the region extending linearly along the tangential line of a part of the dental arch DA1 included in the imaging region ROI.

In the CT imaging, the X-ray generator 42 is turned by 360° from the position 42p0 at the right rear side of the head of the subject M1 to the position 42p0 after passing through each of the positions 42p1 to 42p7. The X-ray detector 52 is turned by 360° from the position 52p0 on the left front side of the head of the subject M1 to the position 52p0 after passing through each of the positions 52p1 to 52p7. That is, in the CT imaging, the imaging conditions and the like are matched with those in the CT imaging of FIG. 13 except for the imaging trajectory.

Assuming that the direction from the center of the head is an hour hand of a clock, the nose of the head is expressed as 12 o'clock, the back of the head is expressed as 6 o'clock, a right ear is expressed as 3 o'clock, and a left ear is expressed as 9 o'clock. During the CT imaging, the center axis X-ray CBX1 confronts the tomographic layer of interest LOI while being orthogonal to the tomographic layer of interest LOI when the subject M1 is irradiated with the X-ray beam BX1 from the right side of the subject M1 (specifically, between 12 o'clock and 3 o'clock, and the right side when the entire head is roughly divided into the left and the right) (when the X-ray generator 42 passes through the position 42p2 and the X-ray detector 52 passes through the position 52p2), and when the subject M1 is irradiated with the X-ray beam BX1 from the left side of the subject M1 (specifically, between 6 o'clock and 9 o'clock, and the left side when the entire head is roughly divided into the left and the right) (when the X-ray generator 42 passes through the position 42p6 and the X-ray detector 52 passes through the position 52p6).

In the CT imaging, when the X-ray generator 42 confronts the tomographic layer of interest LOI, the X-ray generator 42 passes through the positions 42p2, 42p6. The positions 42p2, 42p6 are positions moved farther away from the tomographic layer of interest LOI than the position (for example, the positions 42p0, 42p1, 42p3 to 42p5, 42p7) of the X-ray generator 42 in the period in which the X-ray generator 42 does not confront the tomographic layer of interest LOI. In the CT imaging, when the X-ray generator 42 confronts the tomographic layer of interest LOI, the X-ray detector 52 passes through the positions 52p2, 52p6. The positions 52p2, 52p6 are positions moved farther away from the tomographic layer of interest LOI than the position (for example, the positions 52p0, 52p1, 52p3 to 52p5, 52p7) of the X-ray detector 52 in the period in which the X-ray generator 42 does not confront the tomographic layer of interest LOI. As described above, by setting the imaging trajectories PT42, PT52 of the X-ray generator 42 and the X-ray detector 52, the projection magnification factor in the period in which the X-ray generator 42 confronts the tomographic layer of interest LOI is smaller than the projection magnification factor in the period in which the X-ray generator 42 does not confront the tomographic layer of interest LOI.

The confronting state when the X-ray generator 42 passes through the position 42p2 is set to a first confronting state, and the confronting state when the X-ray generator 42 passes through the position 42p6 is set to a second confronting state. The position 52p2 of the X-ray detector 52 in the first confronting state is closer to the tomographic layer of interest LOI than the position 52p6 of the X-ray detector 52 in the second confronting state. Because the target imaging region ROI is unevenly distributed on the right side (between 12 o'clock and 3 o'clock) of the head of the subject M1, the X-ray detector 52 can be caused to approach the imaging region ROI as compared to the case of the irradiation from the right side (between 12 o'clock and 3 o'clock) when the subject M1 is irradiated with the X-ray beam BX1 from the left side (between 6 o'clock and 9 o'clock) of the subject M1.

The imaging trajectories PT42, PT52 can be corrected when another mechanical element interferes with the turning of the X-ray generator 42 and the X-ray detector 52. For example, when the post 70 exists between the positions 42p5 to 42p7 of the trajectory of the X-ray generator 42 (the trajectory of the X-ray detectors 52 ranges from the position 52p5 to the position 52p7), the imaging trajectories PT42, PT52 can appropriately be corrected so as to avoid the post 70.

The imaging trajectory setting unit 306 determines the imaging trajectories PT42, PT52, and the dose setting unit 308 sets the dose with which the subject M1 is irradiated during the X-ray tomography. That is, the dose setting unit 308 generates the dose control data for operating the imaging controller 80 such that the unit time dose in the period in which the X-ray generator 42 confronts the tomographic layer of interest LOI is larger than the unit time dose in the period in which the X-ray generator 42 does not confront the tomographic layer of interest LOI. When the unit time dose is changed by changing the X-ray intensity, the dose setting unit 308 can generate the dose control data that causes the X-ray generation controller 810 to change the X-ray intensity in FIG. 14. When the unit time dose is changed by changing the turning velocity, the dose setting unit 308 can generate the dose control data that causes the turning movement drive controller 80D to change the turning velocity in FIG. 15.

In the X-ray tomography of FIGS. 19 and 21, only one tomographic layer of interest LOI is set in the imaging region ROI. However, the tomographic layer of interest LOI set in the imaging region ROI is not limited to one.

Figure 22:
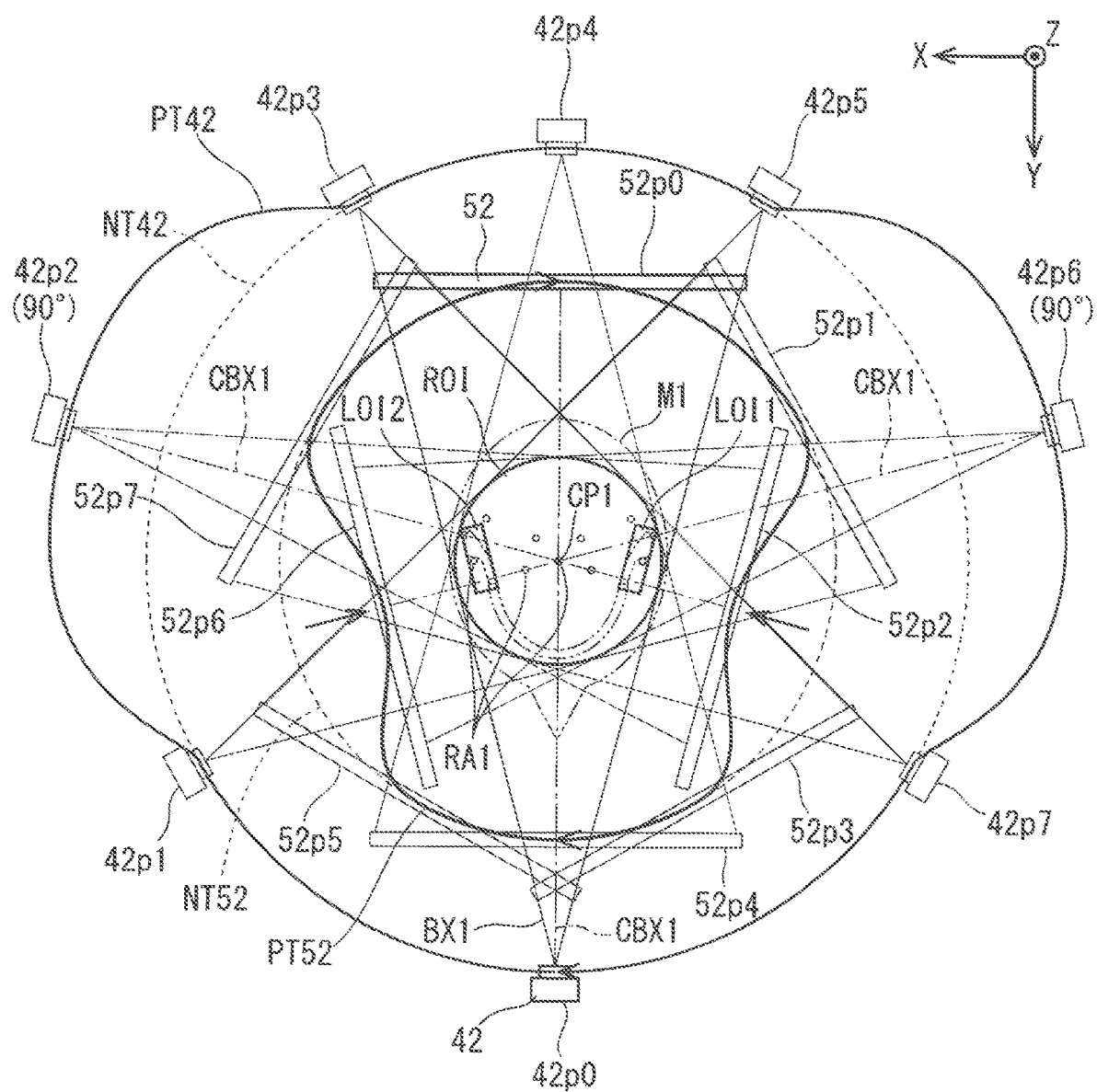
FIG. 22 is a view illustrating an example of the X-ray tomography.

FIG. 22 is a view illustrating an example of the X-ray tomography. The X-ray tomography in FIG. 22 is the CT imaging, in which the entire jaw of the subject M1 is set to the imaging region ROI and two tomographic layers of interest LOI1, LOI2 are set inside the imaging region ROI. At this point, the tomographic layers of interest LOI1, LOI2 are set to the left temporomandibular joint and the right temporomandibular joint, respectively.

In the CT imaging, the X-ray generator 42 is turned by 360° from the position 42p0 in front of the head of the subject M1 to the position 42p0 after passing through the positions 42p1 to 42p7. The X-ray detector 52 is turned by 360° from the position 52p0 on the rear side of the head of the subject M1 to the position 52p0 after passing through the positions 52p1 to 52p7.

In the CT imaging, when the X-ray generator 42 confronts a tomographic layer of interest LOI1, the position 42p2 through which the X-ray generator 42 passes is farther from the tomographic layer of interest LOI1 as compared with the position (for example, positions 42p0, 42p1, 42p3 to 42p5, 42p7) in the period in which the X-ray generator 42 does not confront the tomographic layer of interest LOI1. When the X-ray generator 42 confronts the tomographic layer of interest LOI1, the position 52p2 through which the X-ray detector 52 passes is closer to the tomographic layer of interest LOI1 than the position (for example, positions 52p0, 52p1, 52p3 to 52p5, 52p7) in the period in which the X-ray generator 42 does not confront the tomographic layer of interest LOI1. For this reason, the projection magnification factor in the period in which the X-ray generator 42 confronts the tomographic layer of interest LOI1 can be decreased relatively smaller than the projection magnification factor in the period in which the X-ray generator 42 does not confront the tomographic layer of interest LOI1.

The position 42p6 through which the X-ray generator 42 passes when the X-ray generator 42 confronts a tomographic layer of interest LOI2 is farther from the tomographic layer of interest LOI2 than the positions (for example, the positions 42p0, 42p1, 42p3 to 42p5, 42p7) in the non-confronting state. When the X-ray generator 42 confronts the tomographic layer of interest LOI2, the position 52p6 through which the X-ray detector 52 passes is closer to the tomographic layer of interest LOI2 than the position (for example, positions 52p0, 52p1, p3 to 52p5, 52p7) in the non-confronting state. Consequently, the projection magnification factor can be decreased when the X-ray generator 42 confronts the tomographic layer of interest LOI2.

The position 42p6 is the position when the X-ray generator 42 does not confront the tomographic layer of interest LOI1. It is also assumed that the position 42p2 is closer to the tomographic layer of interest LOI1 than the position 42p6. That is, the position 42p2 through which the X-ray generator 42 passes when confronting the tomographic layer of interest LOI1 is not necessarily farther from the tomographic layer of interest LOI1 than all the positions through which the X-ray generator 42 passes when the X-ray generator 42 does not confront the tomographic layer of interest LOI1. That is, the position 42p2 can be farther from the tomographic layer of interest LOI1 than at least a part of all the positions through which the X-ray generator 42 passes when the X-ray generator 42 does not confront the tomographic layer of interest LOI1.

Similarly, the position 52p6 is the position of the X-ray detector 52 when the X-ray generator 42 does not confront the tomographic layer of interest LOI, but it is assumed that the position 52p6 is located closer to the tomographic layer of interest LOI than the position 52p2. That is, the position 52p2 can be closer to the tomographic layer of interest LOI1 than at least a part of all the positions through which the X-ray detector 52 passes when the X-ray generator 42 does not confront the tomographic layer of interest LOI1.

The dose setting unit 308 generates the dose control data such that the unit time dose in the period in which the X-ray generator 42 confronts the tomographic layer of interest LOI is larger than the unit time dose in the period in which the X-ray generator 42 does not confront the tomographic layer of interest LOI. The dose setting unit 308 generates the dose control data such that the unit time dose in the period in which the X-ray generator 42 confronts the tomographic layer of interest LOI2 is larger than the unit time dose in the period in which the X-ray generator 42 does not confront the tomographic layer of interest LOI2.

Figure 23:
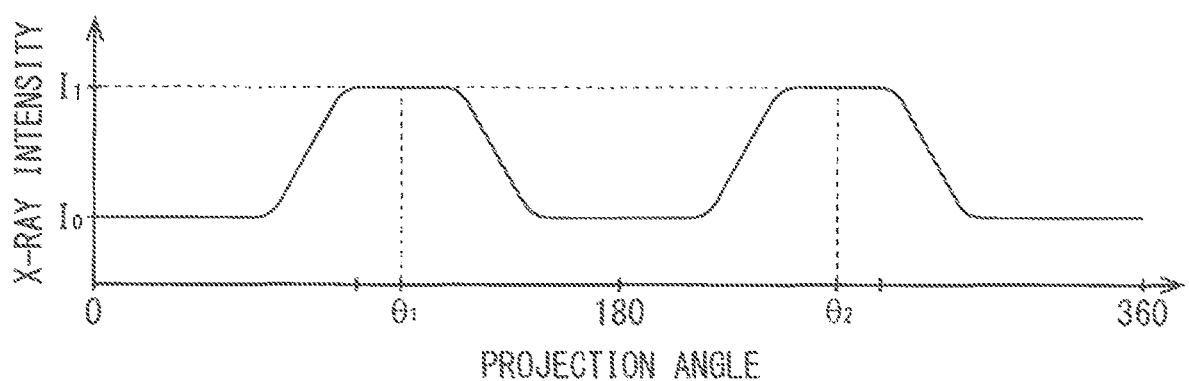
FIG. 23 is a view illustrating the graph G10 of the X-ray intensity corresponding to the projection angle in the CT imaging of FIG. 22.

FIG. 23 is a view illustrating the graph G10 of the X-ray intensity corresponding to the projection angle in the CT imaging of FIG. 22. In FIG. 23, the horizontal axis indicates the projection angle, and the vertical axis indicates the X-ray intensity. When the unit time dose is changed by changing the X-ray intensity, as illustrated in FIG. 23, the X-ray intensity is set to I1 in the period in which the X-ray generator 42 confronts the tomographic layer of interest LOI1 (at the projection angle of θ1) and the period in which the X-ray generator 42 confronts the tomographic layer of interest LOI2 (at the projection angle of θ2), and the X-ray intensity is set to I0 smaller than I1 in the period in which the X-ray generator 42 does not confront the tomographic layer of interest LOI1 and the tomographic layer of interest LOI2.

Figure 24:
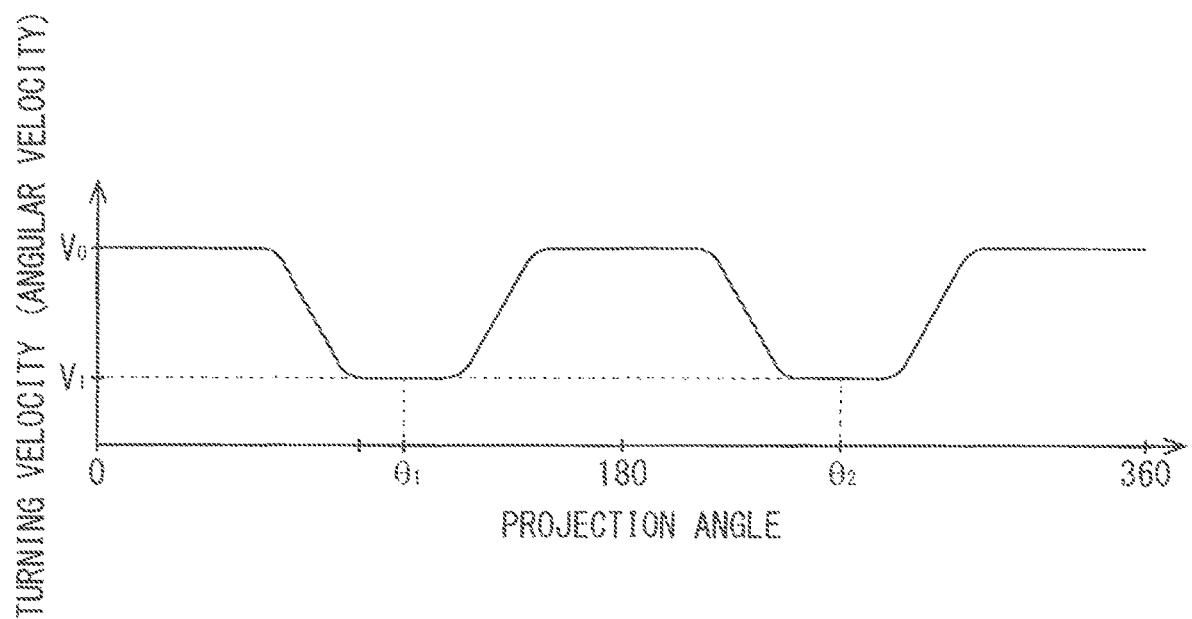
FIG. 24 is a view illustrating the graph G12 of the turning velocity corresponding to the projection angle in the CT imaging of FIG. 22.

FIG. 24 is a view illustrating the graph G12 of the turning velocity corresponding to the projection angle in the CT imaging of FIG. 22. In FIG. 24, the horizontal axis indicates the projection angle, and the vertical axis indicates the turning velocity. When the unit time dose is changed by changing the turning velocity, as illustrated in FIG. 24, the turning velocity is set to V1 in the period in which the X-ray generator 42 confronts the tomographic layer of interest LOI1 (at the projection angle of θ1) and the period in which the X-ray generator 42 confronts the tomographic layer of interest LOI2 (at the projection angle of θ2), and the turning velocity is set to V0 smaller than V1 in the period in which the X-ray generator 42 does not confront the tomographic layer of interest LOI1 and the tomographic layer of interest LOI2.

In the CT imaging of FIG. 22, when the X-ray generator 42 confronts the tomographic layer of interest LOI1 while turning on the right side of the head of the subject M1, the projection magnification factor is reduced and the unit time dose is increased. However, when the X-ray generator 42 confronts the tomographic layer of interest LOI1 while turning on the left side of the head of the subject M1 (when the X-ray generator 42 passes through the side opposite to the position 42p2), the projection magnification factor can be decreased and the unit time dose can be increased.

Similarly, in the CT imaging of FIG. 22, when the X-ray generator 42 confronts the tomographic layer of interest LOI2 while turning on the left side of the head of the subject M1, the projection magnification factor is decreased and the unit time dose is increased. However, when the X-ray generator 42 confronts the tomographic layer of interest LOI2 while turning on the right side of the head of the subject M1 (when the X-ray generator 42 passes through the side opposite to the position 42p6), the projection magnification factor can be decreased and the unit time dose can be increased.

As described above, while the height of the head MH is kept constant by the Z-direction drive unit 646 and the elevation drive unit 728, the support 60 is elevated and lowered with respect to the head MH by the relative movement, which allows the X-ray irradiation location to be changed in the Z-axis direction. For this reason, for example, the plurality of imaging regions located at different height positions can continuously be imaged such that one of the tooth rows of the upper jaw and the lower jaw is continuously imaged after the other is imaged. In this case, different regions of the dental arch can be set to the imaging target in each height position such that a front-tooth region is set in the upper jaw and a molar region is set in the lower jaw.

Figure 25:
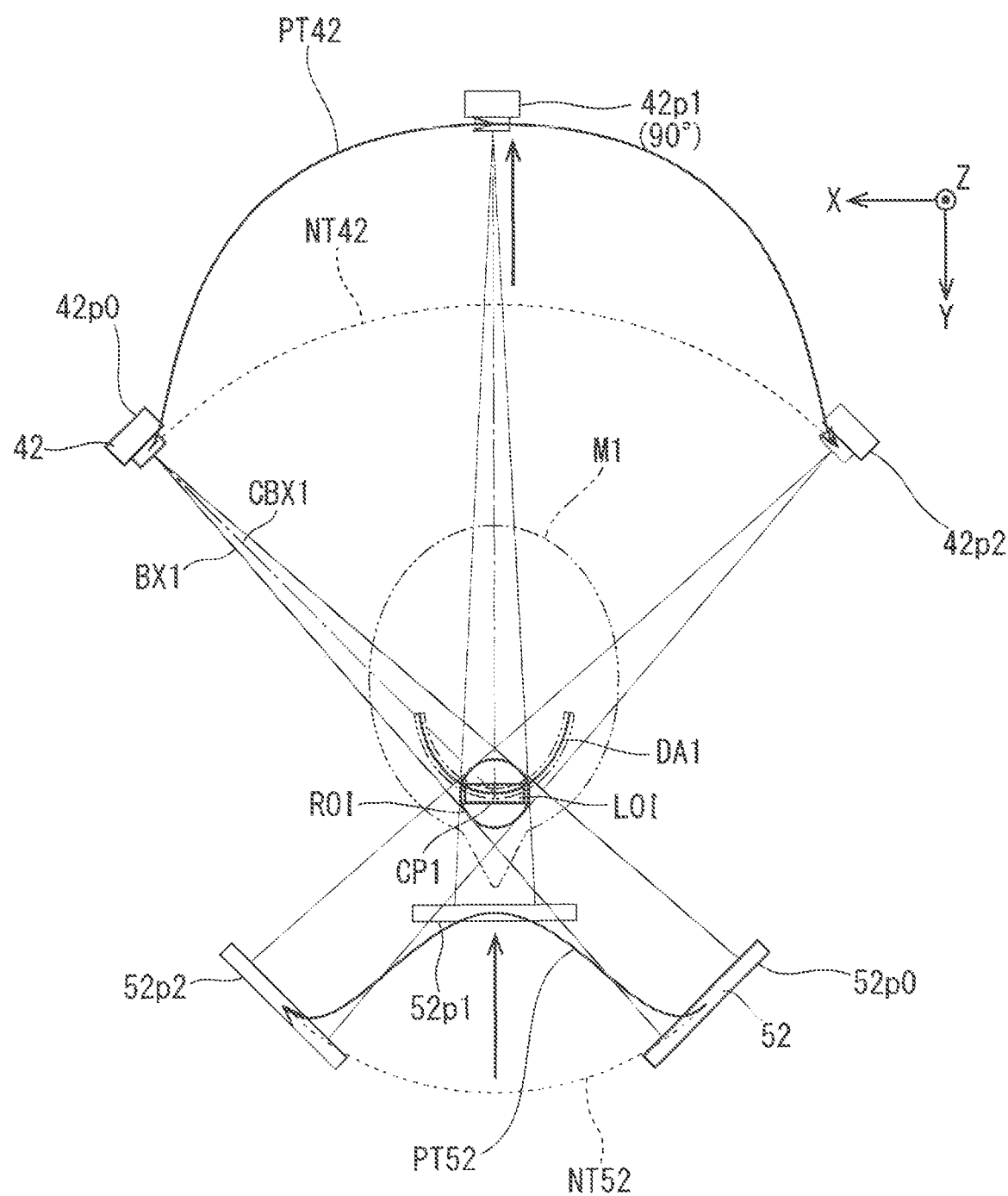
FIG. 25 is a view illustrating an example of the X-ray tomography.

FIG. 25 is a view illustrating an example of the X-ray tomography. The X-ray tomography in FIG. 25 is tomosynthesis imaging in which the X-ray generator 42 and the X-ray detector 52 are turned by an angle less than 180° around the head of the subject M1. For example, the turning angle can be set to 90° or 60°. Any angle less than 180° can be set by the operation, and any angle between 90° and 60° can be set by the operation. In the tomosynthesis imaging, as illustrated in FIG. 25, the X-ray projection image is acquired by rotating the X-ray generator 42 and the X-ray detector 52 to the left and right by a required angle around the incident angle ANG1 at which the X-ray generator 42 confronts the tomographic layer of interest LOI to be observed by an observer. In the tomosynthesis imaging, an X-ray tomographic images having relatively high quality can be acquired by reconstruction with respect to the tomographic layer of interest LOI. Since the X-ray irradiation less than only 180° is performed, the tomosynthesis imaging has an advantage that an imaging time can be shortened while the X-ray exposure dose of the subject M1 is reduced as compared with the CT imaging.

In the tomosynthesis imaging of FIG. 25, the imaging region ROI is set in the vicinity of the front teeth of the jaw of the subject M1, and the tomographic layer of interest LOI is set along the portion of the dental arch DA1 included in the imaging region ROI. The X-ray generator 42 is turned from the position 42p0 on the right rear side of the subject M1 to the position 42p2 on the left rear side, and the X-ray detector 52 is turned from the position 52p0 on the right front side of the subject M1 to the position 52p2 on the left front side. When the X-ray generator 42 confronts the tomographic layer of interest LOI, the imaging trajectories of the X-ray generator 42 and the X-ray detector 52 are set such that the X-ray generator 42 passes through the position 42p1 and the X-ray detector 52 passes through the position 52p1. The position 42p1 of the X-ray generator 42 is farther from the tomographic layer of interest LOI than the position (for example, the positions 42p0, 42p2) of the X-ray generator 42 when the X-ray generator 42 does not confront the tomographic layer of interest LOI. The position 52p1 is closer to the tomographic layer of interest LOI than the position (for example, the positions 52p0, 52p2) of the X-ray detector 52 when the X-ray generator 42 does not confront the tomographic layer of interest LOI. The setting of the imaging trajectory in this manner decreases the projection magnification factor during the confrontation, so that the high-quality X-ray tomographic image can be generated with respect to the tomographic layer of interest LOI.

In performing the tomosynthesis imaging in FIG. 25, the dose setting unit 308 generates the dose control data for operating the imaging controller 80 such that the unit time dose is relatively increased as compared with the case where the X-ray generator 42 confronts the tomographic layer of interest LOI and the case where the X-ray generator 42 does not confront the tomographic layer of interest LOI. For example, when the unit time dose is changed by changing the X-ray intensity, the X-ray intensity when the X-ray generator 42 passes through the position 42p1 where the X-ray generator 42 confronts the tomographic layer of interest LOI is preferably increased larger than the X-ray intensity at the position (for example, the positions 42p0, 42p2) where the X-ray generator 42 does not confront the tomographic layer of interest LOI. When the unit time dose is changed by changing the turning velocity, the turning velocity when the X-ray generator 42 is located the position 42p1 where the X-ray generator 42 confronts the tomographic layer of interest LOI is preferably decreased smaller than the turning velocity at the position (for example, the positions 42p0, 42p2) where the X-ray generator 42 does not confront the tomographic layer of interest LOI.

Flow of X-ray Tomography

Figure 26:
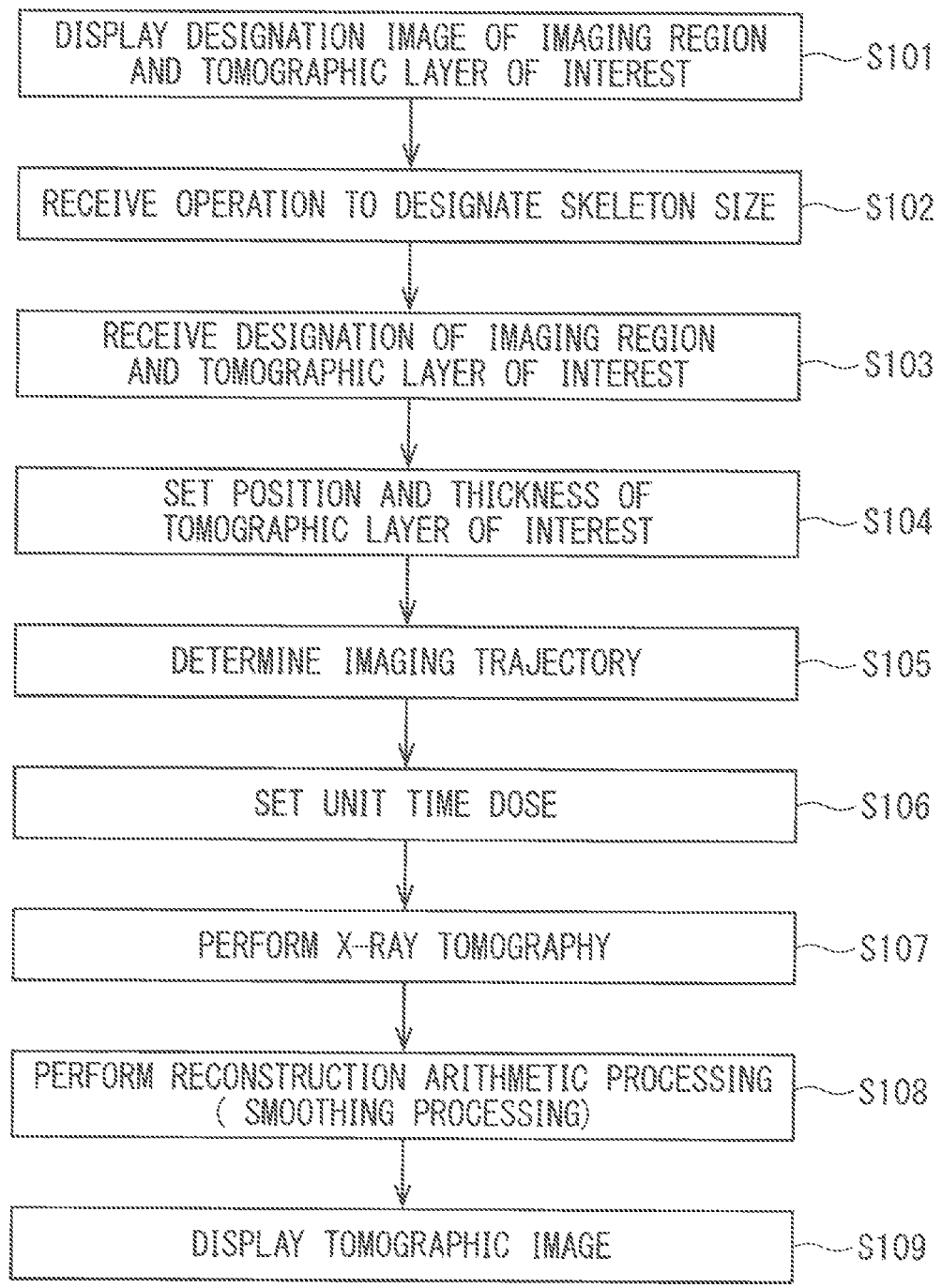
FIG. 26 is a flowchart illustrating operation of an X-ray tomography apparatus 10.

FIG. 26 is a flowchart illustrating the operation of the X-ray tomography apparatus 10. In the following description, it is assumed that positioning of the subject M1 in the imaging unit 20 is already completed.

The information processor 30 causes the display 32 to display the designation image for designating the tomographic layer of interest LOI or the imaging region ROI (step S101). For example, as illustrated in FIGS. 4 to 8, the designation image is a schematic diagram IL1 in which the site of interest is drawn, or a transmission image (such as a panoramic X-ray image IL2 and a transmission image in which the X-ray tomography is performed in the two directions) obtained by the X-ray tomography of the subject M1.

Subsequently, the information processor 30 receives an operation to designate a skeleton size (step S102). For example, when the operator inputs the physical characteristics (such as the gender, the age, the height, and the weight) of the subject M1, the information processor 30 acquires the skeleton size corresponding to the input physical characteristics from a predetermined database. In each size, a standard size can be set from statistical data. The acquired skeleton size is used to approximately match the position of the imaging target site of the subject M1 disposed in the imaging unit 20 with the position of the imaging target site in the designation image.

When the transmission image (such as a panoramic X-ray image IL2) obtained by the X-ray tomography of the subject M1 is used as the designation image, step S102 can be skipped. When the skeleton size is designated in step S102, the information processor 30 can re-display the designation image matched with the designated skeleton size on the display 32. For example, the schematic diagram IL1 for each physical characteristic is previously prepared, and the schematic diagram IL1 corresponding to the specified physical characteristic can be displayed.

Subsequently, the information processor 30 receives an operation to designate the tomographic layer of interest LOI or the imaging region ROI (step S103). For example, the operation to designate the tomographic layer of interest LOI or the imaging region ROI is described with reference to FIGS. 4 to 8. In step S103, each of the tomographic layer of interest LOI and the imaging region ROI can individually be designated. As described above with reference to FIG. 7, the tomographic layer of interest LOI can automatically be set according to the designation of the imaging region ROI. The imaging region ROI can automatically be set according to the designation of the tomographic layer of interest LOI.

Subsequently, the tomographic layer-of-interest setting unit 304 sets the position, the size, and the direction of the tomographic layer of interest LOI based on the designation operation received in step S103 (step S104).

Subsequently, the imaging trajectory setting unit 306 determines the imaging trajectories of the X-ray generator 42 and the X-ray detector 52 when the X-ray tomography is performed (step S105). When the projection magnification factor is changed during the X-ray tomography, the imaging trajectory setting unit 306 determines the imaging trajectories PT42, PT52 of the X-ray generator 42 and the X-ray detector 52 based on the tomographic layer of interest LOI set in step S104. Specifically, as described above with reference to FIGS. 19 to 22, and 25, the imaging trajectory setting unit 306 determines the imaging trajectories PT42, PT52 such that the projection magnification factor when the X-ray generator 42 confronts the tomographic layer of interest LOI is smaller than the projection magnification factor when the X-ray generator 42 does not confront the tomographic layer of interest LOI. On the other hand, when the projection magnification factor is not changed, the imaging trajectory setting unit 306 determines the normal imaging trajectories NT42, NT52 as described above with reference to FIGS. 9, 13, and 16.

Preferably, the operator can select whether the projection magnification factor is changed in performing the X-ray tomography. That is, a selection screen selecting necessity of the change of the projection magnification factor is displayed on the display 32, and the operator can perform operation input through the operation unit 34 according to the selection screen.

Subsequently, the dose setting unit 308 sets the dose with which the subject M1 is irradiated when the X-ray tomography is performed (step S106). Specifically, as described with reference to FIGS. 9 to 17, the dose setting unit 308 generates the dose control data for operating the imaging controller 80 such that the unit time dose in the period in which the X-ray generator 42 confronts the tomographic layer of interest LOI is larger than the unit time dose in the period in which the X-ray generator 42 does not confront the tomographic layer of interest LOI. When the unit time dose is changed by changing the X-ray intensity, the dose setting unit 308 can generate the dose control data for operating the X-ray generation controller 810. When the unit time dose is changed by changing the turning velocity, the dose setting unit 308 can generate the dose control data for operating the turning movement drive controller 80D.

As described above with reference to FIG. 16, the dose setting unit 308 can change the unit time dose corresponding to the projection angle in consideration of the high X-ray absorption site HAL The dose setting unit 308 can generate the dose control data for operating the imaging controller 80 so as to increase the unit time dose at the projection angle at which the X-ray beam BX1 passes through the high X-ray absorption site HAL The position information about the high X-ray absorption site HA1 used at this time can correspond to the skeleton size designated in step S102. In this case, the pieces of position information about a plurality of high X-ray absorption sites HA1 according to the physical characteristics of the subject is previously stored in the storage 31, and the position information corresponding to the designated skeleton size can be read out from the storage 31.

After the setting of the imaging trajectory in step S105 and the setting of the unit time dose in step S106, the imaging unit 20 performs the X-ray tomography (step S107). Specifically, data of the imaging trajectory and the dose control data are sent to the imaging controller 80. Based on the data, the X-ray irradiation with the set unit time dose is performed, and the turning movement drive controller 80D performs the control such that the turning controller 802 controls the operation of the turning drive unit 642, and such that the XY-direction movement controller 804 controls the operation of the XY-direction movement drive unit 644. The imaging unit 20 captures the X-ray projection image of the imaging region ROI projected on the detection surface of the X-ray detector 52 at a predetermined frame rate. The captured X-ray projection image is appropriately stored in the storage 31 or the like of the information processor 30.

Subsequently, the image processor 310 performs reconstruction arithmetic processing on the plurality of X-ray projection images acquired in step S107 (step S108). Specifically, the image processor 310 generates three-dimensional volume data of the imaging region ROI by a filter correction back projection method (FBP method), a superposition integration method, or the like. The image processor 310 generates the X-ray tomographic image representing the tomographic layer of interest LOI based on the three-dimensional volume data. Although being concentrated on and around the tomographic layer of interest LOI, three-dimensional image data having a certain thickness can also be generated in the tomosynthesis imaging, and the X-ray tomographic image representing the tomographic layer of interest LOI can be generated.

As described above, in the imaging unit 20, the dose setting unit 308 generates the dose control data so as to decrease the unit time dose when the X-ray generator 42 does not confront the tomographic layer of interest LOI. Thus, the noise is easily generated in the X-ray projection image. This is because the image quality is degraded due to the influence of Poisson noise (shot noise) generated by the low dose. For this reason, the image processor 310 performs the smoothing processing on the X-ray projection image obtained at the projection angle in the non-confronting state.

When the X-ray tomographic image is generated for the tomographic layer of interest LOI, the X-ray tomographic image is displayed on the display 32 (step S109).

Filter for Smoothing Processing

The smoothing filter used when the image processor 310 smoothes the X-ray projection image will be described below.

Figure 27:
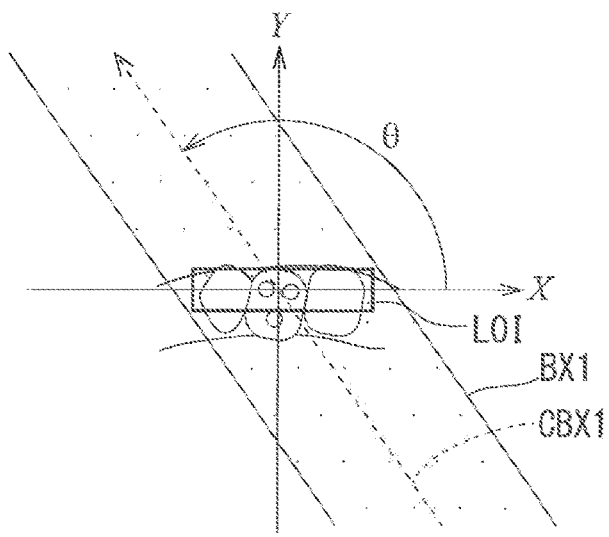
FIG. 27 is a view illustrating a state in which the tomographic layer of interest LOI is irradiated with an X-ray.
Figure 28:
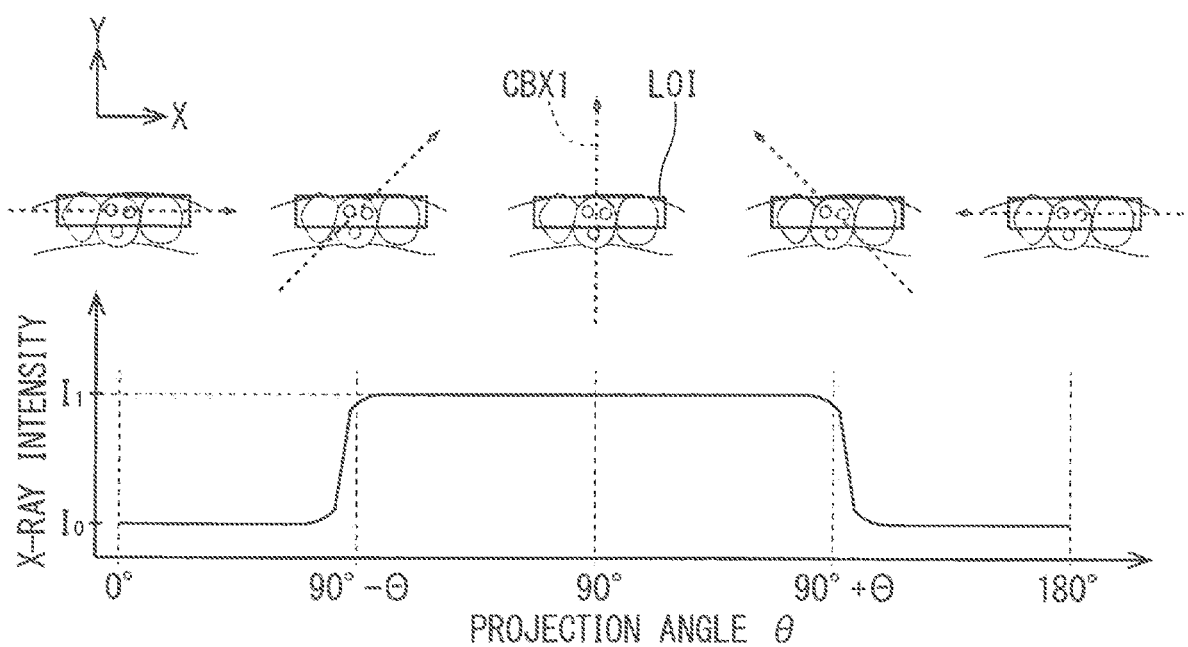
FIG. 28 is a view illustrating a change in the X-ray intensity when X-ray tomography is performed on the tomographic layer of interest LOI.

FIG. 27 is a view illustrating the state in which the tomographic layer of interest LOI is irradiated with the X-ray. FIG. 28 is a view illustrating the change in the X-ray intensity when the X-ray tomography is performed on the tomographic layer of interest LOI.

As illustrated in FIG. 27, it is assumed that the tomographic layer of interest LOI that extends in parallel to the X-axis and has a predetermined thickness in the Y-axis direction. The center of the tomographic layer of interest LOI is set to an origin (0, 0) of an XY-coordinate system. It is assumed that the X-ray generator 42 turns such that the center axis X-ray CBX1 of the X-ray beam BX1 always passes through the origin. As illustrated in FIG. 28, the direction of the center axis X-ray CBX1 at the beginning of the X-ray tomography is set to the +X-direction, and the rotation angle of the center axis X-ray CBX1 from the X-axis is set to the projection angle θ. Specifically, X-ray irradiation starts with the relatively low X-ray intensity I0 from the projection angle of 0°, and the X-ray intensity is increased from the near side on which the projection angle becomes 90°−Θ. After the projection angle passes through 90°−Θ, the X-ray irradiation is performed with relatively high X-ray intensity I1. The X-ray intensity is maintained at I1 at the projection angle of 90° and around 90°. The X-ray intensity is decreased from the near side on which the projection angle becomes 90°+Θ, and the X-ray intensity is decreased from around the projection angle that passes through 90°+Θ, and decreased to the relatively low X-ray intensity I0. The X-ray intensity is maintained at I0 until the projection angle becomes 180°. An example of the setting of Θ that is a point changing the X-ray intensity will be described later.

Figure 29:
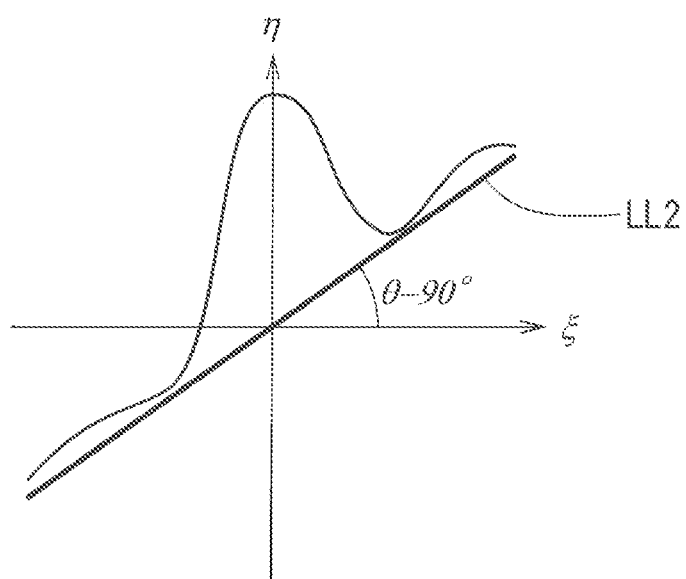
FIG. 29 is a view illustrating a spatial frequency distribution of the X-ray projection image projected at a projection angle θ.

FIG. 29 is a view illustrating a spatial frequency distribution of the X-ray projection image projected at the projection angle θ. When the X-ray projection image obtained at the projection angle θ is Fourier-transformed, a Fourier coefficient at the position of a straight line LL2 is obtained as illustrated in FIG. 29. The angle between the straight line LL2 and the horizontal axis (ξ axis) is θ−90°. As illustrated in FIG. 29, the Fourier coefficient of a high-frequency component is acquired while attenuated more than the Fourier coefficient of a low-frequency component.

Figure 30:
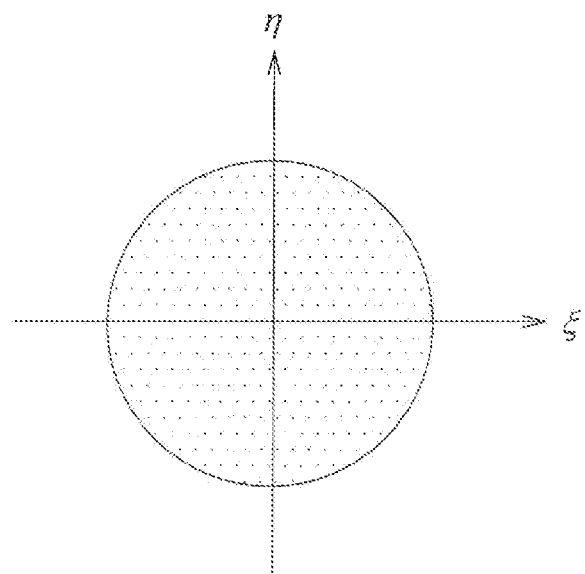
FIG. 30 is a view conceptually illustrating the spatial frequency distribution of X-ray projection data for 180°.

FIG. 30 is a view conceptually illustrating the spatial frequency distribution of X-ray projection data for 180°. As illustrated in FIG. 30, the spatial frequency distribution in which the Fourier coefficient of the high frequency component is attenuated with respect to the original image (a distribution of a linear attenuation coefficient in the real space) can be obtained by acquiring X-ray projection data for 180°. The original image can be reconstructed by performing inverse Fourier transform or the like on the spatial frequency distribution.

It is considered that blurring is performed with a Gaussian filter H. The Gaussian filter H is given by the following equation.

[Mathematical Formula 1]

$$H(\xi, \eta) = \exp\left(-\frac{\eta^2}{2R^2}\right) \quad (1)$$

The multiplication of the spatial frequency distribution of projection data and the Gaussian filter H means the obtainment of a composition product (h * f) of a distribution f obtained by the inverse Fourier transform and h that is the inverse Fourier transform of H. The inverse Fourier transform h and the composition product (h * f) of H are given by the following equations.

[Mathematical Formula 2]

$$h(X, Y) = \exp\left(-\frac{Y^2}{2r^2}\right) \quad (2)$$

[Mathematical Formula 3]

$$(h^*f)(X, Y) = \int \exp\left(-\frac{Y'^2}{2r^2}\right) f(X, Y - Y')dY' \quad (3)$$

As indicated by the equation (3), the obtainment of the composition product of the distribution f and the inverse Fourier transform h is equivalent to the blurring of the distribution f in the Y-direction. The blurring in the Y-direction means performing addition in the Y-direction. That is, the blurring in the Y-direction is equivalent to calculation of the X-ray tomographic image having a tomographic thickness 2r or 4r. Thus, in the case of calculating the tomographic layer of interest LOI having a constant tomographic direction, it is sufficient to obtain information after applying h represented by the equation (2).

FIG. 31 is a view illustrating multiplication of the spatial frequency distribution of the projection data in FIG. 30 and the Gaussian filter H. As illustrated in FIG. 31, the shape is attenuated in an η-direction by multiplying the spatial frequency distribution of the projection data in FIG. 30 by the Gaussian filter H.

The image in which the X-ray tomography obtaining the spatial frequency distribution in FIG. 31 and the inverse Fourier transform are performed is an image in which the distribution f obtained by CT reconstruction is blurred by the inverse Fourier transform h of the equation (2), namely, an image of the tomographic layer parallel to the X-axis.

In the embodiment, after the imaging is performed while the X-ray intensity (unit time dose) is changed as illustrated in FIG. 28, the image processing is performed on the obtained X-ray projection image. At this point, the smoothing processing (blurring processing) in the rotational direction is performed on the X-ray projection image obtained at the projection angle at which the X-ray intensity is relatively small (I0). The noise is reduced by the addition because the image quality is degraded due to the influence of Poisson noise (shot noise) generated by the low dose.

FIG. 32 is a view conceptually illustrating the spatial frequency distribution of all pieces of X-ray projection data when the smoothing processing is performed on the low-dose X-ray projection image. In the spatial frequency distribution of FIG. 32, as to the spatial frequency distribution corresponding to the projection angle (0° to 90°−Θ, 90°+Θ to 180°) of relatively low unit time dose, a distribution radius becomes relatively small because the high-frequency component is attenuated by the smoothing processing. On the other hand, as to the spatial frequency distribution corresponding to the projection angle (90°−Θ to 90°+Θ) of relatively high unit time dose, the distribution radius becomes relatively large. A rectangular region RR equivalent to the spatial frequency distribution in FIG. 31 is included in the center portion of the spatial frequency distribution in FIG. 32 as indicated by a broken line. That is, it can be said that the spatial frequency distribution in FIG. 32 includes information necessary for the calculation of the X-ray tomographic image of the tomographic layer of interest LOI having a certain thickness in the Y-axis direction.

It is assumed that d is the radius of the smoothing filter. When the X-ray projection data obtained at the projection angle of the relatively low unit time dose is processed with a blurring filter having a radius d, the radius of the spatial frequency distribution becomes 1/d. Assuming that σ is the thickness of the required tomographic layer of interest LOI, the length on the +η-side of the rectangular region RR in the spatial frequency distribution becomes 1/σ. For this reason, the following equations hold for the radius d of the smoothing filter, the thickness σ of the tomographic layer of interest LOI, and the angle Θ.

[Mathematical Formula 4]

$$\frac{1}{\sigma} = \frac{1}{d}\sin\Theta \quad (4)$$

For example, the range of the angle at which the relatively high unit time dose is irradiated is reduced when the thickness σ of the tomographic layer of interest LOI is increased, and the range of the angle at which the relatively higher unit time dose is irradiated is enlarged when the thickness σ of the tomographic layer of interest LOI is decreased.

As described above, because the thickness TN1 of the tomographic layer of interest LOI in FIG. 3 can be set based on the designation input from the operator, a tomographic thickness designation receiving unit 304*t* that receives the designation of the tomographic thickness (not illustrated) can be provided in the tomographic layer-of-interest setting unit 304. Preferably, an increase and decrease pattern of the unit time dose based on the control of the imaging controller 80 can be set according to the size of the tomographic thickness relating to the designation received by the tomographic thickness designation receiving unit 304*t*. That is, when the tomographic thickness relating to the designation is relatively large, the imaging controller 80 can relatively reduce the range of the incident angle of the X-ray beam BX1 emitting the relatively high unit time dose. When the tomographic thickness relating to the designation is relatively small, the imaging controller 80 can enlarge the range of the incident angle of the X-ray beam BX1 emitting the relatively high unit time dose.

The radius of the smoothing can be changed according to the dose change (the change in the smoothing size). Specifically, when the dose is 1/α, the radius d of the smoothing filter can be increased larger than 2α. When the radius d is excessively increased, the strength of the rectangular region RR is weakened. The maximum size of the allowable radius d is d (=σ·sin θ) given by replacing "Θ" in the equation (4) with "θ". That is, the radius d can be changed within the range of 2α to σ·sin θ.

In the example of FIG. 28, the high X-ray intensity is set to I1 and the low X-ray intensity is set to I0. It is assumed that Tγ0 is the total dose when the X-ray tomography is performed while the X-ray intensity is fixed at I1, and that Tγ1 is the total dose of the X-ray tomography of the embodiment. The ratio of Tγ0 and Tγ1 is given by the following equation (5).

[Mathematical Formula 5]

$$\frac{T\gamma_1}{T\gamma_0} = \frac{2\Theta I_1 + (180 - 2\Theta)I_0}{180 I_1} = \frac{2\Theta + (180 - 2\Theta)I_0/I_1}{180} \quad (5)$$

For example, θ is set to 10°, and I0/I1 is set to 1/5. Substituting these values into the equation (5), Tγ0:Tγ1 becomes approximately 4:1. That is, when the X-ray tomography is performed while the low dose and the high dose are switched, the total exposure dose can be suppressed to 1/4 as compared with the case where the X-ray tomography is always performed with the high dose.

An SN ratio is decreased by decreasing the unit time dose. It is conceivable that the SN ratio is improved by adding pixel values by the dose ratio. For example, for the dose ratio (in this case, the ratio of X-ray intensities I0 and I1) of 1/5, assuming that d is the radius of the smoothing filter, 1/5=1/2d, namely, the radius d can be set to 2.5 when the pixels are continuously considered. When the pixels are discretely considered, 1/5=1/(2d+1), namely, the radius d can be set to 2.

Θ can be set to any value. For example, the arithmetic calculation can be performed while Θ is set to 5° according to the substantially right angle in the above description with reference to FIG. 10.

2. Modifications

Although the embodiment is described above, the present invention is not limited to the above embodiment, and various modifications can be made. Modification of the above embodiment will be described below. In the following description, the element having the function similar to that of the already described element is denoted by the identical reference numeral or the reference numeral to which an alphabetical letter is added, and sometimes the detailed description will be omitted.

First Modification

Figure 33:
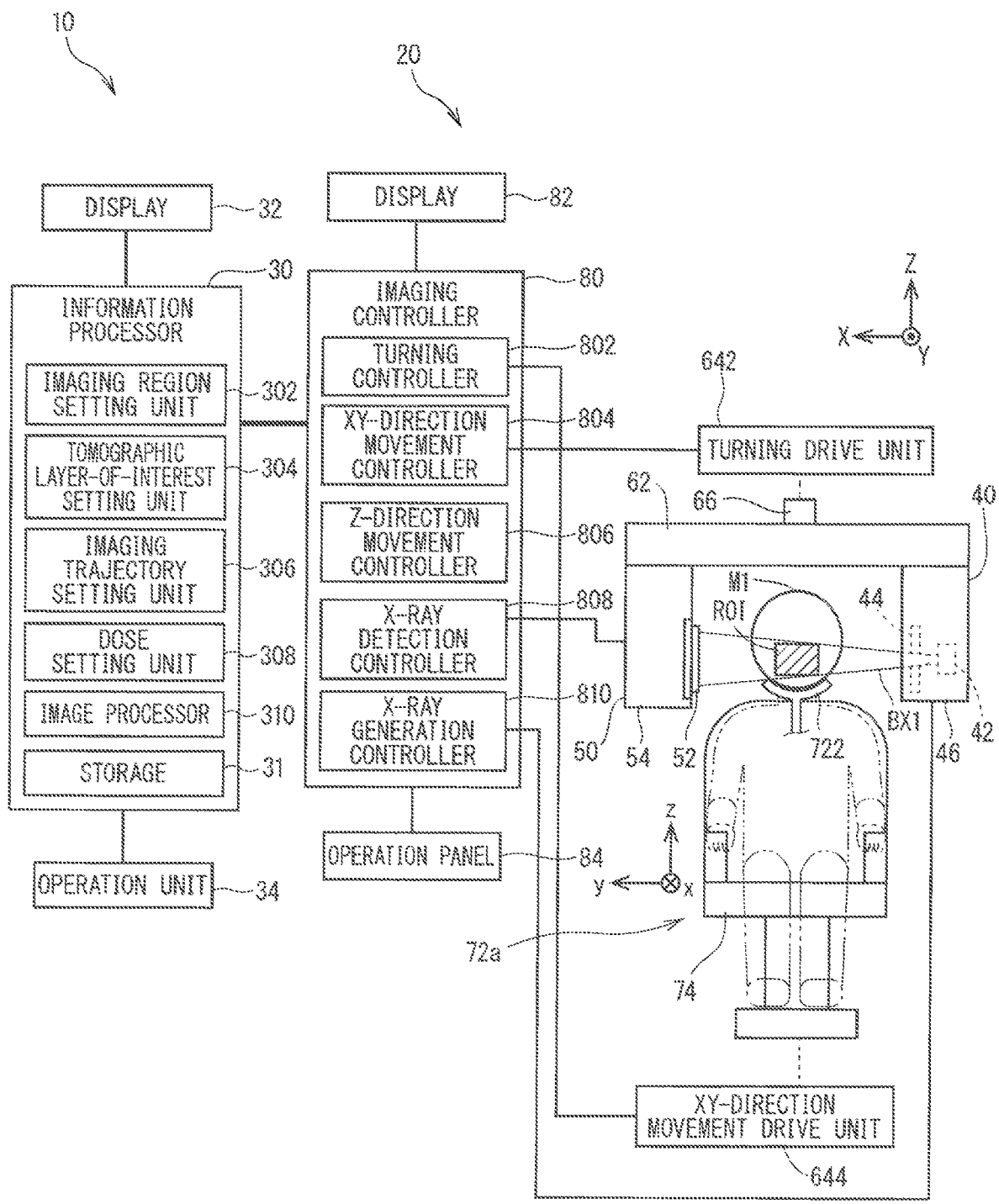
FIG. 33 is a view illustrating a configuration of an X-ray tomography apparatus 10 according to a modification.

FIG. 33 is a view illustrating a configuration of an X-ray tomography apparatus 10 according to a first modification. A subject holder 72a of the first modification includes a subject chair 74 on which the subject M1 is seated. In the embodiment illustrated in FIG. 1 and FIG. 2, the XY-direction movement drive unit 644 translates the turning arm 62 in the XY plane by moving the shaft 66 in the X axis direction and the Y axis direction. As a result, the X-ray generator 42 and the X-ray detector 52 move relative to the subject M1 in the X-axis direction and the Y-axis direction. On the other hand, in this modification, the XY-direction movement drive unit 644 is connected to the subject chair 74, and moves the subject chair 74 in the X-axis direction and the Y-axis direction. Consequently, the subject M1 moves relative to the X-ray generator 42 and the X-ray detector 52 of the turning arm 62 in the X-axis direction and the Y-axis direction.

For the X-ray tomography apparatus 10 of the first modification, when the projection magnification factor is decreased during the X-ray tomography, the subject chair 74 is moved so as to move the subject M1 to an appropriate position during the X-ray tomography. That is, when the X-ray generator 42 confronts the tomographic layer of interest LOI, the portion corresponding to the tomographic layer of interest LOI is moved away from the X-ray generator 42, and caused to approach the X-ray detector 52. Consequently, the projection magnification factor can be decreased in the confronting state.

In the imaging unit 20 of the embodiment, the turning drive unit 642 rotates the turning arm 62 to turn the X-ray generator 42 and the X-ray detector 52 around the subject M1. However, the turning drive unit 642 can rotate the subject holder to rotate the subject.

The imaging unit 20 does not necessarily include the turning arm 62. For example, while the X-ray generation unit 40 and the X-ray detection unit 50 are attached to a ring-shaped annular member, the X-ray generation unit 40 and the X-ray detection unit 50 can move along the circumferential direction of the annular member. In this case, a virtual axis passing through the center of the annular member is the turning center axis RA1.

In the imaging unit 20, the turning center axis RA1 extending in the Z-axis direction is set to the vertical direction. However, the turning center axis RA1 can be set to the horizontal direction.

Configuration That Moves Only One of X-ray Generator 42 and X-ray Detector 52

In the above embodiment, when the X-ray generator 42 confronts the tomographic layer of interest LOI, the projection magnification factor is decreased by moving both the X-ray generator 42 and the X-ray detector 52 with respect to the tomographic layer of interest LOI. However, the projection magnification factor can be decreased by moving only one of the X-ray generator 42 and the X-ray detector 52 with respect to the tomographic layer of interest LOI.

Figure 34:
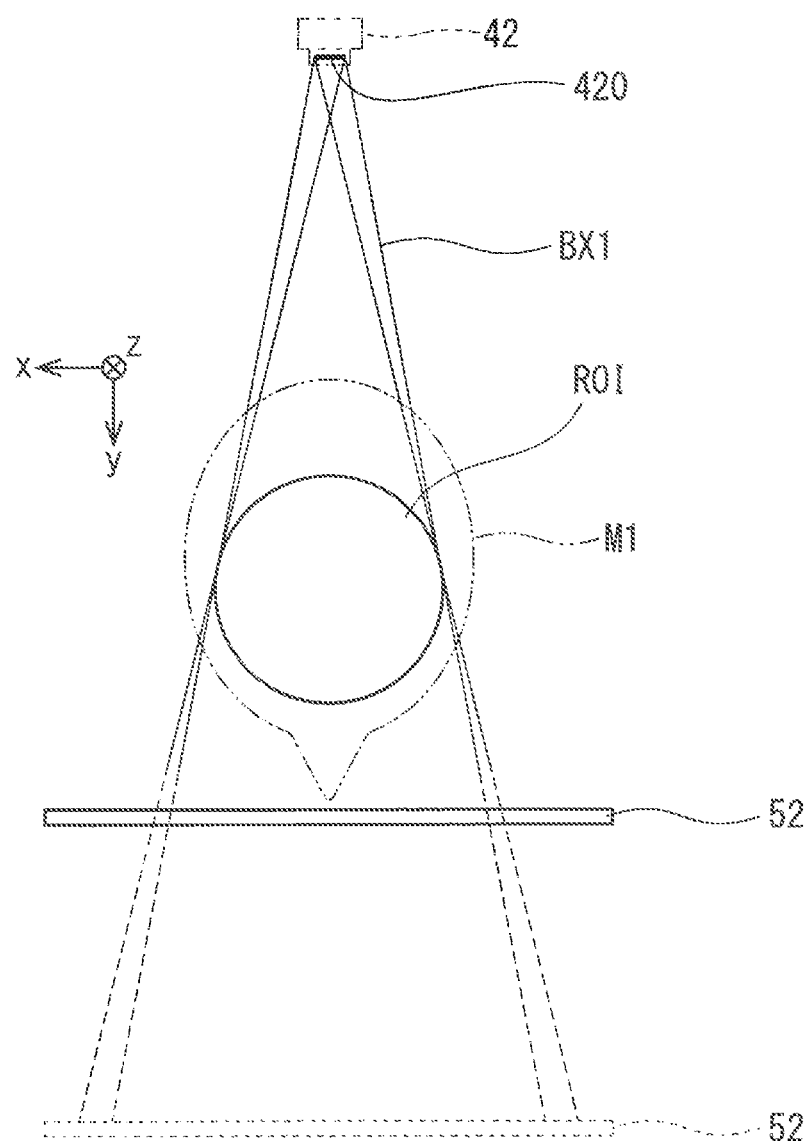
FIG. 34 is a view illustrating a state in which the projection magnification factor is decreased by moving only an X-ray detector 52.

FIG. 34 is a view illustrating the state in which the projection magnification factor is decreased by moving only the X-ray detector 52. As illustrated in FIG. 34, the projection magnification factor is decreased by causing only the X-ray detector 52 to approach the imaging region ROI. Consequently, the blurring on the X-ray projection image due to the size of the focal plane 420 can be reduced.

When only the X-ray detector 52 is moved as illustrated in FIG. 34, a movement drive unit (not illustrated) that moves the X-ray detector 52 in the y-direction can be provided in the X-ray detection unit 50. The movement drive unit can be constructed with a linear motor type or ball screw type drive unit.

Figure 35:
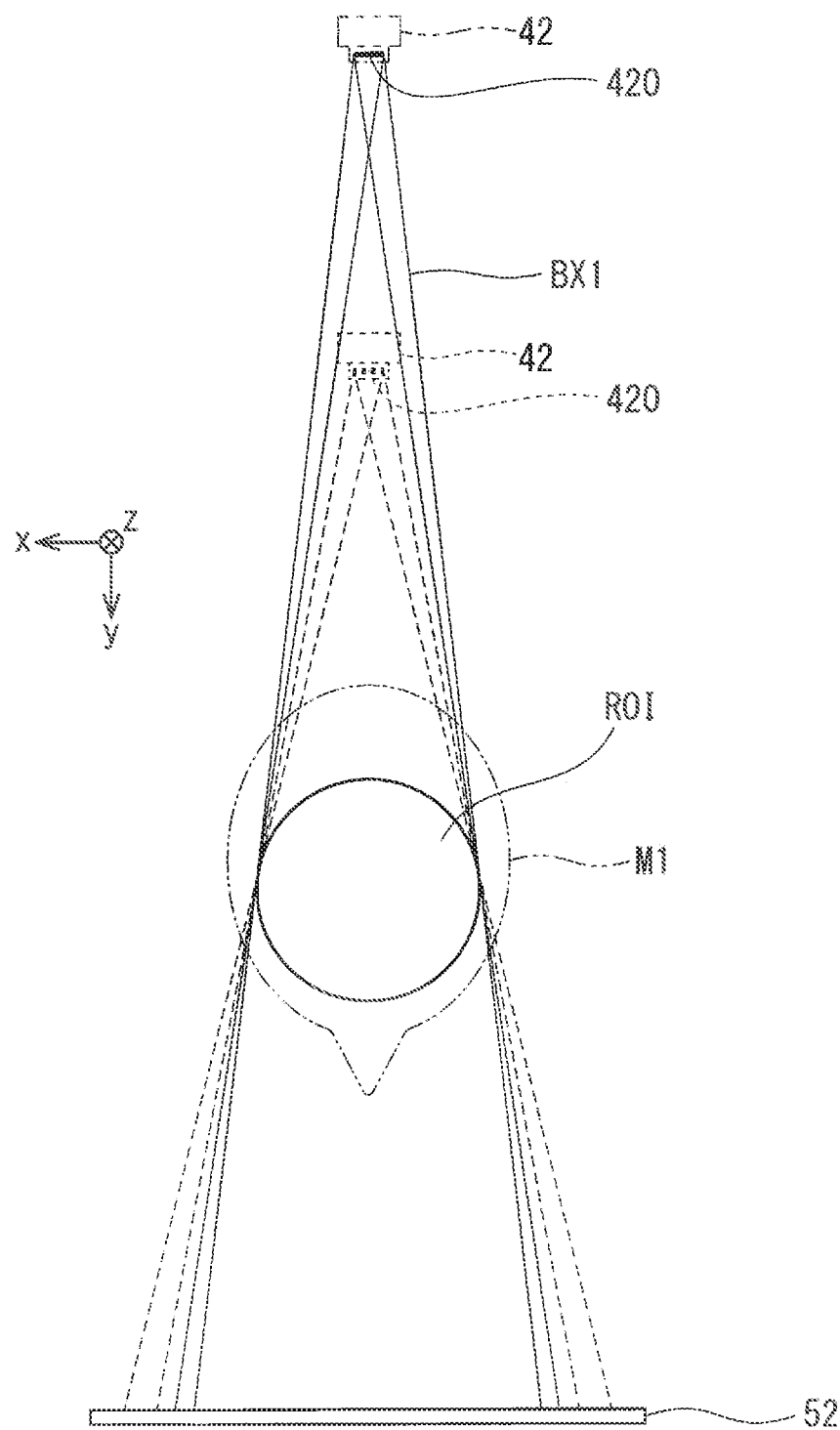
FIG. 35 is a view illustrating a state in which the projection magnification factor is decreased by moving only the X-ray generator 42.

FIG. 35 is a view illustrating the state in which the projection magnification factor is decreased by moving only the X-ray generator 42. As illustrated in FIG. 35, the projection magnification factor is decreased by moving only the X-ray generator 42 (focal plane 420) away from the imaging region ROI. Consequently, the blurring on the X-ray projection image due to the size of the focal plane 420 can be reduced. The focal plane 420 in FIGS. 34 and 35 is equivalent to the focal plane 420 in FIG. 18.

When only the X-ray generator 42 is moved, a movement drive unit that moves the entire X-ray generation unit 40 including the X-ray generator 42 in the y-direction can be provided in the turning arm 62. In this case, it is conceivable that the turning arm 62 is expandably configured.

Figure 36:
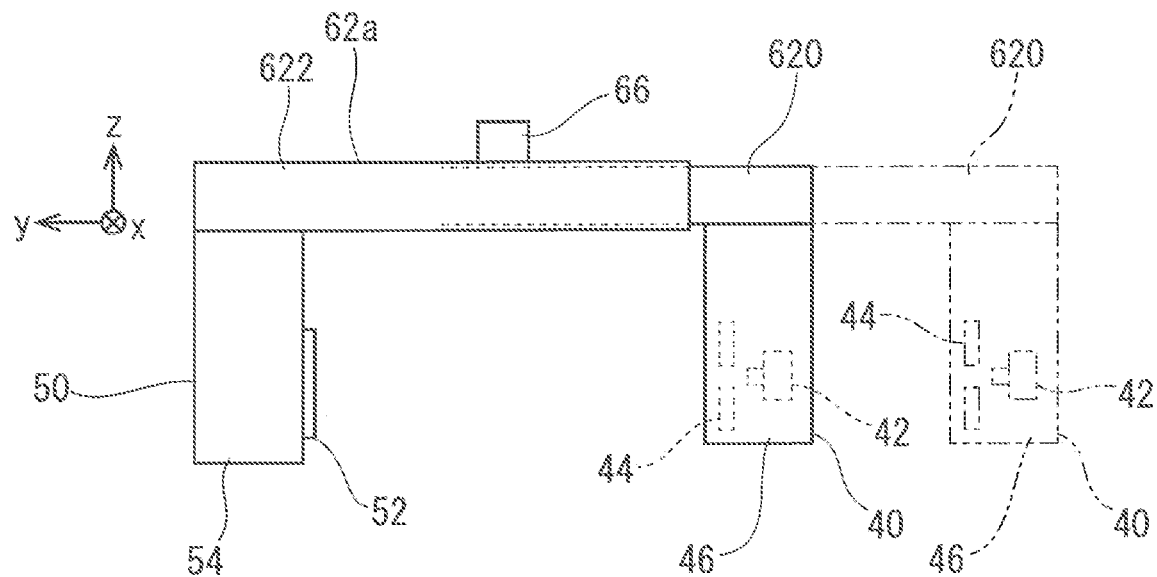
FIG. 36 is a schematic side view illustrating a turning arm 62a according to a modification.

FIG. 36 is a schematic side view illustrating a turning arm 62a according to a modification. As illustrated in FIG. 36, in the turning arm 62a, one end 620 supporting the X-ray generation unit 40 is configured to be accommodated inside a main body 622 of the turning arm 62. The turning arm 62a includes a movement drive unit (not illustrated) that moves the one end 620 in the y-direction. The movement drive unit accommodates the one end 620 in the main body 622, whereby the turning arm 62 is shortened and the X-ray generator 42 approaches the X-ray detector 52. The movement drive unit takes the one end 620 out of the main body 622, whereby the turning arm 62 is extended to separate the X-ray generator 42 from the X-ray detector 52.

In the turning arm 62a of the modification, the turning arm 62a itself is expandable when the X-ray generation unit 40 is moved. When the turning arm 62a passes through a space that collides with another member during the turning, the collision can be avoided by shortening the turning arm 62a.

Figure 37:
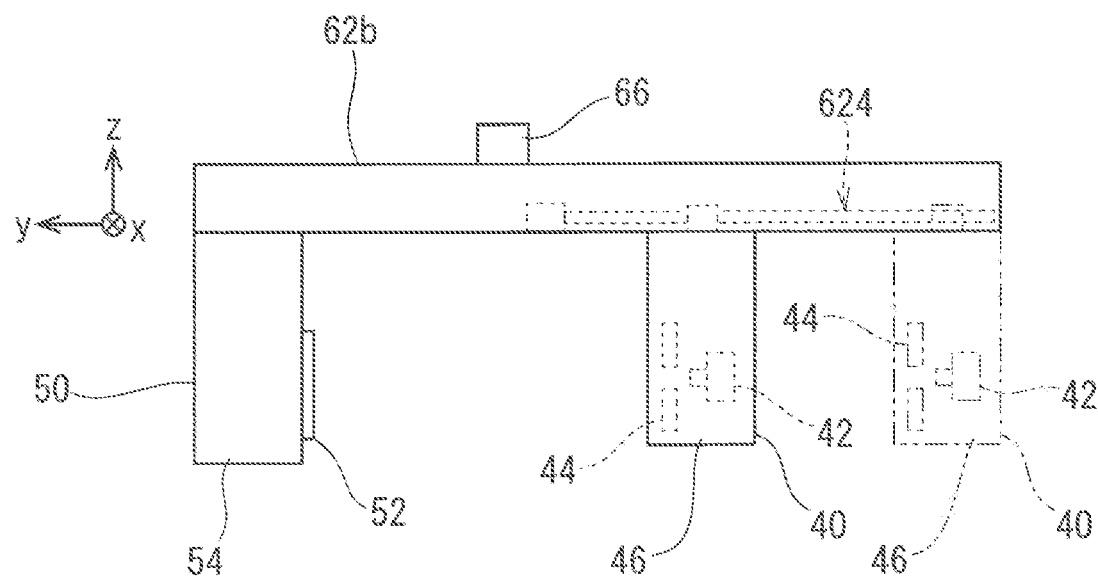
FIG. 37 is a schematic side view illustrating a turning arm 62b according to a modification.

FIG. 37 is a schematic side view illustrating a turning arm 62b according to a modification. The turning arm 62b includes a movement drive unit 624 that moves the X-ray generation unit 40 in the y-direction with respect to the turning arm 62. When the X-ray generator 42 confronts the tomographic layer of interest LOI during the X-ray tomography, the projection magnification factor can be decreased by moving the X-ray generator 42 in the direction in which the X-ray generator 42 is moved away from the subject M1.

For the turning arm 62b, by moving the X-ray generation unit 40 in the y-direction, the X-ray generation unit 40 can be prevented from contacting with another member during the turning. Because the turning arm 62b itself is not expandable, it is necessary that the turning arm 62b be turned such that the turning arm 62 does not contact with another member. In this respect, the turning arm 62a in FIG. 37 is more advantageous than the turning arm 62b.

X-ray Tomography in which X-ray Tomography is Started from Confronting State

Figure 38:
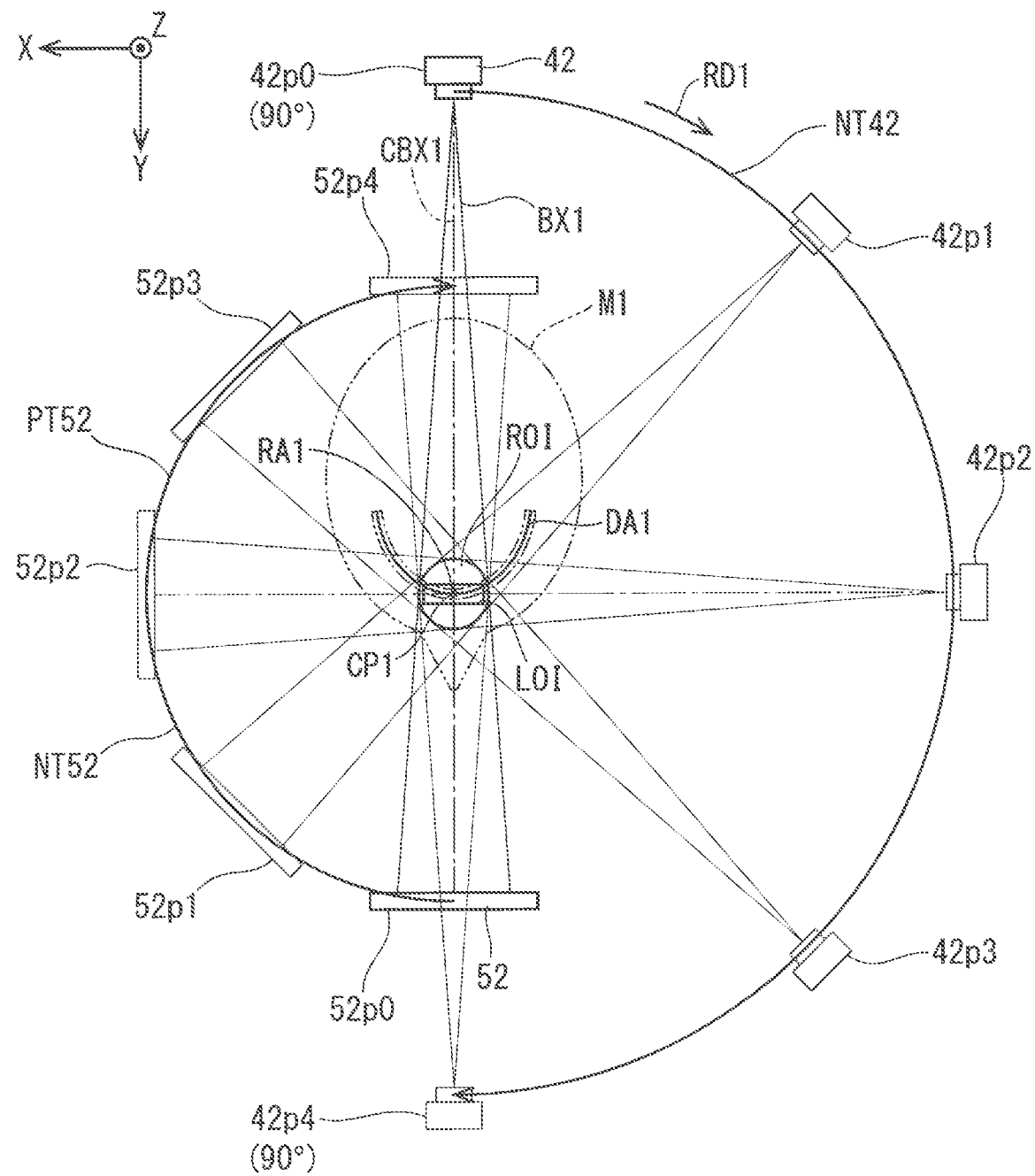
FIG. 38 is a view illustrating an example of the X-ray tomography.
Figure 39:
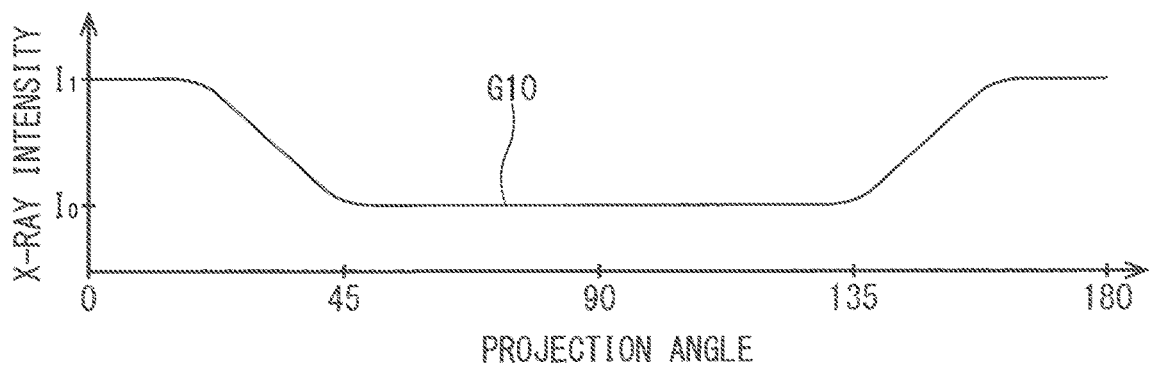
FIG. 39 is a view illustrating the graph G10 of the X-ray intensity corresponding to the projection angle in the CT imaging of FIG. 38.

FIG. 38 is a view illustrating an example of the X-ray tomography. FIG. 39 is a view illustrating the graph G10 of the X-ray intensity corresponding to the projection angle in the CT imaging of FIG. 38. The imaging region ROI and the tomographic layer of interest LOI in this CT imaging are matched with the imaging region ROI and the tomographic layer of interest LOI in the CT imaging of FIG. 9. However, this CT imaging differs from the CT imaging of FIG. 9 in that the position 42p0 of the X-ray generator 42 at the beginning of the X-ray is the position where the X-ray generator 42 confronts the tomographic layer of interest LOI.

As in this CT imaging, when the X-ray generator 42 starts the imaging from the state in which the X-ray generator 42 confronts the tomographic layer of interest LOI, the X-ray intensity is set to relatively large I1 at the projection angle of 0° as illustrated in FIG. 39. The X-ray intensity is set to I0 smaller than I1 in the period in which the X-ray generator 42 does not confront the tomographic layer of interest LOI (for example, the period in which the X-ray generator 42 passes through the positions 42p1 to 42p3). The X-ray generator 42 confronts the tomographic layer of interest LOI again at the position 42p4 where the projection angle becomes 180°. For this reason, the X-ray intensity can be increased to I1 until the X-ray generator 42 reaches the position 42p4. Although the change of the unit time dose is performed by the change of the X-ray intensity, the change of the unit time dose can be performed by the change of the turning velocity.

Example of X-ray Tomography in which X-ray Beam BX1 is Shifted

Figure 40:
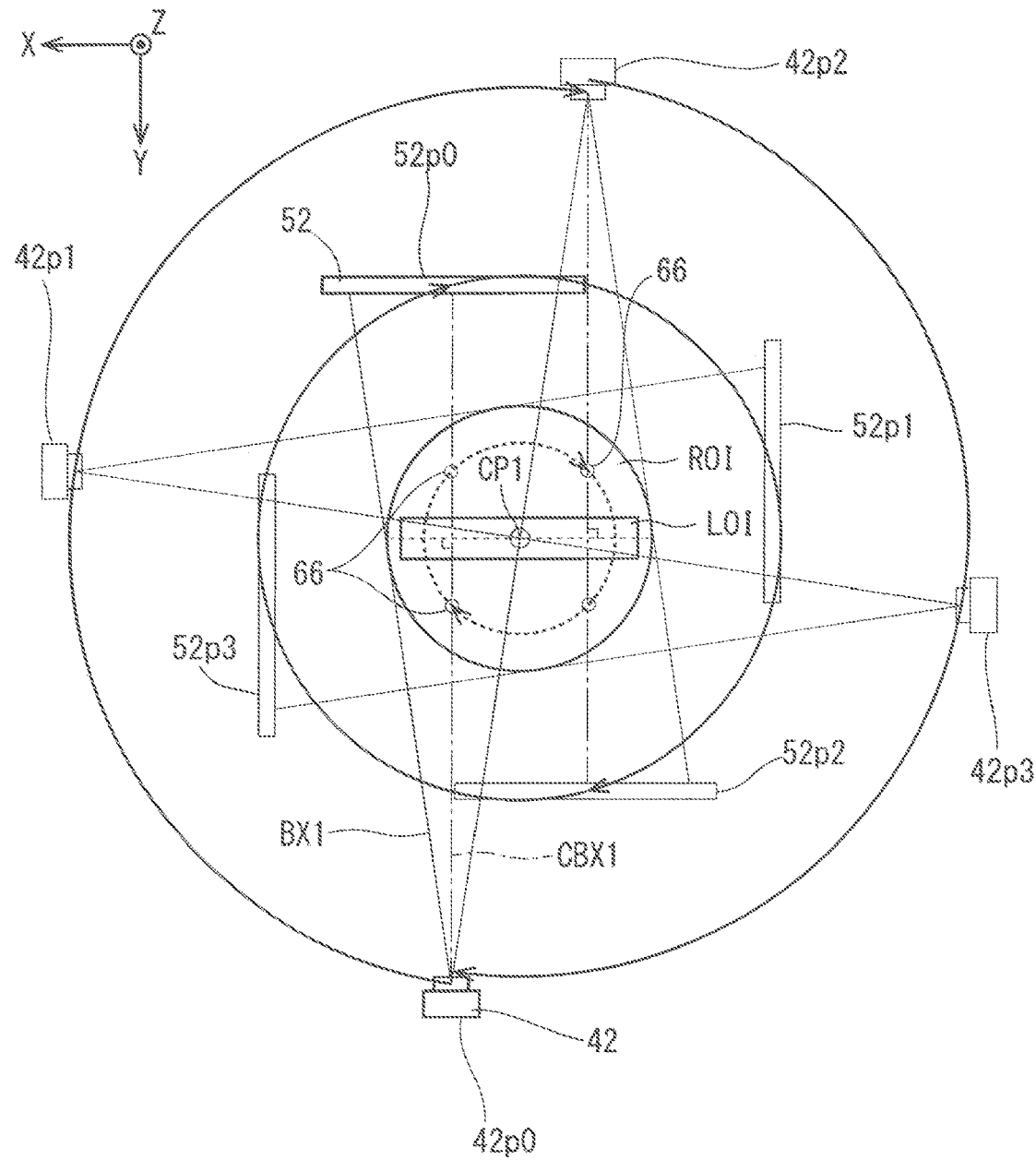
FIG. 40 is a view illustrating an example of the X-ray tomography.

FIG. 40 is a view illustrating an example of the X-ray tomography. The X-ray tomography in FIG. 40 is an example of the CT imaging called offset scan. In the offset scan, the X-ray detector 52 is disposed while laterally offset with respect to the center point CP1 of the imaging region ROI such that the irradiation range of the X-ray beam BX1 becomes greater than or equal to a half of the imaging region ROI and less than the whole imaging region ROI. The center axis X-ray CBX1 of the X-ray beam BX1 is set at a position displaced from the center point CP1 of the imaging region ROI. However, the turning center of the X-ray beam BX1 during the CT imaging is set to the center point CP1 of the imaging region ROI.

In the illustrated example, the CT imaging in which the X-ray projection data of the imaging region ROI is acquired is performed while the X-ray beam BX1 is shifted so as to always pass through the half of the imaging region ROI. In the CT imaging, the X-ray generator 42 is turned from the position 42p0 by 360° about the center point CP1 of the imaging region ROI to acquire the X-ray projection data for 180° with respect to the imaging region ROI. During the CT imaging, the imaging controller 80 controls the turning drive unit 642 and the XY-direction movement drive unit 644 to move the shaft 66 on the circular trajectory indicated by a broken line.

Also in the CT imaging, the unit time dose in the period in which the X-ray generator 42 confronts the tomographic layer of interest LOI can be increased larger than the unit time dose in the period in which the X-ray generator 42 does not confront the tomographic layer of interest LOI. In this example, the X-ray generator 42 becomes the state in which the center axis X-ray CBX1 of the X-ray beam BX1 emitted from the X-ray generator 42 is orthogonally incident on the tomographic layer of interest LOI, namely, the state in which the X-ray generator 42 confront the tomographic layer of interest LOI at the position 42p0 where the projection angle is 0° and the position 42p2 where the projection angle is 180°. For this reason, preferably, the unit time dose is relatively increased at the positions 42p0, 42p2.

Although the present invention is described in detail, the above description is illustrative in all aspects, and the present invention is not limited thereto. Innumerable modifications not illustrated can be made without departing from the scope of the present invention. The configurations described in the above embodiment and the modifications can appropriately be combined as long as they are not inconsistent with each other.

10: X-ray tomography apparatus
20: imaging unit
30: information processor
302: imaging region setting unit
304: tomographic layer-of-interest setting unit
306: imaging trajectory setting unit
308: dose setting unit
310: image processor
31: storage
34: operation unit
40: X-ray generation unit 42: X-ray generator
420: focal plane
44: X-ray regulating unit
52: X-ray detector
60: support
62, 62a, 62b: turning arm
642: turning drive unit
644: XY-direction movement drive unit
66: shaft
70: post
72: subject holder
80: imaging controller
802: turning controller
804: XY-direction movement controller
808: X-ray detection controller
810: X-ray generation controller
ANG1: incident angle
BX1: X-ray beam
CBX1: center axis X-ray
CP1: center point
DA1: dental arch
HA1: high X-ray absorption site
LOI: tomographic layer of interest
M1: subject
NT42: normal imaging trajectory
NT52: normal imaging trajectory
PT42: imaging trajectory
PT52: imaging trajectory
RA1: turning center axis
ROI: imaging region

The invention claimed is:

1. An X-ray tomography apparatus comprising:
an X-ray generator configured to emit an X-ray beam;
an X-ray detector configured to detect the X-ray beam emitted from the X-ray generator;
a support configured to support the X-ray generator and the X-ray detector;
a tomographic layer-of-interest setting unit configured to set a position of a tomographic layer of interest;
a turning driver configured to relatively turn the X-ray generator and the X-ray detector around at least a turning center axis with respect to the tomographic layer of interest;
an image processor configured to generate an X-ray tomographic image indicating the tomographic layer of interest by performing image processing on a projection image generated based on an output signal output from the X-ray detector; and
a processor configured to control the turning driver and a change in a unit time dose that is an X-ray dose with which the tomographic layer of interest is irradiated per unit time,
wherein the processor is further configured to control the turning driver and the change in the unit time dose such that the unit time dose in at least a part of a period in which a center axis of the X-ray beam is not orthogonal to the tomographic layer of interest is relatively smaller than the unit time dose in a period in which the center axis of the X-ray beam is orthogonal to the tomographic layer of interest.

2. The X-ray tomography apparatus according to claim 1, wherein
the support includes a turning arm that supports the X-ray generator at one end side while supporting the X-ray detector at the other end side, and
the turning drive unit turns the turning arm via a shaft, the shaft connected to a position between the X-ray generator and the X-ray detector in the turning arm.

3. The X-ray tomography apparatus according to claim 1, further comprising an imaging region setting unit configured to set an imaging region irradiated by the X-ray beam from a plurality of directions whereby a plurality of projection images are acquired, the imaging region setting unit further configured to set the imaging region based on an input operation of designation through an operation unit.

4. The X-ray tomography apparatus according to claim 3, wherein the tomographic layer-of-interest setting unit sets the position of the tomographic layer of interest according to the imaging region set by the imaging region setting unit.

5. The X-ray tomography apparatus according to claim 4, wherein
the operation unit receives designation of the imaging region so as to include a part of a dental arch, and
the tomographic layer-of-interest setting unit sets the tomographic layer of interest along the part of the dental arch included in the imaging region.

6. The X-ray tomography apparatus according to claim 1, wherein
the controller increases or decreases the unit time dose by increasing or decreasing intensity of the X-ray beam emitted from the X-ray generator, and
the image processor generates the X-ray tomographic image after performing smoothing processing on the projection image obtained by irradiation of the X-ray beam having intensity lower than a predetermined threshold.

7. The X-ray tomography apparatus according to claim 1, further comprising a tomographic thickness designation receiving unit configured to receive designation of a tomographic thickness of the tomographic layer of interest,
wherein the controller determines an incident angle of the X-ray beam when the unit time dose is increased and decreased according to the designated tomographic thickness.

8. The X-ray tomography apparatus according to claim 3, wherein based on position information indicating a position of a high X-ray absorption site where X-ray absorptance is higher than that of other sites, the controller makes the unit time dose when the high X-ray absorption site is present on a path of the X-ray beam lager than the unit time dose when the high X-ray absorption site is absent.

9. The X-ray tomography apparatus according to claim 1, further comprising a movement drive unit configured to move the X-ray detector relative to the tomographic layer of interest in a direction perpendicular to the turning center axis,
wherein, when the center axis of the X-ray beam is orthogonal to the tomographic layer of interest, the controller controls the movement drive unit to causes the X-ray detector to approach the tomographic layer of interest or move the X-ray generator away from the tomographic layer of interest as compared with at least a part of the period in which the center axis of the X-ray beam is not orthogonal to the tomographic layer of interest.

10. The X-ray tomography apparatus according to claim 1, wherein
the support includes a turning arm that supports the X-ray generator at one end side while supporting the X-ray detector at the other end side, the turning driver comprising a motor configured to turn the turning arm around a shaft through which the turning axis passes.

11. The X-ray tomography apparatus according to claim 10, wherein
the turning driver further comprising an XY direction movement driver that moves the shaft in a plane orthogonal to the turning axis.

12. An X-ray tomography method comprising:
setting a position of a tomographic layer of interest;
relatively turning an X-ray generator and an X-ray detector around a turning center axis with respect to the tomographic layer of interest while the tomographic layer of interest is disposed between the X-ray generator and the X-ray detector;
detecting an X-ray beam emitted from the X-ray generator using the X-ray detector;
changing a unit time dose that is an X-ray dose with which the tomographic layer of interest is irradiated per unit time; and
generating an X-ray tomographic image indicating the tomographic layer of interest by performing image processing on a plurality of projection images generated based on an output signal output from the X-ray detector,
wherein the changing is changing the unit time dose such that the unit time dose in at least a part of a period in which a center axis of the X-ray beam is not orthogonal to the tomographic layer of interest is relatively smaller than the unit time dose in a period in which the center axis of the X-ray beam is orthogonal to the tomographic layer of interest.

13. An X-ray tomography apparatus comprising:
an X-ray generator configured to emit an X-ray beam;
an X-ray detector configured to detect the X-ray beam emitted from the X-ray generator;
a support configured to support the X-ray generator and the X-ray detector;
a tomographic layer-of-interest setting unit configured to set a position of a tomographic layer of interest;
a turning drive unit configured to relatively turn the X-ray generator and the X-ray detector around at least a turning center axis with respect to the tomographic layer of interest;
an image processor configured to generate an X-ray tomographic image indicating the tomographic layer of interest by performing image processing on a projection image generated based on an output signal output from the X-ray detector; and
a controller configured to control the turning drive unit and an increase or decrease in a unit time dose that is an X-ray dose with which the tomographic layer of interest is irradiated per unit time,
wherein the controller is further configured to control the turning drive unit and a change in the unit time dose such that the unit time dose in a period in which the X-ray beam is incident on the tomographic layer of interest in a confronting manner is relatively larger than the unit time dose in at least a part of a period in which the X-ray beam is not incident on the tomographic layer of interest in the confronting manner.

14. An X-ray tomography apparatus comprising:
an X-ray generator configured to emit an X-ray beam;
an X-ray detector configured to detect the X-ray beam emitted from the X-ray generator;
a support configured to support the X-ray generator and the X-ray detector;
a tomographic layer-of-interest setting unit configured to set a position of a tomographic layer of interest;
a turning drive unit configured to relatively turn the X-ray generator and the X-ray detector around at least a turning center axis with respect to the tomographic layer of interest;
an image processor configured to generate an X-ray tomographic image indicating the tomographic layer of interest by performing image processing on a projection image generated based on an output signal output from the X-ray detector; and
a controller configured to control the turning drive unit and a change in a unit time dose that is an X-ray dose with which the tomographic layer of interest is irradiated per unit time,
wherein, assuming that an incident angle of a center axis of the X-ray beam ranging from 85° to 95° with respect to the tomographic layer of interest is a state in which the X-ray generator confronts the tomographic layer of interest,
the controller is further configured to control the turning drive unit and the change in the unit time dose such that the unit time dose in at least a part of a period in which the X-ray generator does not confront the tomographic layer of interest is relatively smaller than the unit time dose in a period in which the X-ray generator confronts the tomographic layer of interest.

* * * * *